(12) United States Patent
Lee

(10) Patent No.: US 7,317,950 B2
(45) Date of Patent: Jan. 8, 2008

(54) CARDIAC STIMULATION SYSTEM WITH DELIVERY OF CONDUCTIVE AGENT

(75) Inventor: Randall J. Lee, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 514 days.

(21) Appl. No.: 10/374,899

(22) Filed: Feb. 24, 2003

(65) Prior Publication Data

US 2004/0098075 A1 May 20, 2004

Related U.S. Application Data

(60) Provisional application No. 60/426,840, filed on Nov. 16, 2002.

(51) Int. Cl.
*A61N 1/05* (2006.01)
*A61N 1/362* (2006.01)
*A61N 1/39* (2006.01)

(52) U.S. Cl. .............................. 607/122; 607/3; 607/5; 607/9

(58) Field of Classification Search ..................... None
See application file for complete search history.

(56) References Cited

U.S. PATENT DOCUMENTS

| 4,316,472 | A | 2/1982 | Mirowski et al. |
| 4,354,497 | A | 10/1982 | Kahn |
| 4,399,818 | A | 8/1983 | Money |
| 4,565,200 | A | 1/1986 | Cosman |
| 4,569,801 | A | 2/1986 | Molloy et al. |
| 4,616,333 | A | 10/1986 | Shimoni |

(Continued)

FOREIGN PATENT DOCUMENTS

DE 296 09 350 U1 10/1995

(Continued)

OTHER PUBLICATIONS

Sueda, Taijiro et al, Simple Left Atrial Procedure for Chronic Atrial Fibrillation Associated with Mitral Valve Disease; Ann Thorac Surg, Jun. 27, 1996; 62:1796-800.

(Continued)

*Primary Examiner*—Kristen D. Mullen
(74) *Attorney, Agent, or Firm*—Carol L. Francis; Gina C. Freschi; Bozicevic, Field & Francis LLP

(57) ABSTRACT

A cardiac stimulation assembly includes an energy source coupled to an energy emitter that extends form a delivery member into a region of tissue in the heart. An array of the emitters are adapted to extend from a delivery assembly and into unique locations along the region of tissue, such as by use of extendable, pre-shaped needles. A volume of conductive agent is delivered into the region and enhances stimulation of the region with the energy emitter. The agent may be an injectable preparation of living cells that express production of connexin, e.g. connexin 43, and may be genetically modified to over-express such production. The agent may include a non-living material, such as conductive polymer or metal or combination thereof. The combination of energy emitters and conductive agent enhances stimulation of the region. Delivering the stimulation assembly and conductive agent into the interventricular septum allows for improved biventricular septal pacing.

76 Claims, 18 Drawing Sheets

U.S. PATENT DOCUMENTS

| | | |
|---|---|---|
| 4,641,649 A | 2/1987 | Walinsky et al. |
| 4,660,571 A | 4/1987 | Hess et al. |
| 4,699,147 A | 10/1987 | Chilson et al. |
| 4,790,311 A | 12/1988 | Ruiz |
| 4,790,317 A | 12/1988 | Davies |
| 4,799,493 A | 1/1989 | DuFault |
| 4,807,620 A | 2/1989 | Strul et al. |
| 4,882,777 A | 11/1989 | Narula |
| 4,920,980 A | 5/1990 | Jackowski |
| 4,940,064 A | 7/1990 | Desai |
| 4,974,598 A | 12/1990 | John |
| 4,998,933 A | 3/1991 | Eggers et al. |
| 5,007,908 A | 4/1991 | Rydell |
| 5,058,599 A | 10/1991 | Andersen |
| 5,074,313 A | 12/1991 | Dahl et al. |
| 5,103,821 A | 4/1992 | King |
| 5,107,850 A | 4/1992 | Olive |
| 5,130,141 A | 7/1992 | Law et al. |
| 5,158,079 A | 10/1992 | Adams et al. |
| 5,209,229 A | 5/1993 | Gilli |
| 5,222,501 A | 6/1993 | Ideker et al. |
| 5,228,442 A | 7/1993 | Imran |
| 5,231,995 A | 8/1993 | Desai |
| 5,255,679 A | 10/1993 | Imran |
| 5,259,395 A | 11/1993 | Li |
| 5,263,493 A | 11/1993 | Avitall |
| 5,293,868 A | 3/1994 | Nardella |
| 5,293,869 A | 3/1994 | Edwards et al. |
| 5,300,085 A | 4/1994 | Yock |
| 5,311,873 A | 5/1994 | Savard et al. |
| 5,313,943 A | 5/1994 | Houser et al. |
| 5,314,460 A | 5/1994 | Borghi |
| 5,314,461 A | 5/1994 | Borghi |
| 5,324,284 A | 6/1994 | Imran |
| 5,325,860 A | 7/1994 | Seward et al. |
| 5,331,966 A | 7/1994 | Bennett et al. |
| 5,336,222 A | 8/1994 | Durgin, Jr. et al. |
| 5,336,251 A | 8/1994 | Borghi |
| 5,345,936 A | 9/1994 | Pomeranz et al. |
| 5,345,940 A | 9/1994 | Seward et al. |
| 5,366,486 A | 11/1994 | Zipes et al. |
| 5,366,487 A | 11/1994 | Adams et al. |
| 5,366,490 A | 11/1994 | Edwards et al. |
| 5,370,675 A | 12/1994 | Edwards et al. |
| 5,370,678 A | 12/1994 | Edwards et al. |
| 5,385,544 A | 1/1995 | Edwards et al. |
| 5,391,199 A | 2/1995 | Ben-Haim |
| 5,400,796 A | 3/1995 | Wecke |
| 5,403,311 A | 4/1995 | Abele et al. |
| 5,405,376 A | 4/1995 | Mulier et al. |
| 5,409,000 A | 4/1995 | Imran |
| 5,409,453 A | 4/1995 | Lundquist et al. |
| 5,411,524 A | 5/1995 | Rahul |
| 5,421,819 A | 6/1995 | Edwards et al. |
| 5,423,808 A | 6/1995 | Edwards et al. |
| 5,423,811 A | 6/1995 | Imran et al. |
| 5,427,119 A | 6/1995 | Swartz et al. |
| 5,431,649 A | 7/1995 | Mulier et al. |
| 5,433,198 A | 7/1995 | Desai |
| 5,433,708 A | 7/1995 | Nichols et al. |
| 5,435,805 A | 7/1995 | Edwards et al. |
| 5,439,483 A | 8/1995 | Duong-Van |
| 5,450,846 A | 9/1995 | Goldreyer |
| 5,464,431 A | 11/1995 | Adams et al. |
| 5,470,308 A | 11/1995 | Edwards et al. |
| 5,476,503 A | 12/1995 | Yang |
| 5,484,400 A | 1/1996 | Edwards et al. |
| 5,485,849 A | 1/1996 | Panescu et al. |
| 5,487,385 A | 1/1996 | Avitall |
| 5,496,312 A | 3/1996 | Klicek |
| 5,496,360 A | 3/1996 | Hoffmann et al. |
| 5,500,012 A | 3/1996 | Brucker et al. |
| 5,507,802 A | 4/1996 | Imran |
| 5,509,900 A | 4/1996 | Kirkman |
| 5,545,193 A | 8/1996 | Fleischman et al. |
| 5,549,641 A | 8/1996 | Ayers et al. |
| 5,549,661 A | 8/1996 | Kordis et al. |
| 5,562,720 A | 10/1996 | Stern et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,810 A | 11/1996 | Swanson et al. |
| 5,582,609 A | 12/1996 | Swanson et al. |
| 5,588,432 A | 12/1996 | Crowley |
| 5,605,159 A | 2/1997 | Smith et al. |
| 5,606,974 A | 3/1997 | Castellano et al. |
| 5,607,422 A | 3/1997 | Smeets et al. |
| 5,607,462 A | 3/1997 | Imran |
| 5,609,151 A | 3/1997 | Mulier et al. |
| 5,617,854 A | 4/1997 | Munsif |
| 5,642,736 A | 7/1997 | Avitall |
| 5,645,082 A | 7/1997 | Sung et al. |
| 5,661,133 A | 8/1997 | Leiden et al. |
| 5,674,274 A | 10/1997 | Morgan et al. |
| 5,676,153 A | 10/1997 | Smith et al. |
| 5,676,662 A | 10/1997 | Fleischhacker et al. |
| 5,680,860 A | 10/1997 | Imran |
| 5,681,308 A | 10/1997 | Edwards et al. |
| 5,683,447 A | 11/1997 | Bush et al. |
| 5,687,723 A | 11/1997 | Avitall |
| 5,688,267 A | 11/1997 | Panescu et al. |
| 5,690,611 A | 11/1997 | Swartz et al. |
| 5,693,078 A | 12/1997 | Desai et al. |
| 5,693,622 A | 12/1997 | Wolff et al. |
| 5,697,927 A | 12/1997 | Imran et al. |
| 5,702,433 A | 12/1997 | Taylor et al. |
| 5,716,389 A | 2/1998 | Walinsky et al. |
| 5,718,241 A | 2/1998 | Ben-Haim et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,728,140 A | 3/1998 | Salo et al. |
| 5,730,127 A | 3/1998 | Avitall |
| 5,730,704 A | 3/1998 | Avitall |
| 5,735,280 A | 4/1998 | Sherman et al. |
| 5,735,846 A | 4/1998 | Panescu et al. |
| 5,741,320 A | 4/1998 | Thornton et al. |
| 5,755,663 A | 5/1998 | Larsen et al. |
| 5,755,760 A | 5/1998 | Maguire et al. |
| 5,769,846 A | 6/1998 | Edwards et al. |
| 5,782,239 A | 7/1998 | Webster, Jr. |
| 5,782,898 A | 7/1998 | Dahl et al. |
| RE35,880 E | 8/1998 | Waldman et al. |
| 5,797,842 A | 8/1998 | Pumares et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,413 A | 9/1998 | Swartz et al. |
| 5,800,428 A | 9/1998 | Nelson et al. |
| 5,800,432 A | 9/1998 | Swanson |
| 5,807,249 A | 9/1998 | Qin et al. |
| 5,807,395 A | 9/1998 | Mulier et al. |
| 5,840,031 A | 11/1998 | Crowley |
| 5,840,076 A | 11/1998 | Swanson et al. |
| 5,842,984 A | 12/1998 | Avitall |
| 5,843,154 A | 12/1998 | Osypka |
| 5,885,278 A | 3/1999 | Fleischman |
| 5,921,982 A | 7/1999 | Lesh et al. |
| 5,938,660 A | 8/1999 | Swartz et al. |
| 5,971,983 A | 10/1999 | Lesh |
| 6,001,093 A | 12/1999 | Swanson et al. |

| | | | |
|---|---|---|---|
| 6,012,457 A | 1/2000 | Lesh | |
| 6,024,740 A | 2/2000 | Lesh et al. | |
| 6,059,726 A | 5/2000 | Lee et al. | |
| 6,063,077 A | 5/2000 | Schaer | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,071,282 A | 6/2000 | Fleischman | |
| 6,090,084 A | 7/2000 | Hassett et al. | |
| 6,101,410 A | 8/2000 | Panescu et al. | |
| 6,117,101 A | 9/2000 | Diederich et al. | |
| 6,128,535 A | 10/2000 | Maarse | |
| 6,129,761 A | 10/2000 | Hubbell | |
| 6,146,379 A | 11/2000 | Fleischman et al. | |
| 6,151,525 A | 11/2000 | Soykan et al. | |
| 6,161,543 A | 12/2000 | Cox et al. | |
| 6,164,283 A | 12/2000 | Lesh | |
| 6,214,002 B1 | 4/2001 | Fleischman et al. | |
| 6,238,429 B1 | 5/2001 | Markowitz et al. | |
| 6,242,473 B1 | 6/2001 | Hellstrand et al. | |
| 6,245,059 B1 | 6/2001 | Clapham | |
| 6,261,832 B1 | 7/2001 | Law | |
| 6,312,685 B1 | 11/2001 | Fisher et al. | |
| 6,330,476 B1 | 12/2001 | Ben-Haim et al. | |
| 6,443,949 B2 | 9/2002 | Altman | |
| 6,502,576 B1 | 1/2003 | Lesh | |
| 6,511,477 B2 | 1/2003 | Altman et al. | |
| 6,533,819 B1 | 3/2003 | Urry et al. | |
| 6,547,787 B1 | 4/2003 | Altman et al. | |
| 6,709,427 B1* | 3/2004 | Nash et al. | 604/508 |
| 7,094,201 B1* | 8/2006 | Stokes et al. | 600/120 |
| 2001/0025193 A1 | 9/2001 | Prutchi | |
| 2002/0031501 A1 | 3/2002 | Law | |
| 2002/0035388 A1 | 3/2002 | Lindemans et al. | |
| 2002/0044925 A1 | 4/2002 | Law | |
| 2002/0087089 A1 | 7/2002 | Ben-Haim | |
| 2002/0123771 A1 | 9/2002 | Ideker et al. | |
| 2003/0199957 A1* | 10/2003 | Struble et al. | 607/122 |

FOREIGN PATENT DOCUMENTS

| | | |
|---|---|---|
| DE | 195 37 084 A1 | 4/1997 |
| EP | 0 149 431 A2 | 7/1985 |
| EP | 0 452 278 A2 | 10/1991 |
| EP | 0 609 182 A1 | 8/1994 |
| EP | 0 672 431 A2 | 9/1995 |
| EP | 0 672 432 A1 | 9/1995 |
| EP | 0 452 278 B1 | 11/1995 |
| WO | WO 90/10471 | 9/1990 |
| WO | WO9010471 | 9/1990 |
| WO | WO 93/00958 | 1/1993 |
| WO | WO 93/16632 | 9/1993 |
| WO | WO 93/20767 | 10/1993 |
| WO | WO 93/20886 | 10/1993 |
| WO | WO 94/21165 | 9/1994 |
| WO | WO 94/21167 | 9/1994 |
| WO | WO 94/21168 | 9/1994 |
| WO | WO 95/05781 | 3/1995 |
| WO | WO9505781 | 3/1995 |
| WO | WO 95/10318 | 4/1995 |
| WO | WO 95/10319 | 4/1995 |
| WO | WO 95/10321 | 4/1995 |
| WO | WO 95/15115 | 6/1995 |
| WO | WO 96/18303 | 6/1996 |
| WO | WO 96/32885 | 10/1996 |
| WO | WO 96/32897 | 10/1996 |
| WO | WO 97/32525 | 9/1997 |
| WO | WO 97/37607 | 10/1997 |
| WO | WO 97/45156 | 12/1997 |
| WO | WO 98/02150 | 1/1998 |
| WO | WO 98/02201 | 1/1998 |
| WO | WO 98/28039 | 7/1998 |
| WO | WO0168814 | 9/2001 |
| WO | WO 02/22206 A1 | 3/2002 |
| WO | WO0222206 | 3/2002 |
| WO | WO 02/051495 A2 | 7/2002 |

OTHER PUBLICATIONS

Schuger, Claudio D. et al, Long-term Effects of Percutaneous Laser Balloon Ablation From the Canine Coronary Sinus; Circulation vol. 86, No. 3, Sep. 1992.

McMath, Linda P. et al, Percutaneous Laser Balloon Coagulation of Accessory Pathways; SPIE vol. 1425: 165-71 Diagnostic and Therapeutic Cardiovascular Interventions (1991).

Jais, MD, Pierre et al, Biatrial Dimensions Relevant to Catheter Ablation; North American Society of . . . ; 17th Annual Scientific Sessions Abstract Form, Nov. 28, 1995.

Lesh, MD, Michael D., Interventional Electrophysiology State-of-the-art 1993; American Heart Journal vol. 126, No. 3, Part 1: 686-698, Sep. 1993.

Jais, MD, Pierre et al, A Focal Source of Atrial Fibrillation Treated by Discrete Radiofrequency Ablation; Circulation vol. 95, No. 3, Feb. 4, 1997; 572-576.

Hendricks, MD, Gerhard et al, Catheter Ablation; Current Management of Arrhythmias; Ch IX Nonpharmacologic Management: 373-378; no date available.

Haissaguerre, MD, Michel et al, Right and Left Atrial Radiofrequency Catheter . . . ; Journal of Cardiovasscular Electrophysiology vol. 7, No. 12, Dec. 1996: 1132-1144.

Fram, Daniel B. et al, Feasibility of Radiofrequency Powered, Thermal Balloon Ablation of Atrioventricular . . . ; PACE, vol. 18, Aug. 1995:1518-1530.

Cox, MD, James L., The Surgical Treatment of Atrial Fibrillation; IV. Surgical Technique; The Journal of Thoracic and Cardiovascular Surgery, Apr. 1991; 101: 584-92.

Cox, MD, James L. et al, The Surgical Treatment of Atrial Fibrillation; I. Summary of the Current . . . ; Journal of Thoracic and Cardiovascular Surgery, Mar. 1991;101: 402-405.

Diederich, Chris J. et al, Induction of Hyperthermia Using an Intracavitary Multielement . . . ; IEEE Transactions on Biomedical Engineering vol. 36, No. 4, Apr. 1989: 432-438.

Diederich, C. J. et al, The Development of Intracavitary Ultrasonic Applicators for Hyperthermia: A Design . . . ; Medical Physics, vol. 17, No. 4, Jul./Aug. 1990.

Avitall, MD, Boaz et al, Physics and Engineering of Transcatheter Cardiac Tissue Ablation; JACC vol. 22, No. 3; Sep. 1993: 921-32.

O'Brien, David P. et al, Flexible Microelectrode Arrays with Intergrated Insertion Devices; MEMS '01, pp. 216-219, 2002.

Long, Carlin S. et al, The Cardiac Fibroblast, Another Therapeutic Target For Mending The Broken Heart?; J Molecular Cell Cardiology, vol. 34, pp. 1273-1278, Mar. 7, 2002.

Suzuki, K. et al, Overexpression of Connexin 43 in Skeletal Myoblasts . . . ; Journal of Thoracic and Cardiovascular Surgery, vol. 122, No. 4, pp. 759-766, Oct. 2001.

Feld, Yair et al, Electrophysiological Modulation of Cardiomyocytic Tissue by Transfected Fibroblasts Expressing . . . ; Circulation, vol. 105, pp. 522-529, Jan. 29, 2002.

Murry, Charles E. et al, Muscle Cell Grafting for the Treatment and Prevention of Heart Failure; J Cardiac Failure, vol. 8, No. 6, pp. S532-S541, (Suppl. Dec. 2002).

Atkins, B. Zane et al, Myogenic Cell Transplantation Improves In Vivo Regional Performance . . . ; J Heart Lung Transplant 1999; 18:1173-1180. (Dec. 1999).

Janus, Edward D. et al, The Modernization of Asia, Implications for Coronary Heart Disease; Circulation, vol. 94, pp. 2671-2673, Dec. 1, 1996.

Orlic, Donald et al, Bone Marrow Cells Regenerate Infarcted Myocardium; Letters to Nature, vol. 410, pp. 701-705, Apr. 2001.

Reinecke, Hans et al, Transmural Replacement of Myocardium After Skeletal Myoblast Grafting Into . . . ; Cardiovascular Pathology, vol. 9, No. 6,pp. 337-344, Dec. 2000.

\* cited by examiner

CARDIAC STIMULATION SYSTEM WITH DELIVERY OF CONDUCTIVE AGENT

CROSS-REFERENCE TO RELATED APPLICATIONS

This application claims benefit of priority to U.S. Provisional Patent Application Ser. No. 60/426,840 filed on Nov. 16, 2002, which is herein incorporated in its entirety by reference thereto.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

This invention is a system and method for stimulating a heart of a patient. More specifically, it is a stimulation device assembly and method using a stimulator coupled with an implantable emitter that is in turn coupled with a conductive agent injected into the region of the heart to be stimulated.

2. Description of the Background Art

Various medical device systems and methods have been disclosed for coupling energy to cardiac tissue in order to influence heart function. A great many of such systems and methods have been disclosed for the particular purpose of treating various types of cardiac arrhythmias, including for example fibrillation, tachycardia, bradycardia, or other arrhythmias.

Among the many different devices and methods previously disclosed for energy coupling to cardiac tissue, various different types of energy coupling have also been employed.

One type of energy coupling having significant impact over the years in treating cardiac arrhythmias delivers energy into targeted regions of cardiac tissue using energy emitters in or around the heart. Various previously disclosed examples of energy delivery systems and methods of this type include devices using: emitters of electrical energy, e.g. electrodes for delivering direct or alternating current, such as radiofrequency (RF) current; emitters such as crystals or transducers for delivering sonic energy (e.g. ultrasound); emitters such as fiber optics, lenses, or other light discharge elements (e.g. laser diodes) for delivering light (e.g. laser); or energy emitters using microwave coupling (e.g. induction).

Another type of energy coupling that has been investigated for treating certain cardiac arrhythmias includes hypothermia or cryogenic devices intended to reduce tissue temperature to a level. In general, these devices include regions that are cooled to low temperatures (relative to surrounding body temperature) so as to thereby pull heat from and reduce the temperature in surrounding tissue. By achieving this heat transfer at sufficient levels, an intended change in the affected tissue structure or function, either temporarily or permanently. To the extent that such hypothermic coupling relates to pulling thermal energy from the surrounding tissue so as to cool it, such devices are considered energy coupling devices.

The designs and features of the various different energy coupling devices for cardiac treatment also vary in order to adapt such devices to achieve different intended results.

For example, certain such devices and methods generally herein referred to as "ablation devices" are specifically adapted to couple sufficient energy with cardiac tissue so as to ablate the tissue. This may be performed for example in order to terminate a focal origin of arrhythmia, or to form a conduction block to terminate a harmful conduction pathway within the cardiac tissue network causing arrhythmia.

Other ablation devices have also been disclosed for the purpose of forming passageways through tissue or other material located within a patient, such as for recanalization of occluded lumens and vessels.

Other previously disclosed examples of cardiac treatment devices using energy coupling have been specifically adapted to stimulate cardiac tissue, rather than to ablate it. Various types of these cardiac stimulation systems include: devices adapted to couple energy to cardiac tissue in a manner so as to trigger an arrhythmia in order to diagnose cardiac conduction through the heart; pacemaker assemblies and methods adapted to provide artificial pacing of the cardiac cycle in order to cure an arrhythmia; and defibrillator assemblies and methods wherein the heart is "shocked" out of an arrhythmia and back into sinus rhythm.

Because the cardiac conduction cycle is directly and intimately related to electrical conduction through cardiac tissue, the previously disclosed cardiac stimulation devices for triggering, pacing, or defibrillating, are generally electrical coupling devices that deliver electrical energy from electrode leads or catheters secured to or placed against the tissue to be stimulated. Pacemaker and defibrillator assemblies have each been adapted with varied (and in some regards mutually exclusive) designs appropriate to suit one or the other of temporary or permanent use, depending upon a particular need for either acute or chronic rhythm management, respectively.

In general, permanent pacemaker systems include a pacemaker assembly with a pacemaker coupled to an electrical lead generally called a "pacemaker lead". The implantable or permanent pacemaker typically includes a power source, such as a source of electrical current energy (e.g. a battery). This power source is electrically coupled to one end of the electrical lead. The other end of the electrical lead is in turn coupled to the cardiac tissue to be stimulated, usually by use of an anchor such as a needle, screw, spline, grasper, etc., which anchor may be the electrode current emitter itself.

In recent years, an increasing amount of interest, and research and development, has been directed toward modifying the cellular make-up of cardiac tissue structures in order to enhance cardiac conduction or function in such modified structures.

Certain such efforts have been directed toward delivering conductive, contractile muscle cells into regions of the heart where contraction is compromised, such as areas of necrosis. These efforts have been intended to increase the cardiac function in such areas. Such cells delivered may be for example prepared from cultures of the patient's own cells, which may be cardiac cells for example, but may also be skeletal cells, fibroblasts or stem cells. The delivered cells may also be modified in a manner to enhance their contractile function or conductivity, and including to enhance their expression of certain factor(s), such as for example to enhance expression of connexin 43, a protein known to enhance cardiac signal conduction.

Connexins are found in connexons of gap junctions. Gap junctions regulate intercellular passage of molecules, including inorganic ions and second messengers, thus achieving electrical coupling of cells via gap junctions. Connexin proteins are the major gap junction protein involved in the electrical coupling of cells. For example Connexin 43 is the major gap junction protein in ventricular myocardium responsible for gap junction intercellular communication. Connexin 43, abbreviated herein as "Cx43", is a protein having structural, regulatory, or biochemical functions associated with gap junctions and electromechanical coupling. Connexins are a whole family of proteins. There are specific connexins for various parts of the heart. Examples of Cx43 useful in the aspects of the invention providing for agent delivery into specified cardiac tissue regions associated with cardiac activation are polypeptide sequences such as human Cx43 (Genbank Accession Nos. XP_027460, XP_027459, XP_004121, P17302, AAD37802, A35853, NP_000156 and AAA52131), mouse Cx43 (Genbank Accession Nos. P23242, P18246, A39802, A36623, NP_034418, CM44640) and exemplary sequences for Rat Cx43 are found at Genbank Accession Nos. P08050, S00532, NP_036699, AAA75194 and 1404339A. Connexin family in the cardiovascular system includes Cx37, Cx40, Cx43, Cx45.

Various references herein to cardiac conduction, signal conduction, or otherwise "conduction" through cardiac tissue are generally intended to mean this propagation related to a resulting contractile wave through cellular tissue, including via gap junctions.

Other examples have been disclosed for locally delivering agents into cells resident in the target cardiac tissue structure that modify the cellular function in-vivo, such as by altering the genetic material within cells to enhance conduction/contraction, such as for example by enhancing cellular expression of certain compounds or agents that cause the intended effect (e.g. DNA material to cause expression or over expression of Cx43 or other such compounds).

There is yet to be a system or treatment method developed that combines cardiac stimulation systems, such as pacemakers or defibrillators, with delivery of conductive agents, such as cell therapy, gene therapy, other modes of tissue engineering, or other conductive agents such as conducting polymers, metals, or combinations thereof (such as injectable solutions or suspensions, e.g. gold, conducting "dust", etc.), in a manner that substantially enhances the artificial stimulation such as pacing or defibrillating of cardiac tissue structures.

In recent years, biventricular septal pacing is an area that has received increasing attention and interest for new product development and research in recent years, in particular as it is intended as a curative measure for the complex and dangerous conditions of bundle block (e.g. bundle of His) and congestive heart failure.

Normal electrical activation of the ventricles generally proceeds as follows. Electrical impulse is initiated from the sinus node, leading to atrial activity passed through the AV node, followed by ventricular activation. The ventricular activation phase includes the following events (typically in the sequence described):

A) Activation of the left septum due to branches of the bundle of His entering the septum higher on the left side of the septum versus the right;
B) Apical depolarization follows early depolarization of the RV (depolarization of the RV occurs quickly due to the thinness of the RV);
C) Depolarization of the lateral wall of the left ventricle; and
D) Late LV depolarization of the base Various different disease states or abnormal conditions can affect this ventricular activation phase of the cardiac cycle. One such example of particular concern is called left bundle branch block ("LBBB"). LBBB alters the entire ventricular depolarization pathway. Depolarization starts from the right side of the septum and progresses toward the left front of the LV. Apical depolarization then occurs.

Biventricular pacing devices and methods have been disclosed that are generally intended to resynchronize LV contractility by activating the LV with a pacing lead, typically via a left-sided (e.g. left ventricle) pacing lead.

Further examples of systems, devices, and methods providing additional background related to the present invention are variously disclosed in the following U.S. Patent Application Publications: US 2002/0035388 to Lindemans et al.; and US 2002/0087089 to Ben-Haim. Other such examples are variously disclosed in the following U.S. Pat. No. 4,399,818 to Money; U.S. Pat. No. 5,103,821 to King; U.S. Pat. No. 5,683,447 to Bush et al.; U.S. Pat. No. 5,728,140 to Salo et al.; U.S. Pat. No. 6,059,726 to Lee et al.; U.S. Pat. No. 6,101,410 to Panescu et al.; U.S. Pat. No. 6,128,535 to Maarse; U.S. Pat. No. 6,151,525 to Soykan et al.; and U.S. Pat. No. 6,238,429 to Markowitz et al. Still other examples are disclosed in the following PCT Patent Application Publications: WO 90/10471 to King; WO 98/02150 to Stokes et al.; WO 98/28039 to Panescu et al.; WO 00/59375 to Sen; WO 01/68814 to Field; WO 02/22206 to Lee; and WO 2/051495 to Ideker et al. The disclosures of all these references listed in this paragraph are herein incorporated in their entirety by reference thereto.

There is still a need for improved cardiac stimulation systems and methods.

There is also still a need to improve conduction within cardiac tissue structures during cardiac stimulation.

There is in particular still a need for a biventricular septal stimulation system and method, such as for biventricular pacing, that provides for artificial cardiac stimulation in combination with delivery of conductive agents in order to enhance the stimulation effect.

There is also still a particular need for septal stimulation system and method that can capture a substantial region of septal tissue, such as in order to provide biventricular pacing in the setting of multiple left bundle branch block.

BRIEF SUMMARY OF THE INVENTION

One object of the invention is to affect cardiac tissue response to stimulation from a cardiac stimulation device such as a pacemaker or defibrillator.

Another object of the invention is to affect contractility or conduction within a region of cardiac tissue in a heart of a patient.

Another object of the invention is to affect ventricular septal function in a heart of a patient.

Another object of the invention is to provide for improved delivery of cardiac stimulation leads and/or agents affecting cardiac contraction or conduction into a ventricular septum.

Another object of the invention is to provide cardiac stimulation to a heart in a patient.

Another object of the invention is to provide cardiac stimulation to a ventricular septum of a patient.

Another object of the invention is to pace a heart of a patient.

Another object of the invention is to defibrillate a heart of a patient.

Another object of the invention is to achieve biventricular pacing or defibrillation of a heart in a patient.

Another object of the invention is to provide both energy delivery and improved tissue response to the delivered energy during cardiac stimulation.

Another object of the invention is to deliver cells into a region of cardiac tissue in a heart of a patient.

One aspect of the invention therefore is a cardiac stimulation system with a cardiac stimulation device assembly and an agent delivery assembly. The cardiac stimulation device assembly comprises a cardiac stimulation device and an energy emitter. The cardiac stimulation device comprises an energy source and is adapted to couple energy from the energy source to the energy emitter. The energy emitter is adapted to be positioned within the patient's body so as to emit energy into a region of cardiac tissue to be stimulated. The agent delivery assembly is adapted to deliver into the region of cardiac tissue an agent that affects a stimulated response in the region to the emitted energy.

One mode of this aspect the agent delivery assembly comprises a delivery catheter. In one embodiment the delivery catheter is a cardiac delivery catheter. In another embodiment, the delivery catheter is a vascular delivery catheter that is adapted to deliver the agent into the region via a blood vessel extending within the septum.

In another mode the agent delivery assembly comprises a needle. In one embodiment of this mode, the needle is a surgical needle. In another embodiment, the agent delivery assembly further comprises a delivery catheter, and the needle is located along the distal end portion of the delivery catheter. In one variation of this embodiment, the delivery catheter is a cardiac delivery catheter. In another variation, the delivery catheter is adapted to be positioned within a blood vessel extending within the septum such that the needle is adapted to puncture through the blood vessel wall and into cardiac tissue of the septum.

Another aspect of the invention is a cardiac stimulation system with a cardiac stimulation device assembly in combination with an agent. The cardiac stimulation device assembly comprises a cardiac stimulation device and an energy emitter. The cardiac stimulation device comprises an energy source and is adapted to couple energy from the energy source to the energy emitter so as to activate the energy emitter. The energy emitter is adapted to be positioned within the patient's body so as to emit energy into a region of cardiac tissue to be stimulated in response to activation from the cardiac stimulation device. The agent is adapted to be located within the region of cardiac tissue and to affect a stimulated response in the region to the emitted energy.

According to one mode, the cardiac stimulation device is a pacemaker device assembly. According to another mode, the cardiac stimulation device is a defibrillation device assembly.

Another aspect of the invention is a system having a cardiac pacemaker that cooperates with a cell therapy system in order to provide cardiac stimulation.

According to one mode, the cell therapy system comprises a volume connexin 43 and a cell delivery catheter that is adapted to deliver the connexin 43 into a region of cardiac tissue to be stimulated by the cardiac pacemaker.

Another aspect of the invention is a cardiac stimulation system with a cardiac stimulation assembly that is adapted to deliver energy into a region of tissue within a heart of a patient so as to stimulate the region, and also with a volume of conductive agent that is adapted to be delivered into the region and to enhance stimulation of the region with the energy delivered by the cardiac stimulation assembly.

According to one mode of this aspect, the cardiac stimulation assembly further includes a delivery member with a proximal and portion and a distal end portion that is adapted to be positioned at a location within a heart of a patient, and also includes an array of extendable electrode assemblies cooperating with the delivery member and that each includes a stimulation electrode that is adjustable to extend from the delivery member at the location and into a unique location relative to the other extendable electrode assemblies within the region of tissue.

In one embodiment of this mode, each of the array of extendable electrode assemblies includes an extendable needle that is adjustable to extend from the distal end portion of the delivery assembly and into cardiac tissue so as to position the respective stimulation electrode at the unique location.

According to one variation of this embodiment, the stimulation electrode of each extendable electrode assembly is integrated with the needle. In another variation, the stimulation electrode of each extendable electrode assembly is adjustable to extend from the respective needle to the unique respective location.

According to other variations, the needle has a curved shape, or may be constructed from a superelastic or shape memory metal alloy such as a nickel-titanium alloy.

In another embodiment, each of the array of extendable electrode assemblies has a relatively pliable tubular body with an inner lumen, and each stimulation electrode is located along the tubular body of the respective extendable electrode assembly. According to this embodiment, each relatively pliable tubular body is adapted to be deflected and steered through the region of tissue so as to place the respective stimulation electrode at the respective unique location.

In one further variation of this embodiment, a moveable stylet is adapted to be moveably engaged within the inner lumen of at least one of the tubular bodies so as to adjust the tubular body to extend from the delivery member and advance through the region of tissue such that the respective stimulation electrode is positioned at the respective unique location. In a further feature, the moveable stylet may be provided with a proximal end portion, and a shaped distal end portion that is torquable within the inner lumen by torquing the proximal end portion proximally and externally of the tubular body so as to deflect and steer the tubular body in order to place the electrode.

According to another embodiment, an anchor is provided and is extendable from the delivery member and adapted to anchor the distal end portion at the location such that the array of extendable electrode assemblies is adapted to be positioned at the respective unique locations along the region of tissue. In one beneficial variation of this embodiment, the anchor is provided also as a stimulation electrode.

According to another embodiment, another stimulation electrode is located at the distal tip of the delivery member.

In a further mode, the cardiac stimulation assembly is a cardiac pacemaker, and in a further embodiment the cardiac pacemaker is a bi-ventricular cardiac pacemaker.

According to another mode of the present aspect, the conductive agent includes living cells, and in further embodiments the cells include at least one of myoblasts, fibroblasts, or stem cells. In another regard, the living cells are of a type that are adapted to express a connexin at gap junctions with cardiac cells in the region of tissue, and in more particular beneficial variation are adapted to express connexin 43 at the gap junctions, and still further are beneficially genetically modified to over-express production of connexin 43.

In another mode, the conductive agent includes an injectable preparation of a conductive non-living material that is adapted to enhance electrical conduction in the region, such as a conductive metal.

According to another mode, a septal perforator delivery assembly is included in the system and is adapted to couple the cardiac stimulation assembly to the region of tissue via at least one septal perforator vessel, and also to deliver the volume of conductive agent to the region via the at least one septal perforator vessel.

In another mode, a transcardiac delivery member is provided for delivery of the stimulation assembly and conductive agent via a cardiac chamber, such as the right atrium.

Another aspect of the invention is a cardiac stimulation system with a cardiac stimulator assembly with an energy source, and an energy emitter that is adapted to be coupled to the energy source and to be positioned within a region of a heart of a patient to be stimulated, and that also includes means for enhancing stimulation of the region with the energy from the energy emitter.

Another aspect of the invention is a cardiac stimulation system with a conductive agent delivery system that includes a source of conductive agent and a delivery assembly that is adapted to deliver a volume of conductive agent from the source and into a region of a heart in a patient, and also with a means for delivering energy to at least a portion of the region. The volume of conductive agent is adapted to enhance stimulation of the region with the energy from the means for delivering energy.

Another aspect of the invention is a cardiac stimulation assembly with an elongate body having a proximal end portion, a distal end portion that is adapted to be positioned at least in part at a location within a heart of a patient, and a delivery lumen extending at least in part along the distal end portion. This assembly further includes a means for delivering energy into a region of tissue within the heart of the patient, as well as a means for enhancing stimulation of the region of tissue from energy delivered from the means for delivering energy. Furthermore, the means for delivering energy and means for enhancing stimulation are adapted to cooperate with the elongate body.

Another aspect of the invention is a cardiac stimulation assembly with an elongate body having a proximal end portion, a distal end portion that is adapted to be positioned at least in part at a location within a heart of a patient, and a lumen extending at least in part along the distal end portion, and also with an energy delivery assembly and a volume of conductive agent. The energy delivery assembly has an energy emitter that is coupled to the elongate body and is adjustable to extend from the distal end portion and into a region of tissue within the heart when the distal end portion is at the location, and also has an energy lead that is adapted to couple to the energy emitter and also to a source of energy along the proximal end portion when the energy emitter is in the second position. The volume of conductive agent is coupled to the lumen and is adapted to be delivered through the lumen into the region of tissue when the distal end portion is at the location and the energy emitter is in the second position.

Another aspect of the invention is a cardiac stimulation system with a cardiac stimulation device and a volume of cells that are adapted to over-express connexin 43. The cardiac stimulation device has an elongate body with a proximal end portion, a distal end portion, and a cardiac stimulation electrode along the distal end portion. The cardiac stimulation device and volume of cells are adapted to cooperate so as to stimulate a region of tissue within a heart of a patient.

Another aspect of the invention is a cardiac stimulation assembly with an elongate body, an energy delivery assembly, and a volume of conductive agent. The elongate body has a proximal end portion, a distal end portion that is adapted to be positioned at least in part at a location within a heart of a patient, and a lumen extending at least in part along the distal end portion. The energy delivery assembly has an energy emitter that is coupled to the elongate body and is adjustable to extend from the distal end portion and into a region of tissue within the heart when the distal end portion is at the location. This assembly also has an energy lead that is adapted to couple to the energy emitter and also to a source of energy along the proximal end portion when the energy emitter is extended into the region of tissue. The volume of conductive agent is coupled to the lumen and is adapted to be delivered at least in part through the lumen into the region of tissue when the distal end portion is at the location and the energy emitter is extended into the region of tissue.

Another aspect of the invention is a cardiac stimulation assembly with an elongate body, an energy delivery assembly, and an anchor. The elongate body has a proximal end portion and a distal end portion that is adapted to be positioned at least in part at a location within a heart of a patient. The energy delivery assembly has a plurality of energy emitters. Each energy emitter is coupled to the elongate body and adjustable to extend from the distal end portion and into a unique respective position relative to the other energy emitters within a region of tissue within the heart when the distal end portion is at the location. Each energy emitter is also adapted to couple to a source of energy when the respective energy emitter is in the second position within the region of tissue. The anchor is adapted to anchor the distal end portion at the location within the heart.

Another aspect of the invention is a cardiac stimulation assembly with an elongate body, an energy delivery assembly, and a cardiac stimulation energy source. The elongate body has a proximal end portion, a distal end portion that is adapted to be positioned at least in part at a location within a heart of a patient, and a delivery lumen extending at least in part along the distal end portion. The energy delivery assembly has a plurality of energy emitters. Each energy emitter is coupled to the elongate body and adjustable to extend from the distal end portion and into a unique respective position relative to the other energy emitters within a region of tissue within the heart when the distal end portion is at the location. Each energy emitter is also adapted to couple to a source of energy via the proximal end portion when the respective energy emitter is extended into the region of tissue. The cardiac stimulation energy source is adapted to couple to each of the energy emitters and to energize each energy emitter so as to emit energy into the region of tissue. Accordingly, the energy emitters at each unique respective position within the region of tissue are adapted to stimulate the region of tissue.

Another aspect of the invention is a cardiac stimulation device with an elongate body, a needle, and an energy emitter. The elongate body has a proximal end portion, a distal end portion, and a passageway located at least in part along the distal end portion. The needle has a shank with a distal tip and an inner lumen. The energy emitter that is adapted to be coupled to an energy source. Further to this aspect, the distal end portion of the elongate body is adapted to be positioned at a location within a heart of a patient, and the needle is adapted to be coupled to the passageway and is adjustable between a first position located at least in part within the passageway and a second position that extends at least in part from the passageway and into a region of tissue within the heart when the distal end portion is at the location. Furthermore, the energy emitter is coupled to the inner lumen of the needle and is adjustable to extend from the needle into the region of tissue.

Another aspect of the invention is a bi-ventricular cardiac stimulation system that includes an array of stimulation electrodes. Each electrode of the array is adapted to be positioned at a unique location relative to the other stimulation electrodes within an intra-ventricular septum of a heart of a patient, such that the array of positioned electrodes is adapted to form a pattern that defines a region of tissue within the septum. Furthermore, the pattern and region defined thereby comprises such sufficient area so as to stimulate at least one-quarter of the septum, and in further embodiments may be sufficient to provide artificial stimulation to at least one-third or even as much as one-half or more of the septum.

Another aspect of the invention is a cardiac stimulation system with a bi-ventricular cardiac stimulation energy source and a septal stimulation device with an elongate body having a proximal end portion and a distal end portion with an array of extendable cardiac stimulation electrodes. The distal end portion is adapted to be positioned at a location within a heart of a patient associated with a ventricular septum. Each of the extendable cardiac stimulation electrodes is adjustable to extend from the distal end portion so as to be positioned at a unique respective location relative to the other extendable cardiac stimulation electrodes within a region of tissue within the ventricular septum. Each of the extendable stimulation electrodes is also adapted to be coupled to the bi-ventricular cardiac stimulation energy source. Accordingly, by positioning the distal end portion of the elongate body at the location, positioning each of the extendable cardiac stimulation electrodes at each respectively unique location within the region of tissue, and coupling each extendable cardiac stimulation electrode to the bi-ventricular cardiac stimulation energy source, the array of electrodes is adapted to substantially stimulate the region of tissue be energizing each electrode of the array with the energy source to emit current from its respectively unique location within the region.

The invention further includes other aspects providing methods of treatment as follows.

Another aspect of the invention is a method comprising: delivering a volume of cells into a region of cardiac tissue; and stimulating the region of cardiac tissue with a cardiac stimulation device assembly.

One further mode of this aspect comprises: pacing the heart of the patient from the region of cardiac tissue containing the volume of cells.

Another mode of this aspect comprises: providing the cells in a condition wherein connexin 43 is expressed.

A further embodiment of this mode comprises: providing the cells in the condition such that connexin 43 is overexpressed more than resident cardiac cells in the region.

Another aspect of the invention is a method comprising: delivering a volume of cells within a ventricular septum of a patient sufficient to enhance response of the septum to stimulus from a pacemaker or defibrillator.

Another aspect is a method comprising: using the vasculature of a ventricular septum in a patient to deliver a volume of an agent into the septum that enhances the response of the tissue in the septum to stimulus from a cardiac stimulation device.

Another aspect of the invention is a method comprising: using the vasculature of a ventricular septum in a patient to deliver a volume of an agent into the septum that enhances the cardiac contraction or conduction along the septum.

Another aspect of the invention is a method comprising: using the vasculature of a ventricular septum in a patient to deliver cardiac stimulator leads into the septum for use in either pacing or defibrillating the heart via the septum.

Another aspect of the invention is a method comprising: emitting stimulating energy from an energy emitter over a substantial portion of the ventricular septum.

Another aspect of the invention is a method comprising: implanting an array of energy emitters at unique locations within a ventricular septum of a patient such that an area bound and by such energy emitters comprises a substantial portion of the septum.

One mode of this method further comprises: simultaneously emitting energy from each of the implanted energy emitters.

Another mode of this method further comprises: implanting an anchor into the septum; and extending from the anchor at least one of the energy emitters.

Another mode of this method further comprises: implanting an anchor into the septum; and extending from the anchor each of the energy emitters.

Another mode of this method further comprises: coupling the implanted energy emitters with a pacemaker.

Another mode of this method further comprises: coupling the implanted energy emitters with a defibrillator.

Another mode of this method further comprises: emitting electrical current from each of the energy emitters.

Another mode of this method further comprises: delivering each of the energy emitters to the unique location through a needle.

Another mode of this method further comprises: advancing an array of needles into the septum; and delivering each energy emitter to its respective unique location within the septum through a unique one of the needles.

Another mode of this method further comprises: positioning multiple ones of the array of energy emitters on a delivery member; advancing the delivery member into the septum such that each of the energy emitters positioned on the delivery member is located at its respective unique location.

Another aspect of the invention is a method for stimulating a region of a heart in a patient by providing a cardiac stimulation assembly, providing a conductive agent delivery system, delivering energy to a location associated with the region of the heart to be stimulated with the cardiac stimulation system, and delivering a volume of conductive agent from the conductive agent delivery system to the region of the heart. Further to this method aspect, the volume of conductive agent enhances stimulation of the region of the heart with the energy being delivered to the location.

Another aspect of the invention is a method for providing bi-ventricular stimulation to a heart of a patient by: providing an array of cardiac stimulation electrodes, positioning a distal end portion of a delivery member against a portion of an intra-ventricular septum of the heart, and extending the array of cardiac stimulation electrodes from the distal end portion of the delivery member and into the intra-ventricular septum such that each cardiac stimulation electrode is positioned at a unique location relative to the other cardiac stimulation electrodes within a region of tissue of the intra-ventricular septum.

Another aspect of the invention is a method for manufacturing a bi-ventricular cardiac stimulation system for providing bi-ventricular stimulation to a heart of a patient. This method is performed by: providing a bi-ventricular stimulation device having an elongate body with a proximal end portion, a distal end portion that is adapted to be positioned at a location within a ventricle, a stimulation electrode located at a position along the distal end portion so as to be electrically coupled to a region of tissue of a septum of the heart when the distal end portion is at the location, and a passageway extending at least along the distal end portion. This method further includes: loading a volume of cells within the passageway of the bi-ventricular stimulation device, wherein the cells are adapted to over-express connexin-43 or an analog, derivative, or biological equivalent thereof.

Another aspect of the invention is also method for manufacturing a cardiac stimulation system for providing cardiac stimulation to a heart of a patient. This method includes providing a cardiac stimulation device having an elongate body with a proximal end portion, a distal end portion that is adapted to be positioned at a location within the heart, an array of extendable cardiac stimulation electrodes that are each adapted to be extended from the distal end portion at the location so as to be positioned at a unique location relative to the other extendable cardiac stimulation electrodes within a region of tissue within the heart, and a passageway extending at least along the distal end portion. This method further includes: loading a volume of cells within the passageway, wherein the cells are adapted to enhance electrical stimulation of the region of tissue from the array of extendable electrodes.

Another aspect of the invention is a method for stimulating a region of a septum in a heart of a patient by: delivering at least one cardiac stimulation electrode into at least one septal perforator vessel within an intra-ventricular septum of the heart, delivering a volume of conductive agent to a region of tissue within the septum associated with the septal perforator vessel, and, after the volume of conductive agent is delivered into the region, stimulating the region of tissue with the at least one cardiac stimulation electrode.

Another aspect of the invention is a method for providing bi-ventricular stimulation to a heart in a patient by stimulating a region of tissue that comprises at least one-quarter of the inter-ventricular septum, and in further modes at least one-third, or even one-half, and up to as much as all of the septum.

Another aspect of the invention is a method for stimulating a region of a heart in a patient by delivering a volume of cells into the region that are adapted to over-express connexin-43 or an analog, derivative, or biologic equivalent thereof, and providing an electrical stimulus to the region.

The various aspects, modes, embodiments, variations, and features just described are considered to be independently beneficial without requiring combination with the others, though the invention further contemplates the benefits from their various combinations as may be made by one of ordinary skill based upon the totality of this disclosure.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the embodiments generally shown in FIGS. 1 through 15. It will be appreciated that the apparatus may vary as to configuration and as to details of the parts, and that the method may vary as to the specific steps and sequence, without departing from the basic concepts as disclosed herein.

In patients with impaired conduction via the bundle branches (especially left bundle branch block or "LBBB"), capturing more of the septum with multiple leads coupled with an injectable conductor will enable more of the septum to be activated therefore enabling depolarization of the LV and improved synchronization.

The present invention contemplates various approaches to achieving the objects of the invention, in particular as they relate to delivering agents into regions of cardiac tissue in order to affect the conduction and enhance response to electrical stimulation there.

Figure 3:
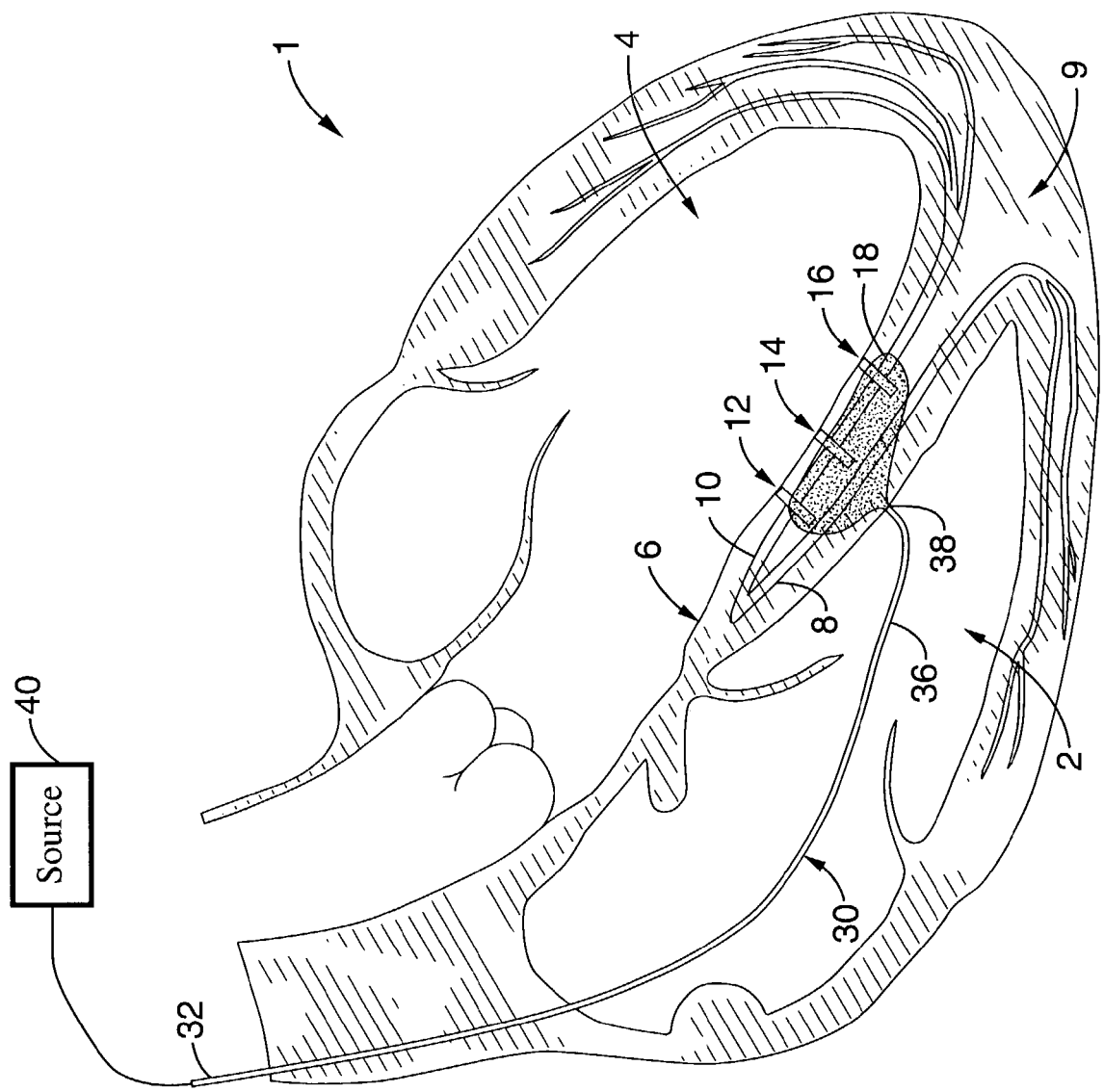
FIG. 3 shows a similar cross-section of the heart shown in FIGS. 1 and 2, and shows a subsequent mode of using the invention wherein an agent affecting cardiac conduction is delivered into a cardiac tissue region related to the multiple left bundle blocks.
Figure 7:
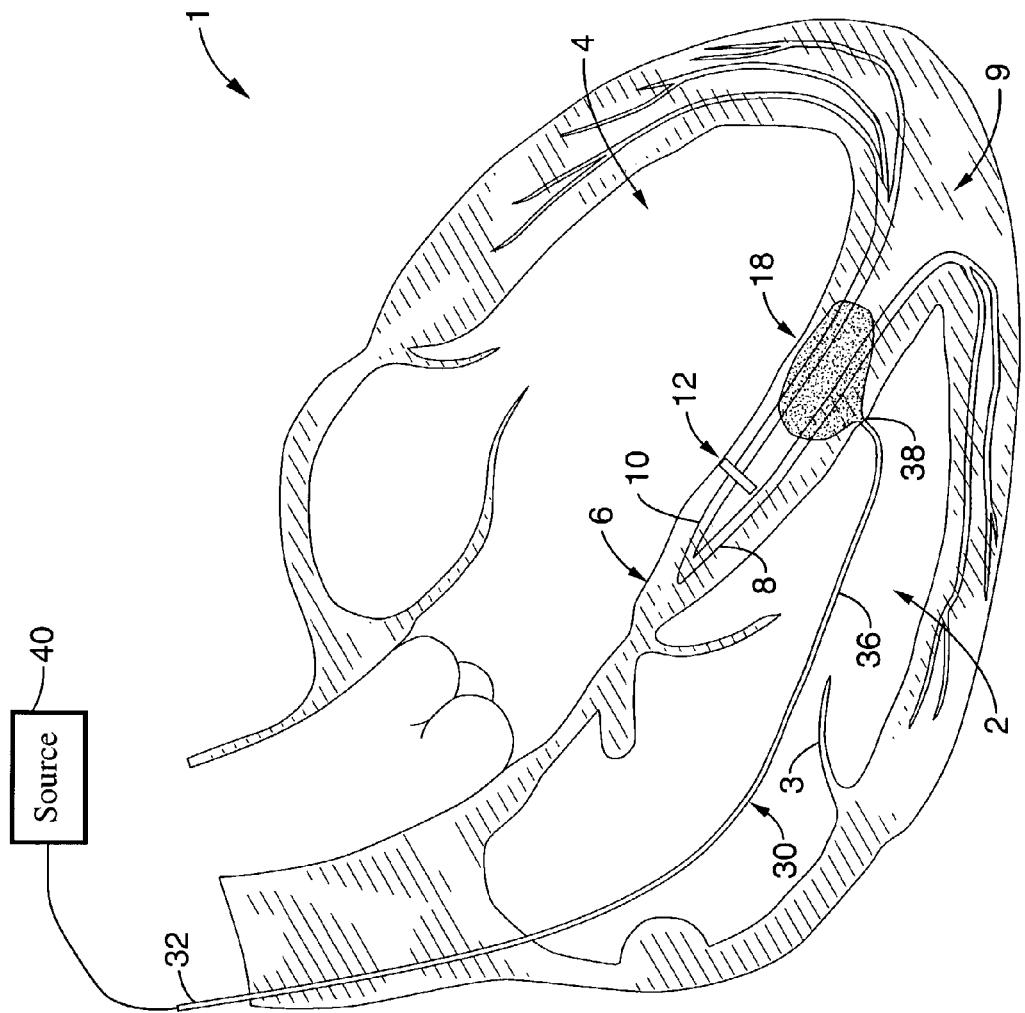
FIG. 7 shows a similar cross-section of the heart shown in FIGS. 5 and 6, and shows a subsequent mode of using the invention wherein an agent affecting cardiac conduction is delivered into a cardiac tissue region related to the left bundle block.

In one regard, an agent that is adapted to enhance conduction of a cardiac signal (i.e. biological conductor, conducting metals, conducting polymers, etc) is delivered into the myocardial septum, such as for example being injected via a percutaneous, transcardiac approach such as shown via a transcardiac delivery catheter in FIGS. 3 and 7. Various conventional or other delivery systems may be suitable for such delivery, such as for example those delivery catheters and systems: the "Noga" system developed by Johnson & Johnson, the "Myocath" device and system developed by BioHeart, Inc.; the "Stilleto" catheter device and system developed by Boston Scientific Corporation; and at least one other catheter device and system commercially developed by "BioCardia".

In another regard, a pacemaker lead system may include delivery features, e.g. lumens, through which such agent may be delivered. In this regard, while such pacemaker lead may require increased profile to accommodate an agent delivery lumen, benefits include the substantial benefit of knowing that the conductor agent is delivered in the proximity of the source of energy emission for depolarization.

In addition to the specific embodiments herein shown or described, other agent deliver devices or methods may be suitable to accomplish the intended objects of the invention as herein contemplated, as is apparent to one of ordinary skill based at least in part upon this disclosure.

Notwithstanding other embodiments elsewhere herein shown and described, and variations and modifications as would be apparent to one of ordinary skill, the following embodiments are considered highly beneficial in particular respect, though not limited to, biventricular pacing: delivering a substance or agent affecting cardiac conduction through a delivery system; delivering a substance or agent affecting cardiac conduction through a pacemaker lead; and providing extendable electrode structures with multiple leads that are adapted to span a substantial area of the ventricular septum for more efficient pacing there.

With respect to the extendable electrode aspect of the invention, according to one beneficial embodiment, microfilaments are generally used to extend and increase the electrode surface area/volume in which to electrically stimulate the myocardium. The use of the extended electrode will allow for a greater amount of the myocardium to be stimulated thus synchronizing electromechanical contraction of the heart. The novel electrode array and related cardiac stimulation system is considered particularly useful in patients with bundle branch block, such as illustrated in the Figures, as well as patients suffering from congestive heart failure.

Accordingly, it will be seen that this invention may be used for particular benefit in stimulating the ventricular septum, such as is illustrated by reference to certain particular, illustrative embodiments in the Figures as follows.

By general reference to the Figures, a heart 1 is shown in various cross-sectioned views to include a right ventricle 2, bi-cuspid valve 3, left ventricle 4, inter-ventricular septum 6 that includes right and left bundles 8, 10, respectively, and an apex 9.

Figure 1:
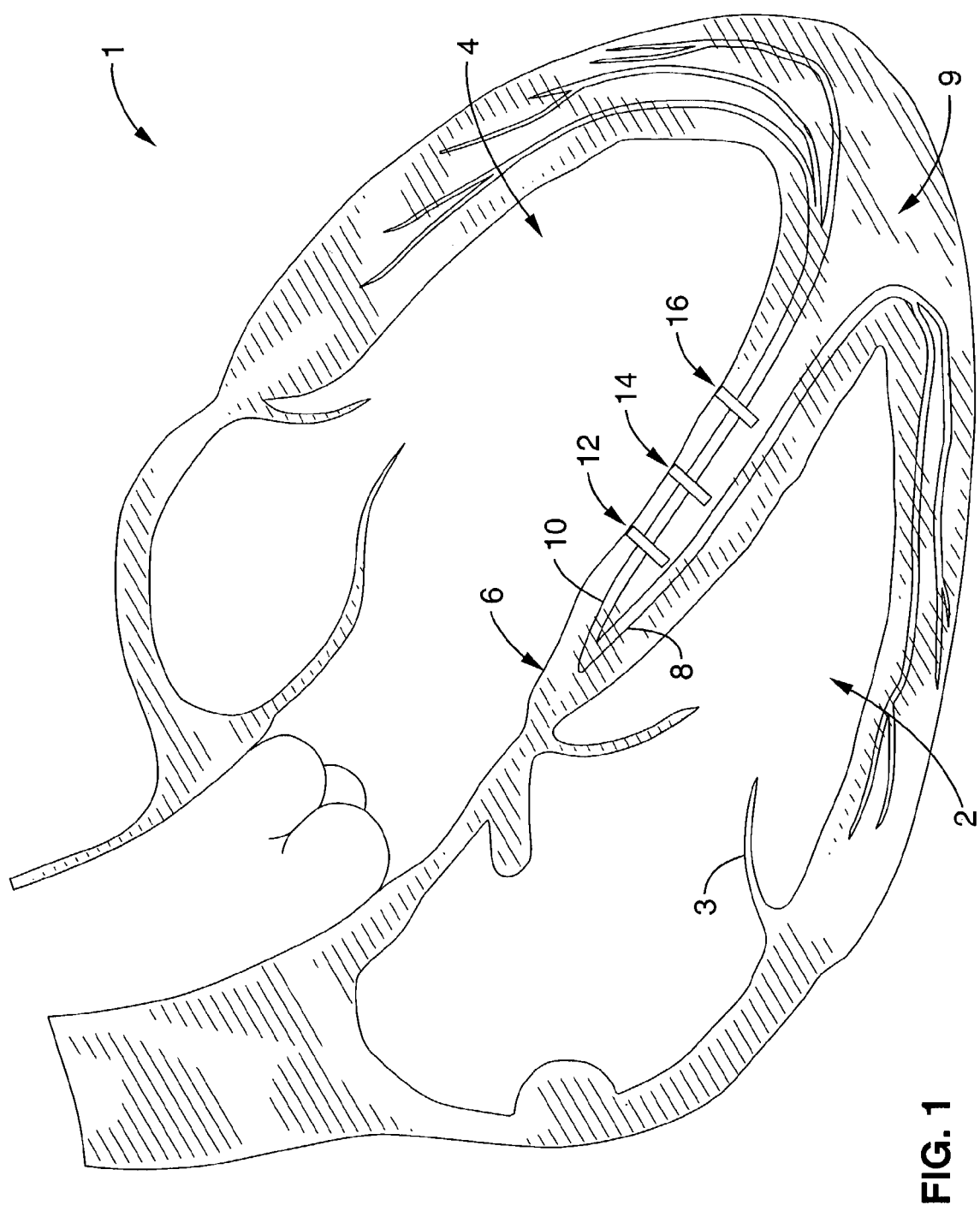
FIG. 1 shows a cross-section of a heart with multiple regions of left bundle block indicated by arrows before treatment according to the systems and methods of the present invention.
Figure 2:
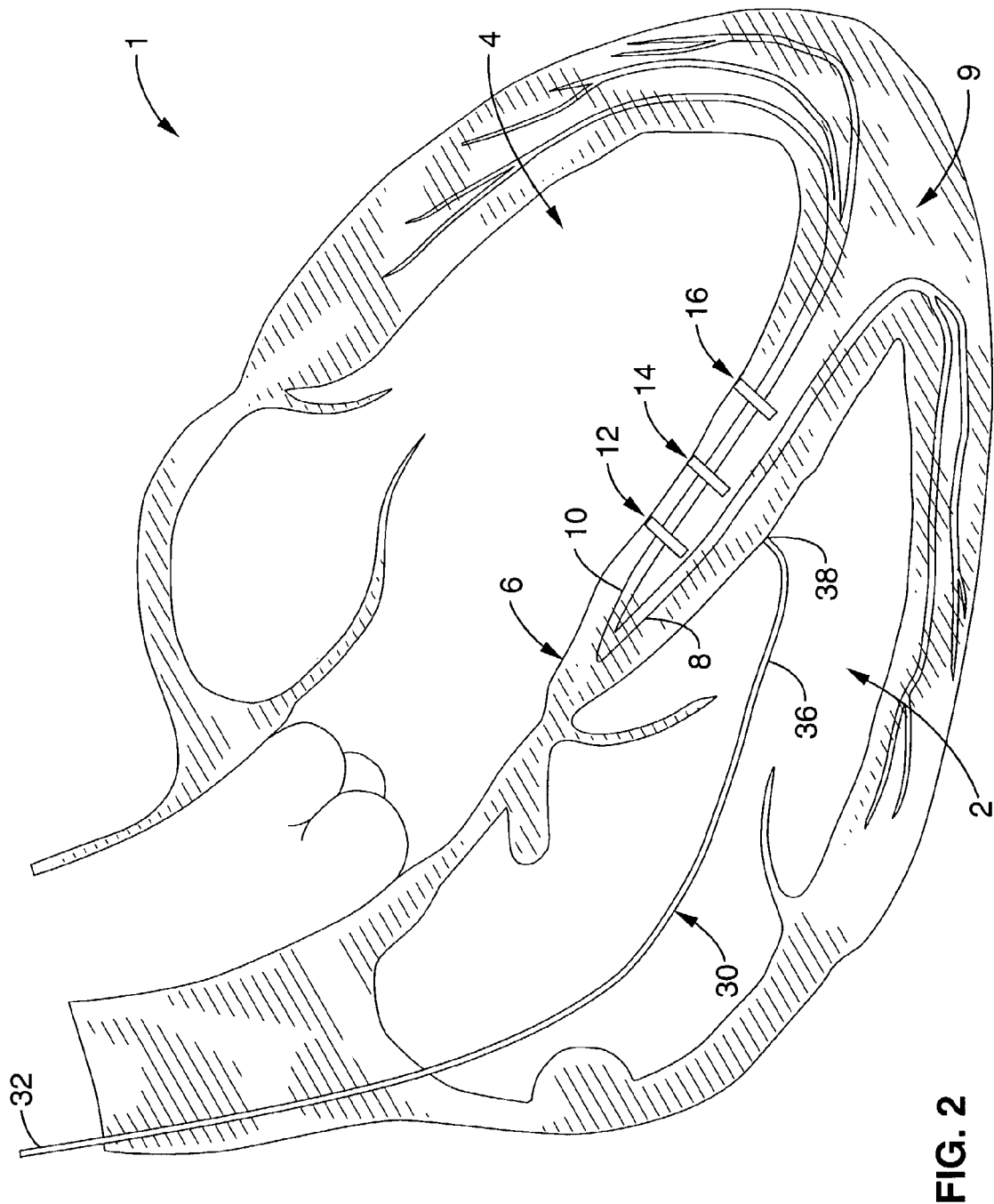
FIG. 2 shows a similar cross-section of the heart with multiple regions of left bundle block shown in FIG. 1, and shows one mode of the invention with a delivery catheter positioned against the septum in the right ventricle.
Figure 4:
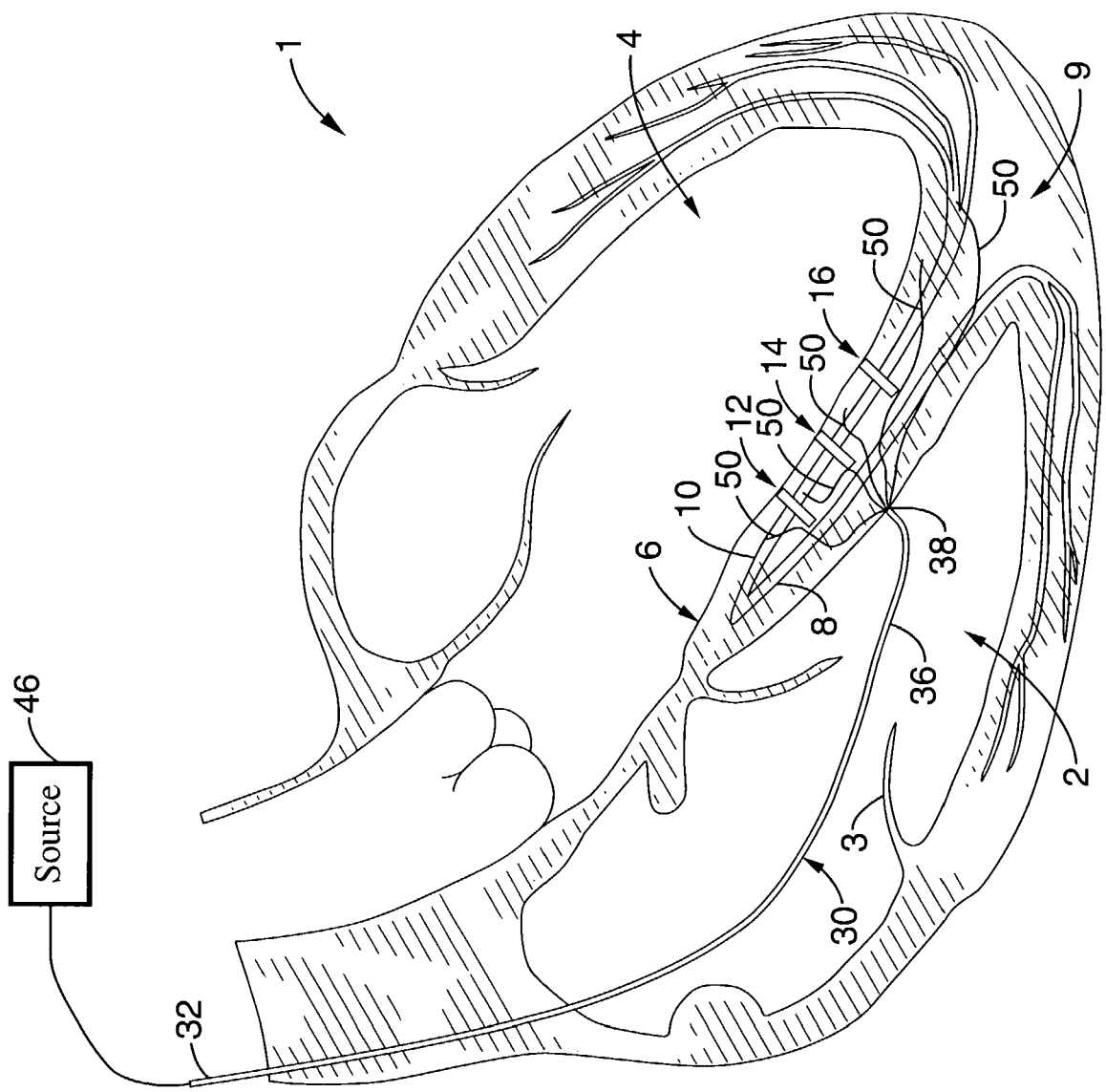
FIG. 4 shows a similar cross-section of the heart shown in FIGS. 1-3, except showing another mode implanting an array of energy emitters into a cardiac tissue region related to the multiple left bundle blocks.

As shown by reference to FIGS. 1-4, patients having hearts with multiple regions of left bundle block are particularly well treated by use of the present invention. As indicated by arrows in FIG. 1, the multiple areas of block 12, 14, 16 are shown and create a particular challenge for pacing from a conventional, single electrode approach. Particular modes of using the present embodiment of this invention in this multiple left bundle block setting are illustrated in FIGS. 2-4.

As shown in FIG. 2, an agent delivery catheter 30 is shown with a proximal end portion 32 and distal end portion 36 that includes a distal tip 38. Distal end portion 36 is delivered into the right ventricle 2 by manipulating proximal end portion 32 externally of the body via a percutaneous, translumenal approach through the venous system, and then into the ventricle across the right atrium via the bicuspid valve 3. The distal tip 38 of the distal end portion 36 of the delivery catheter 30 is then positioned within the right ventricle 2 against the septum 6. A source of agent 40 is coupled to a proximal end portion of the delivery catheter, as shown schematically in FIG. 3. A volume of the conductive agent 18 from the source is then delivered through a delivery lumen (not shown) within the delivery catheter 30, through a distal port located on the distal tip 38 of the delivery catheter 30, and into a region of cardiac tissue associated with the multiple left bundle blocks, as shown in FIG. 3. This may be accomplished using pressure alone, though in certain beneficial embodiments (e.g. described below) a needle tip, either integral with the delivery catheter or slideably disposed therein, is used to inject the agent into the tissue. Where such a separate cooperating needle is used, the internal bore of the needle will be coupled proximally with the source of agent, as will be further developed below.

With respect to septal electrode aspects of the invention, a percutaneous, translumenal delivery catheter 30 may also be used for delivery of such cardiac stimulation assembly to the region of septum to be stimulated, as shown in FIG. 4. Also shown in that FIG. 4, a plurality of electroded members 50 are delivered through the delivery catheter 30, which electroded members 50 may be splines, filaments, or other types of leads coupled to electrodes, which are further coupled to an electrical energy source 46 proximally for electrical current emission from members 50 into the septal tissue. By providing these leads 50 in an array with electrodes positioned to span a sufficiently wide area of the septum as shown, their coordinated current emission allows for improved stimulation over a region of tissue spanning a wide area well suited for providing proper cardiac conduction from such an area of multiple blocks, such as blocks 12, 14, 16 shown in the illustrative embodiment in FIG. 4.

The electrode leads 50 may include filaments, splines or other types of suitable structures to provide requisite mechanical support for delivery and also conduct signals to the electrodes. The leads 50 may be advanced through the cardiac tissue according to various techniques and tools as would be apparent to one of ordinary skill. In one example, the distal tips of the leads are sharpened allowing the leads to be advanced simply as needles mechanically pushing through tissue. In another example, a separate extendable delivery device such as deployable needle is extended from the anchor point to the location to deliver the lead, and the lead is delivered to that location through that needle. In other alternative or combined examples (not shown), an ablative energy source may be coupled between the leads and the tissue such that the leads or splines ablate their way through the cardiac tissue for deployment.

Such stimulation is provided by coupling the electroded lead members 50 with a source of stimulating energy 46, as also shown in FIG. 4. This may be for example a pacemaker or defibrillator, which may be of particular type or style to meet the particular needs for stimulation at the location in the heart chosen for the therapy according to the invention. In the specific beneficial setting of the present embodiments for stimulating a septum, the energy source 46 may be a bi-ventricular pacemaker assembly with appropriate software and hardware incorporated therein to provide the appropriate stimulus there. Further more detailed examples of such energy sources contemplated for use with the present invention include without limitation: a dual chamber pacer under the product name "Kapp 900" (model #KDR901), intracardiac defibrillator (ICD) under the product name "Marquez DR" (model #7274), and bi-ventricular ICD under the product name "Insync ICD" (model #7272), all commercially available from Medtronic Device Corporation; and Guidant DDD under the product name "Insignia" (model #1298), an ICD under the product name "Prism II" (e.g. model #1861); and Guidant BiV (Renewal, model #H135), all commercially available from Guidant Corporation.

As elsewhere herein described, an array of electroded members 50 may also be delivered subsequent to, before, or simultaneous with delivery of agent 18 for enhancing conduction of the stimulated septal region. For example, the embodiment of FIGS. 3 and 4 would be combined. In this highly beneficial setting, the wide area stimulation from the array of electroded members 50 is further combined with the enhanced conduction due to the agent 18 in the area to give optimal results.

Figure 5:
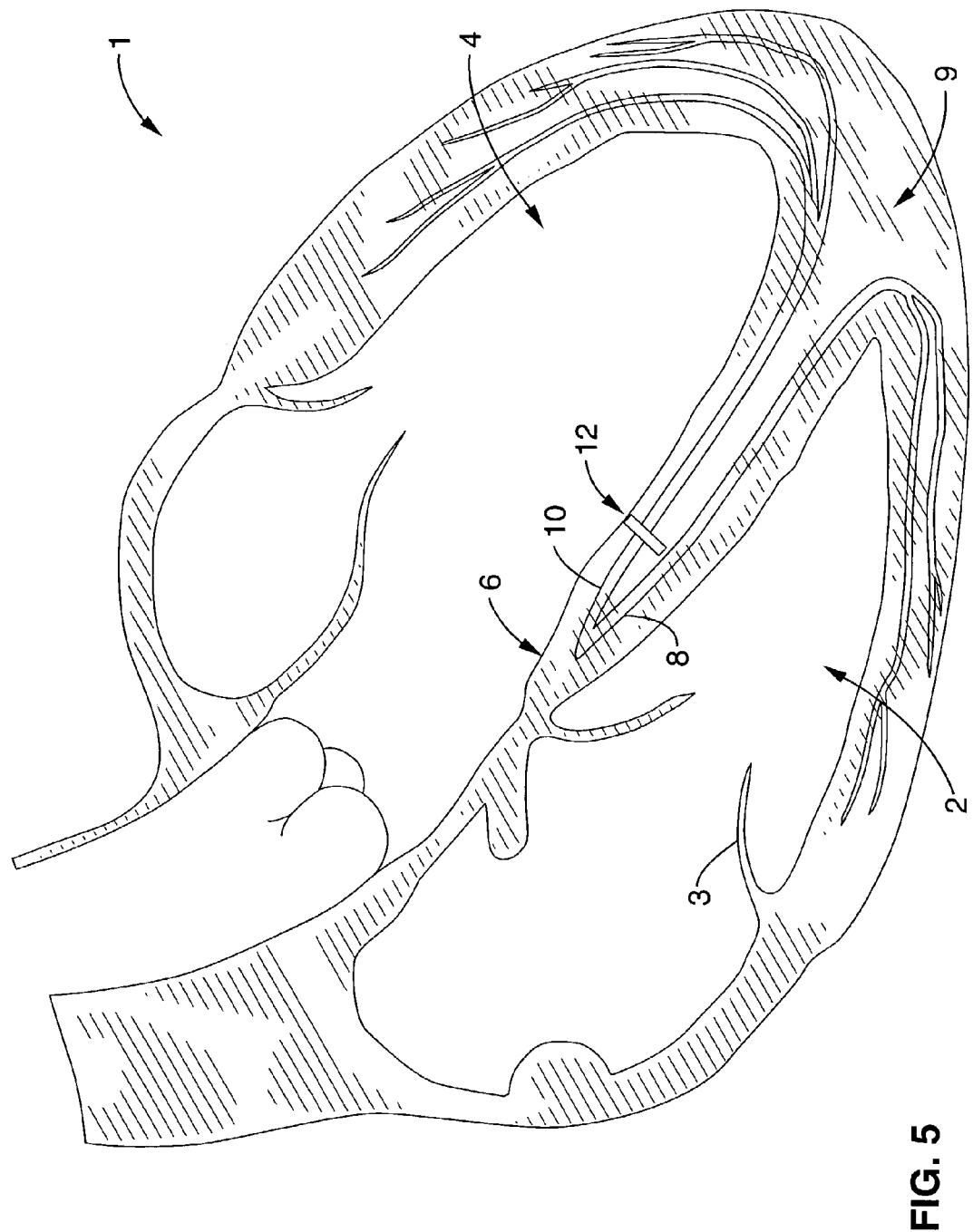
FIG. 5 shows a cross-section of a heart with a left bundle block similar to that shown in FIG. 1, except showing the heart with a localized, single region of left bundle block as indicated by an arrow.
Figure 6:
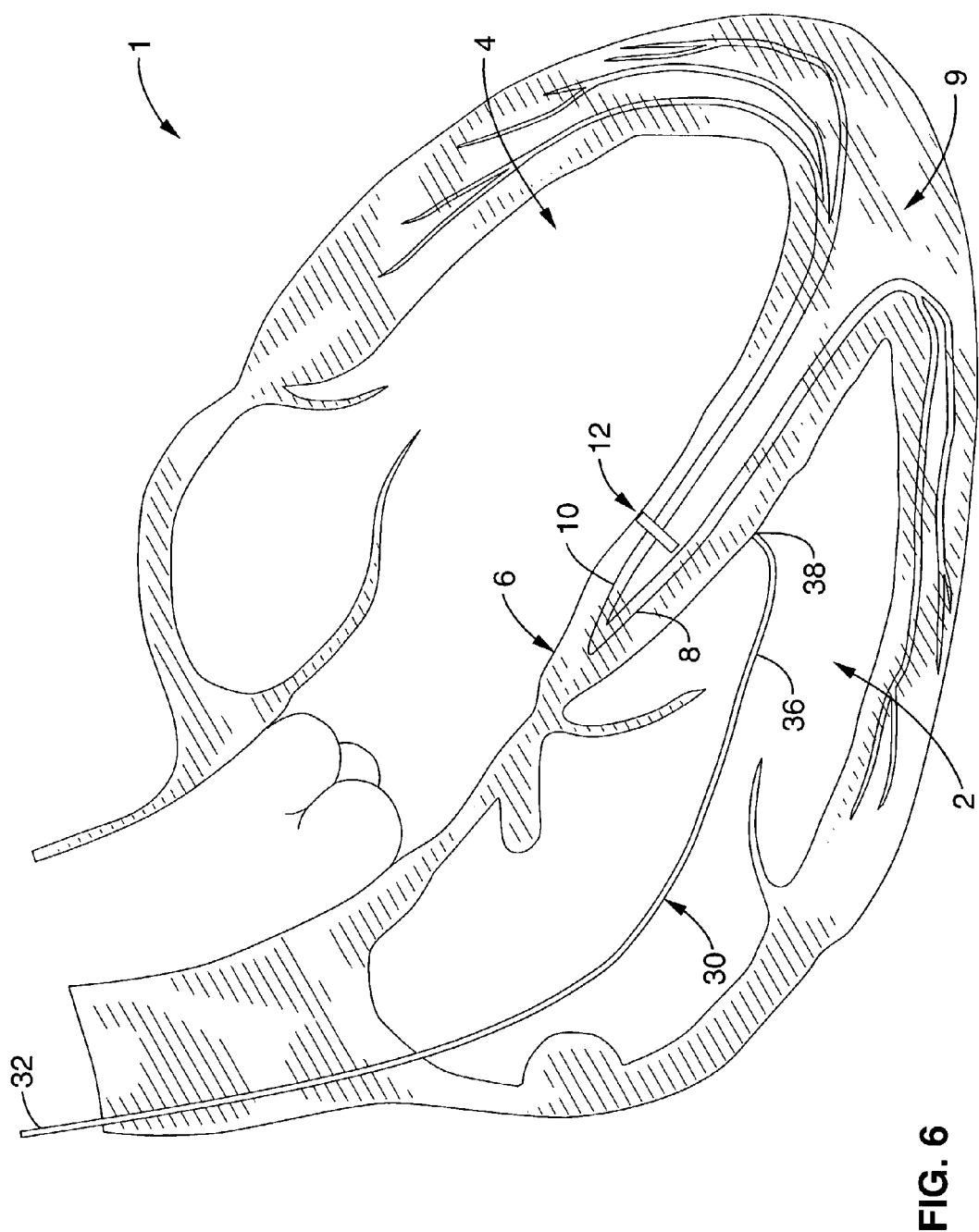
FIG. 6 shows a similar cross-section of the heart with the localized region of left bundle block shown in FIG. 5, and shows one mode of the invention with a delivery catheter positioned against the septum in the right ventricle.

In another regard, the embodiments elsewhere herein described are also useful for other arrhythmic conditions in the septum or elsewhere, such as for example in the setting of a more focal region of local left bundle block as shown by reference to block 12 for illustration according to the agent 18 delivery embodiment in FIGS. 5-7.

Figure 8C:
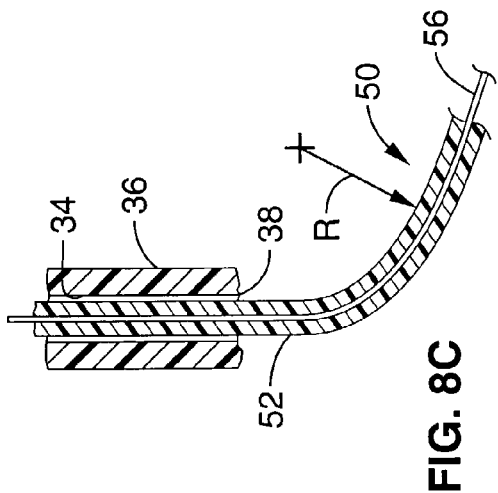
FIG. 8C shows a schematic partially cross-sectioned view of a particular embodiment for delivering an electrode such as according to the array assembly shown in FIGS. 8A-B.
Figure 8A:
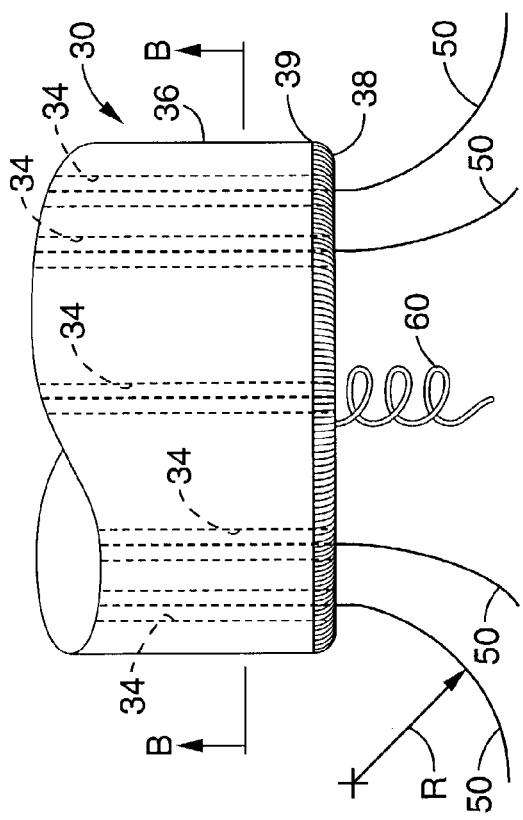
FIG. 8A shows a side view, including some internal structures, of a distal end portion of an extendable electrode array assembly according to the invention.
Figure 8B:
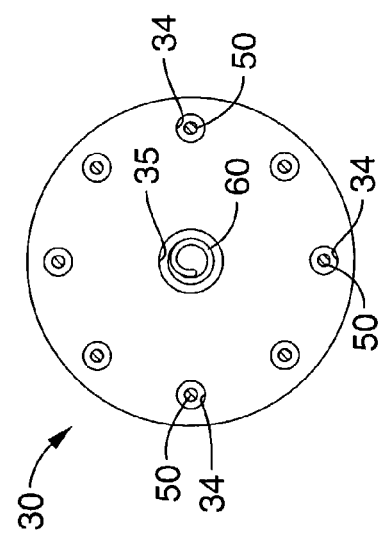
FIG. 8B shows a transverse cross-section taken along lines B-B in FIG. 8A.

A further highly beneficial embodiment for a cardiac stimulation assembly to be used according to the invention is shown in FIGS. 8A-C. More specifically, delivery catheter 30 includes an array of lumens or passageways 34, including respective ones that are circumferentially spaced around a central one. The circumferentially spaced lumens 34 each houses a lead of a respective electroded member 50, whereas the central lumen 34 houses another electroded lead 60 that forms a screw-shaped anchor adjustable in and out of that central lumen 34 for delivery to and then anchoring into the septum, respectively. Furthermore, the circumferentially spaced electroded members 50 are shown according to a still more detailed embodiment in FIG. 8C to include a pre-shaped needle member 52, which may be made of nickel-titanium alloy or other superelastic, shape memory, or other suitable material, that is adapted to be housed within its respective lumen 34 during delivery of tip 38 to abut a septal wall, and then extendable from lumen 34 to advance into the septal wall. Further shown is an extendable electrode member 56 that is further adjustable in and out of needle member 52. Yet a further ring electrode is shown at tip 38 of delivery catheter 30, which may be used to assist in mapping to find the optimal place for placement of the stimulation electrodes, and/or for additional surface area for stimulation as a stimulation electrode.

Though the specific configurations shown in FIGS. 8A-C are considered beneficial, the various features such as number, placement, or specific types of elements are illustrative and other suitable substitutes may be made. For example, other numbers and corresponding placements for the circumferentially spaced electroded members 50 may be used, generally desiring 2 or more electroded members 50 according to the present embodiment, and generally between 2 to 4 electroded members 50 may be optimal for many circumstances. In another example shown in FIG. 9, a moveable stylet 58 is moveable within a passageway of an electroded member 50 that includes a pliable shank 52 with an electrode 54 at its tip. The moveable stylet 58 is adapted to assist shank 52 during advancement through septal wall tissue to the desired location for positioning electrode 54 for stimulation. Such features may be provided instead of use of the needle assembly shown and described by reference to FIG. 8C, or various modifications may be made to combine various aspects between those two approaches, including for example for a particular electroded assembly 50, or by providing one such assembly with one design and one or more according to the other design.

Figure 10:
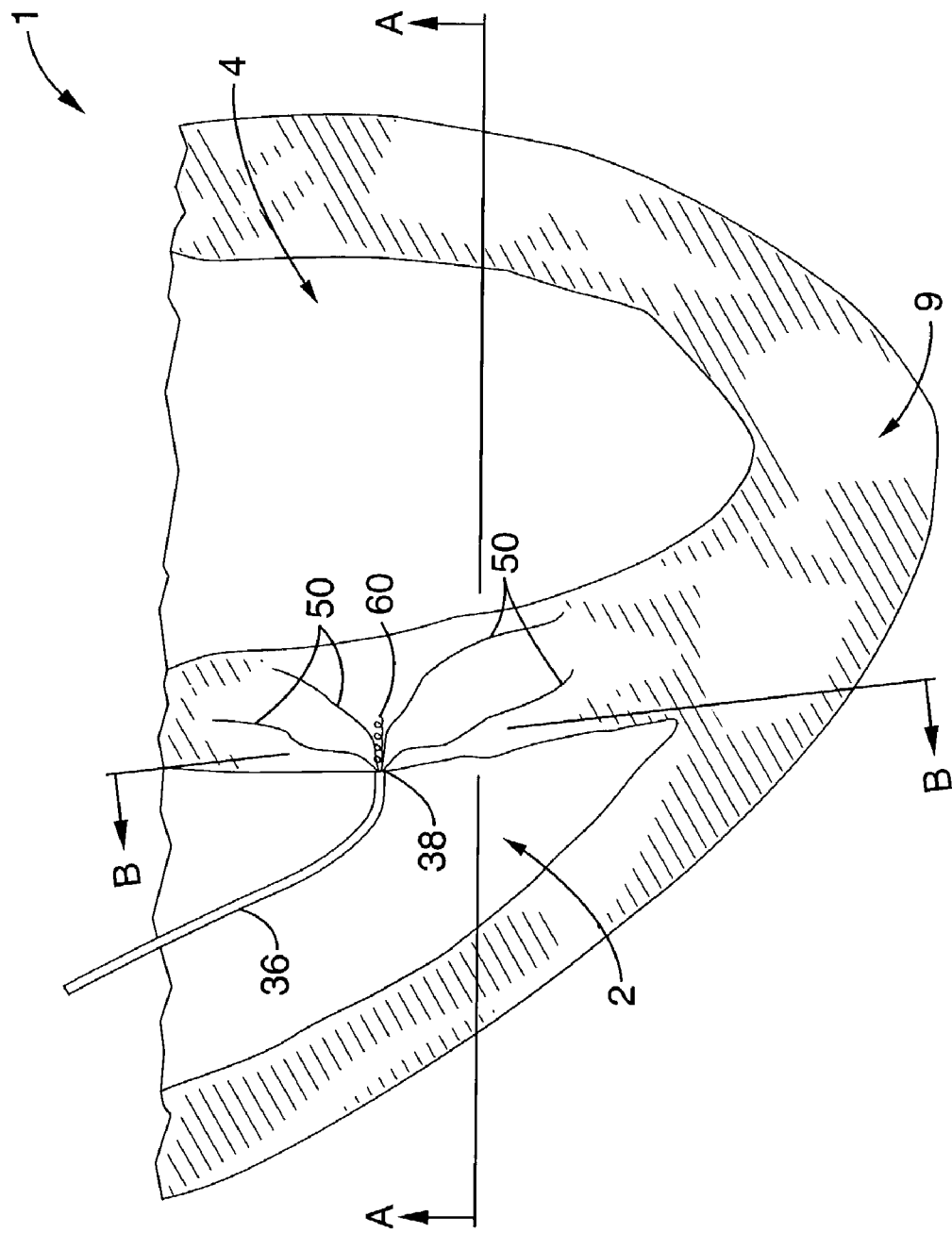
FIG. 10 shows a cross-sectioned view of a heart with another extendable electrode assembly of the invention using a screw anchor and multiple electrode leads deployed within a ventricular septum and coupled to a pacemaker (shown schematically) for biventricular septal pacing.

In any case, a further schematic view of the broad aspects for an arrayed electrode septal stimulation assembly during use is shown in FIG. 10. The array of electroded members 50 is shown in angular arrangement within a transversely cross-sectioned heart for illustration, but they may share a planar orientation, such as in a plane transverse to the plane of cross-section shown for heart 1. Accordingly, anchor element 60 is located within a region of septal wall tissue that is bound by electroded members 50 that have been positioned at unique respective locations around such central anchor 60 across the region. By providing members 50, 60, and tip 38 as stimulation electrodes coupled to a source of stimulation energy (not shown), the tissue bounded by electroded members 50 may be substantially stimulated, such as for biventricular pacing.

Figure 11B:
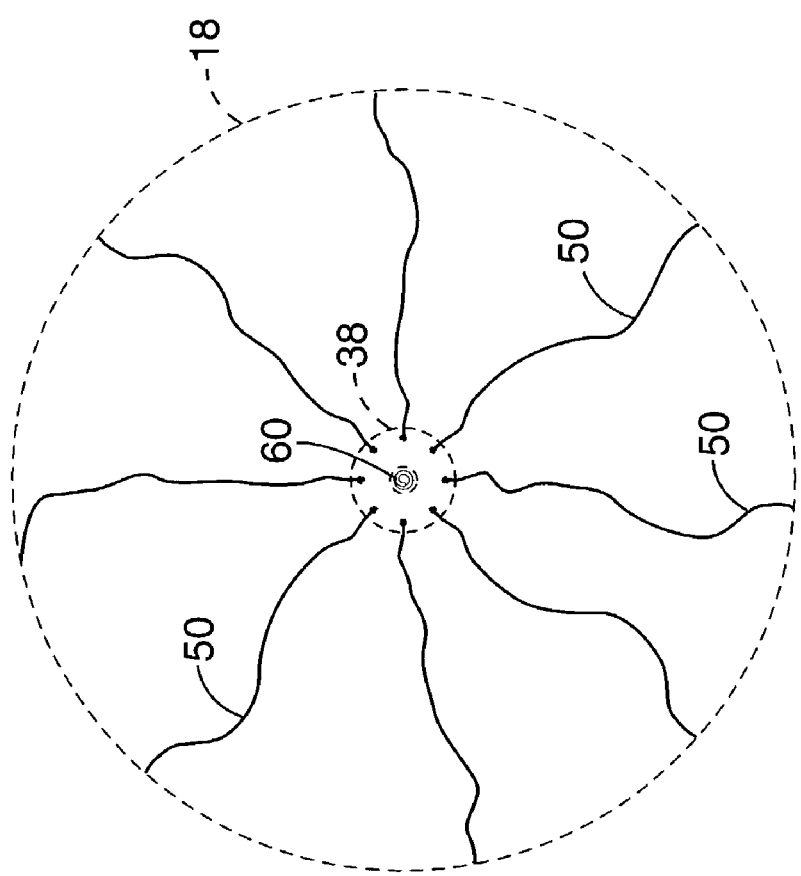
FIGS. 11A-B show transverse cross-sectioned views taken along lines A and B, respectively, in FIG. 10.
Figure 11A:
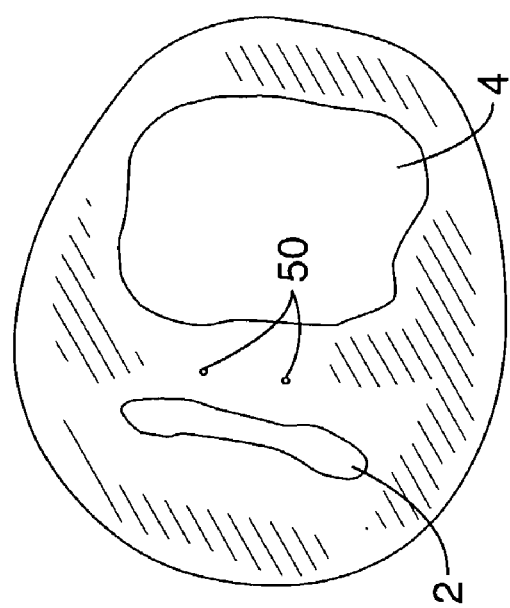
Figure 12B:
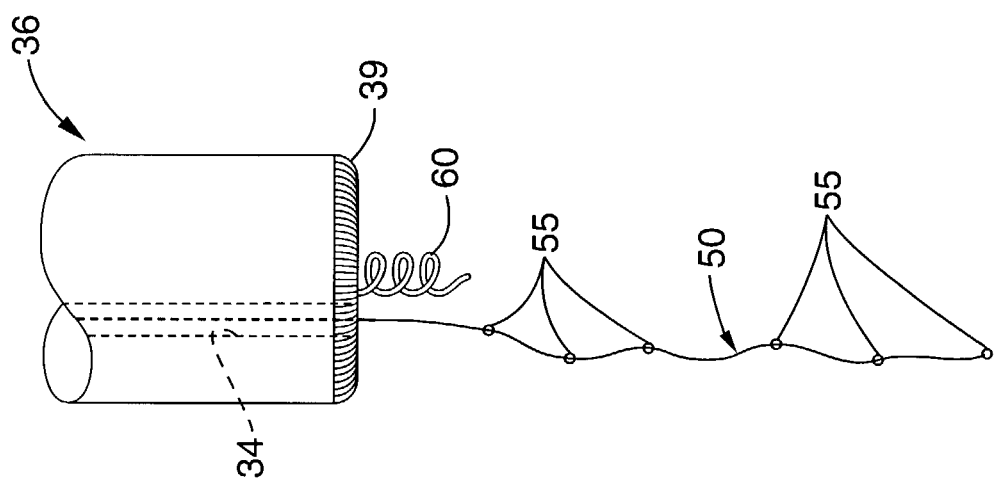
FIG. 12B shows a partially cross-sectioned view of an extendable electrode assembly adapted for use according to the embodiment shown in FIG. 12A.
Figure 12A:
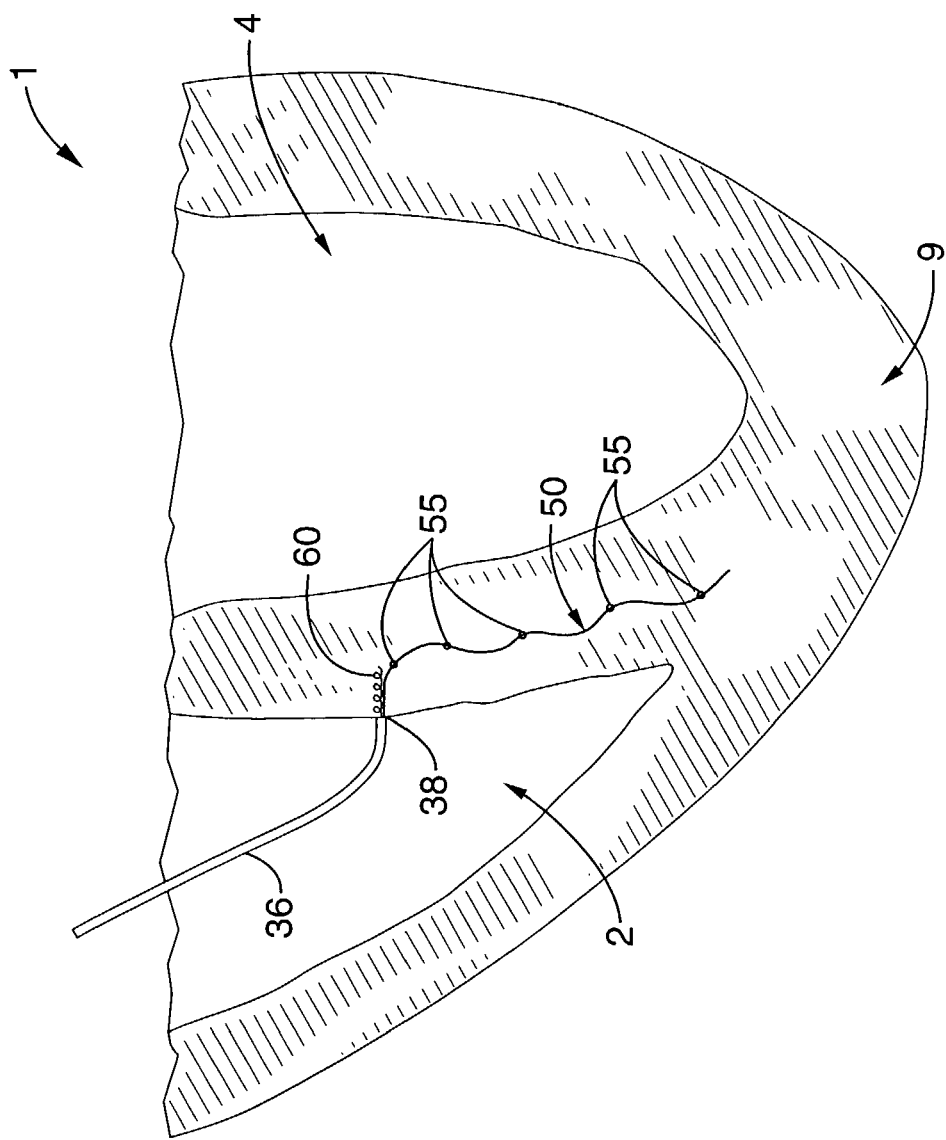
FIG. 12A shows a cross-sectioned view of a heart with another extendable electrode assembly of the invention using a screw anchor and a single lead with multiple electrodes deployed within a ventricular septum and coupled to a pacemaker (shown schematically) for biventricular septal pacing.

For further illustration of the orientation of such electroded elements are shown in different planes in FIGS. 11A-B, whereas FIG. 11B is further provided with a shadowed reference to the region 18 corresponding to the tissue being stimulated. However, the circumferential arrangement shown such as in FIG. 11B corresponding to region 18 may be modified, with different shapes than circular, with different lengths of members 50, for example, or with the central area such as at anchor 60 offset within the bound region 18. In one regard, the view of FIG. 11B shows a particular view of a planar array of members 50 in two dimensions. However, they may be of modified orientation to lie in different planes such that a three dimensional volume of septal tissue is defined as the region. Still further, the array of members 50 may be further modified such that the resulting stimulated region 18 is instead two or more discrete regions, as further herein described.

It is to be appreciated that despite the benefits of stimulating such region by elements 50, 60, and a ring electrode 38 at the septal wall surface, it is not necessary to provide all such elements as stimulation electrodes, and removal of any one or more of them and such resulting combination arrays are further contemplated embodiments hereof. For example, central screw electrode 60 may instead merely be provided as an anchor without electrical stimulation capability. Or, it may instead be a simple electrical lead and not necessary of the screw anchor configuration. In further examples of modifications that are contemplated, discrete electrodes may be positioned at various locations along the members 50 and within region 18, as shown at electrodes 55 in FIGS. 12A-B. Or the, the electroded elements 50 may be continuous segments with stimulation capability along their lengths out to the boundaries of region 18.

Figure 9:
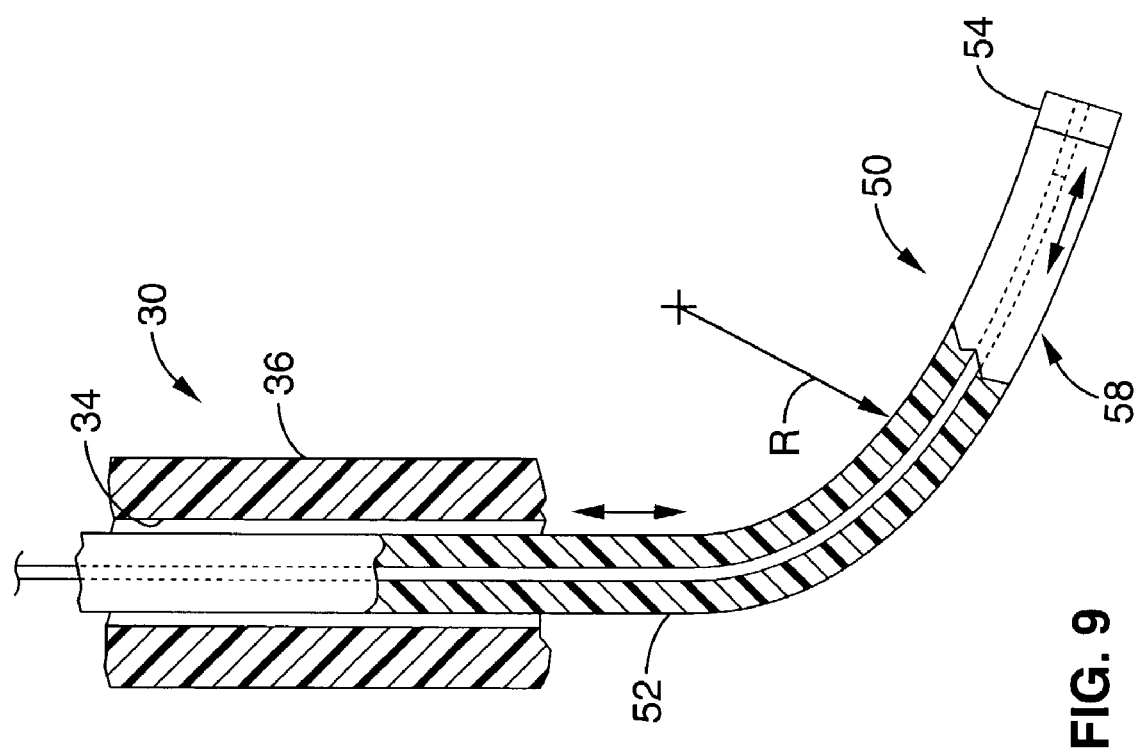
FIG. 9 shows a partially segmented view of another extendable electrode assembly according to the invention.
Figure 13A:
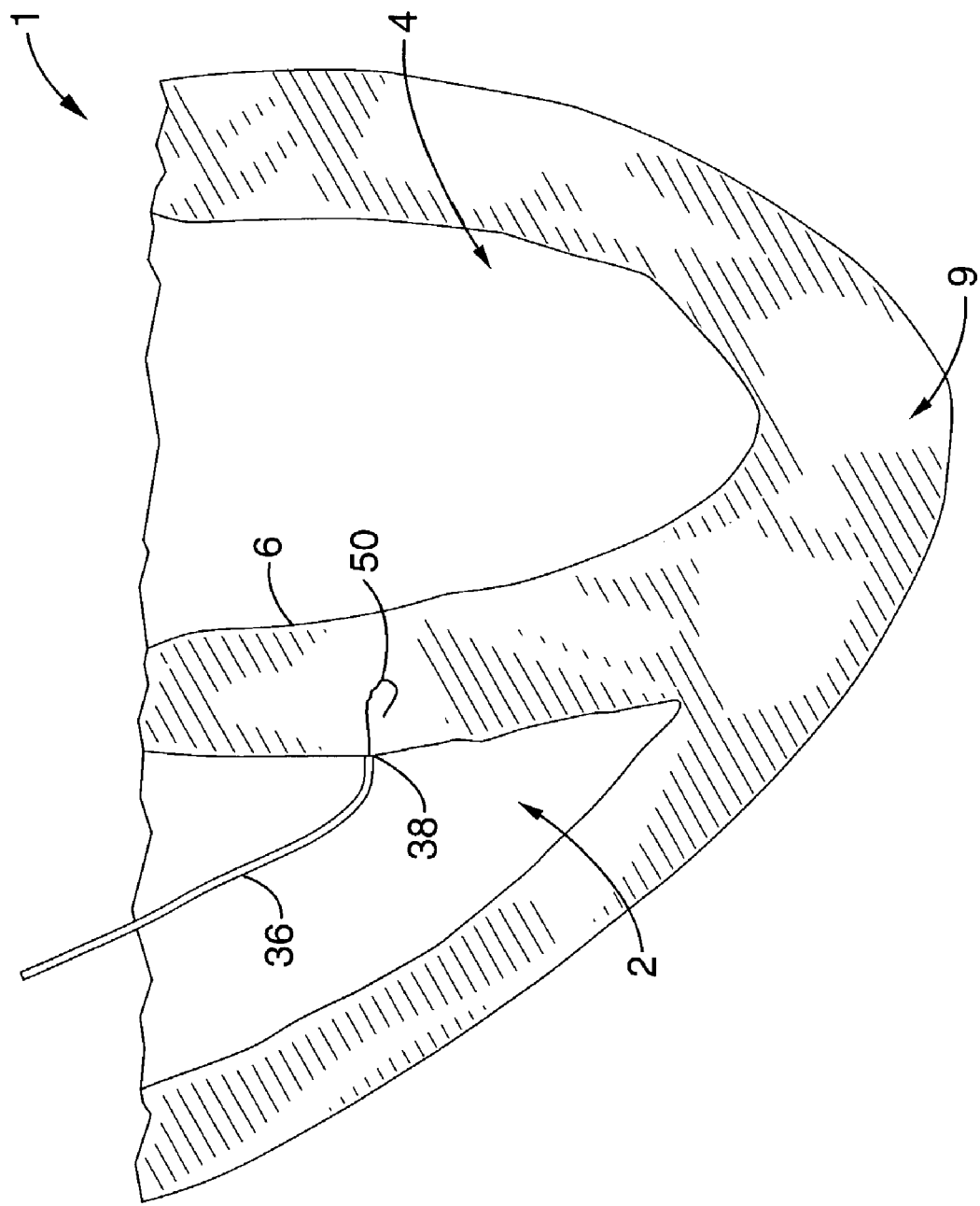
FIG. 13A shows a cross-sectioned view of a heart with another electrode assembly using a single intracardiac lead deployed within the ventricular septum in a first position.
Figure 13B:
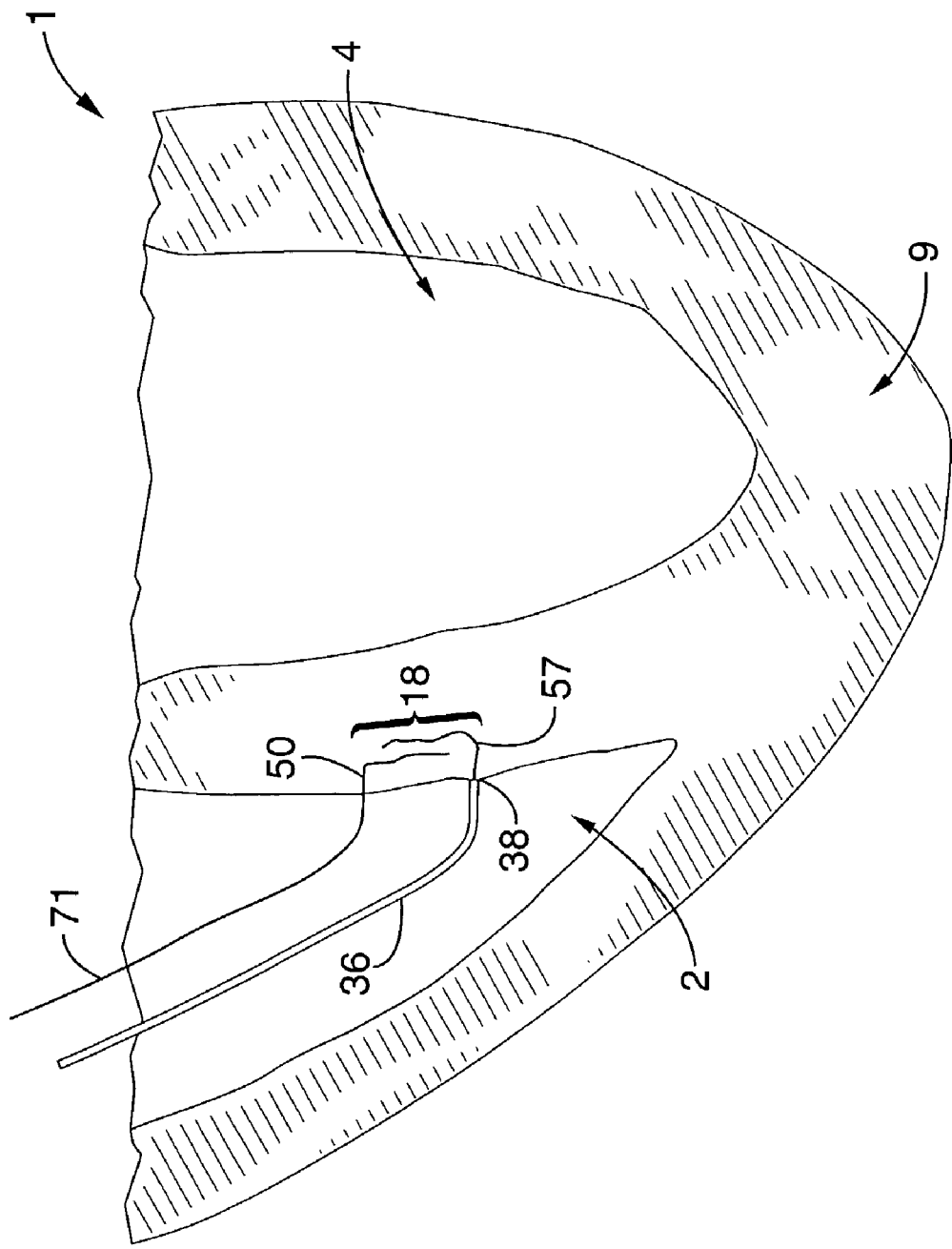
FIG. 13B shows a similar view to FIG. 13A but with multiple electrode leads implanted at first and second positions within the ventricular septum.

In one particular further embodiment shown in FIGS. 13A-B, an electroded member 50 is threaded into a region of tissue in septal wall 6, such as according to the needle or stylet embodiments of FIG. 8C or 9, respectively. Multiple such elements may be placed in this manner, as shown in FIG. 13B, in an arrangement such that the combination of multiple electroded elements 50 and 57 correspond to the overall region of tissue 18 that is stimulated thereby. These elements 50, 57 may be placed separately into the septal wall 6, with leads extending separately therefrom, such as shown in FIG. 13B, and such may be done with the same intracardiac delivery catheter 30 or separate delivery devices. After placement as shown in FIG. 13B, the leads for elements 50, 57 are coupled to an energy source, such as a pacemaker or defibrillator. It is further contemplated that the delivery catheter 30 is removed after placement of leads 50, 57 and before or after coupling to the energy source, or may remain indwelling if provided with sufficiently low profile and adapted for such long-term use (or if for temporary pacing).

Figure 13C:
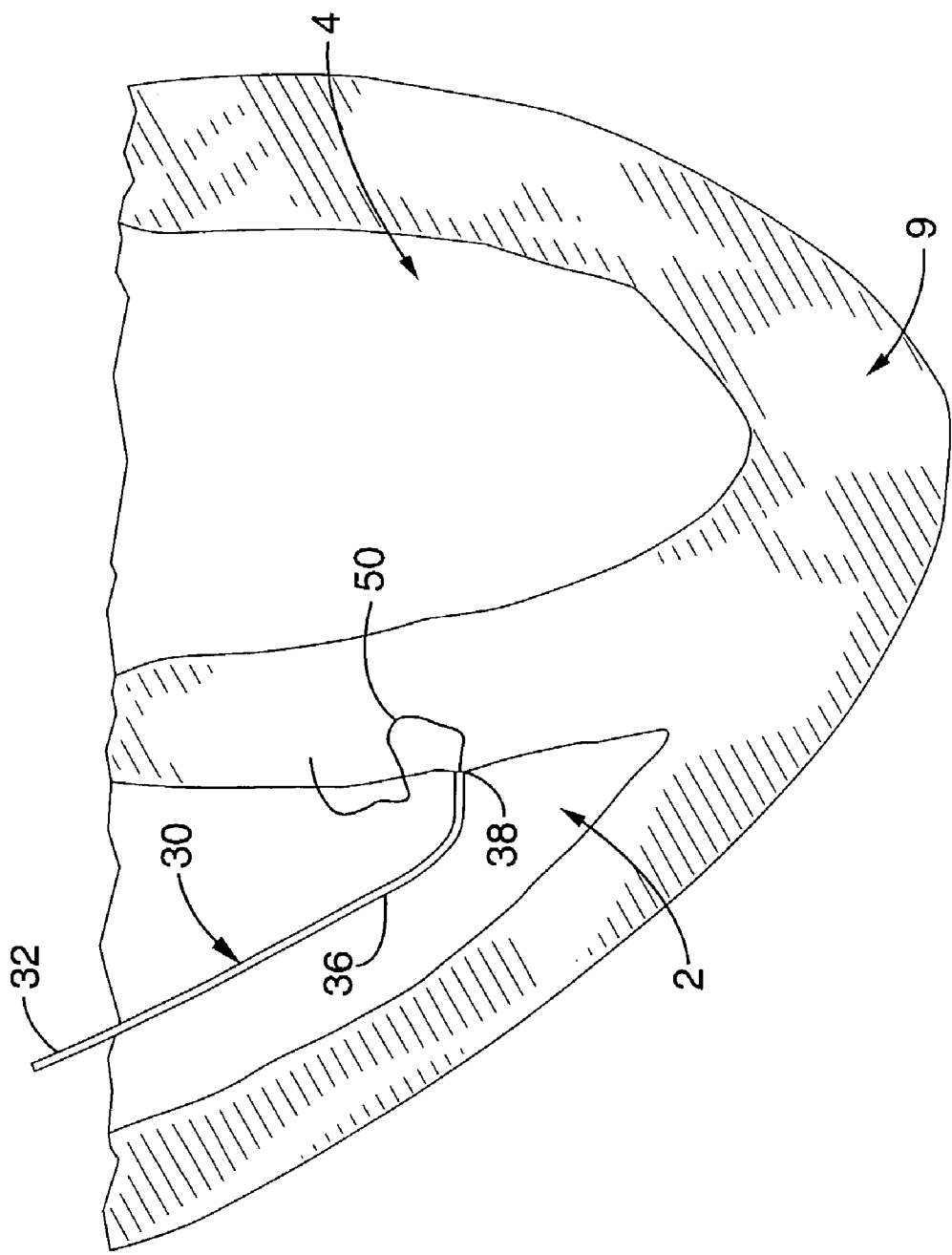
FIG. 13C shows a further mode stitching an electrical lead along a region of inter-ventricular septum.

A further modification is shown in FIG. 13C, wherein a remote mechanical stitching mechanism (not shown) is provided at the distal end 36 of delivery catheter 30 and adapted to stitch a single lead member 50 over a length or region of septal wall 6 tissue. Examples of such mechanism providing for such stitched lead placement over an extended length are provided in the following reference: "Flexible Microelectrode Arrays With Integrated Insertion Devices," by O'Brien, David P., Nichols, T. Richard, and Allen, Mark G., variously of the School of Electrical and Computer Engineering at Georgia Institute of Technology and the School of Medicine at Emory University, both in Atlanta, Ga. The disclosures of this reference is herein incorporated in its entirety by reference thereto.

Various modifications of the preceding embodiments may be made without departing from the scope of the invention, in particular in so far as modified in order to achieve certain particular desired results consistent with the objects of the invention.

For example, one desired result of the agent delivery and extendable electrode delivery embodiments is to pace the heart 1 over a large region of the septum 6, e.g. electrodes or agent spanning sufficient area of the septum 6 to void effects of bundle block there. Therefore, "substantial" area of the septum 6 generally means at least one-fifth of the septal wall, and may be even more beneficially one-fourth, and still more beneficially more than one-third or even one-half of the septum (ideally capturing the entire septum). In this regard, such "stimulation" is herein intended to mean the region that experiences artificial stimulation, such as either by the electrical discharge directly from an excitation electrode, or by enhanced propagation thereof via artificially delivered conductive agent. Moreover, deploying such agent or extendable electrodes may reach to the apex 9 or beyond. In any event, though stimulating such substantial regions is highly beneficial in many applications of the invention, it is not required in order to still achieve many of the other benefits afforded by the invention according to its various embodiments described herein.

The invention is particularly described herein for use with a pacemaker as an energy source 46 to be coupled to the electroded arrays 50 herein described, which can be implantable or temporary, and may be of the type commercially available. Or, such pacemaker may be modified for use with the electrode array assemblies 50 and/or agent or "bioelectrodes" 18 herein described. For example, for a given number of joules normally used to pace a heart 1 via the septum 6 using conventional electrode leads, such energy dose may be divided among the many electrodes of the array of the invention, thereby reducing the current density at the electrodes themselves. In another regard, more joules may be delivered in an impulse from the pacemaker over the span of electrodes in the array before reaching the same level at any one electrode otherwise delivered using conventional systems.

Other areas of the heart 1 may also be stimulated using the embodiments herein described, which may be modified as appropriate for such use according to one of ordinary skill.

In addition, other stimulation energy modalities may be used, e.g. ultrasound or microwave, though electrical stimulus is considered highly beneficial and efficacious according to prior experience in the industry. Moreover, to the extent "stimulation" is described with respect to the embodiments, it is generally intended that such stimulation is done to excite conductive activity and, therefore, done according to energy delivery modes that are generally non-ablative.

Cell cultures and in particular expression or overexpression of Cx43 or otherwise connexin have been specified herein as highly beneficial agent according to embodiments using agents to enhance cellular conduction in the heart. In particular association with stimulation devices, such agents are therefore considered "bioelectrodes", effectively extending the reach of the energy emitter (e.g. electrode) by virtue of the locally enhanced conduction—thus stimulating greater areas of the heart. The electrode and bioelectrode stimulate larger areas, mitigating deficits for synchronized conduction between the ventricles.

Other agents than "bioelectrodes" also having beneficial effects in similar uses are contemplated. For example, other substances may be injected or otherwise applied to the target tissue. Examples of such other substances include: polymers, which may be conducting in one regard (e.g. polyparol), or non-conducting (e.g. PLGA) in which case they may be coated such as with conductive metal; hydrogels, e.g. of the type carrying an ionic charge; or other solutions or suspensions such as carrying gold or other conductive metal particles or ions.

Still further, the invention further contemplates combinations or blends of the foregoing, such as according to one highly beneficial example combining cells, e.g. overexpressing Cx43, with a polymer delivery matrix (that may also be conductive, or may be non-conductive).

Figure 14A:
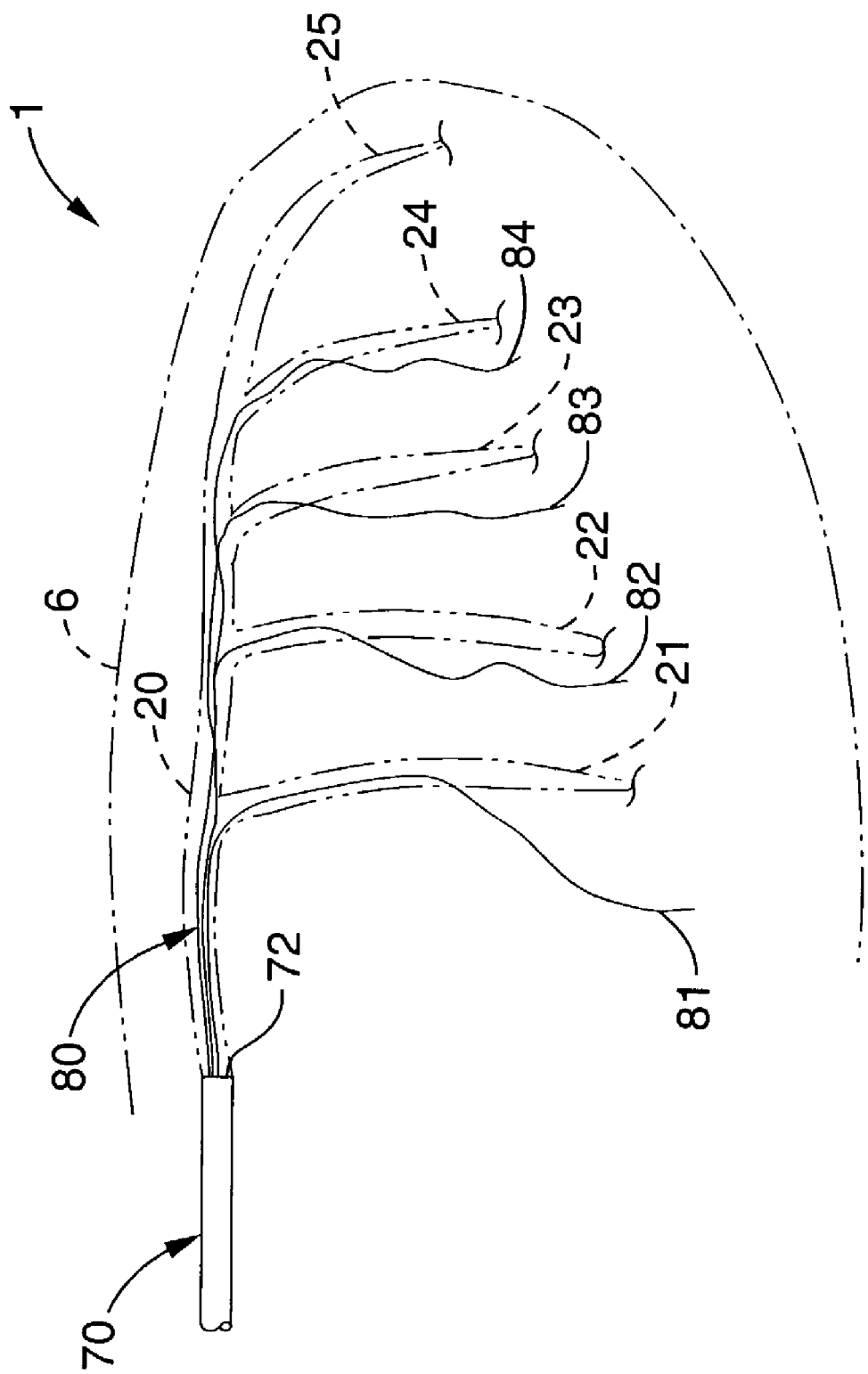
FIG. 14A shows a perspective view of a pacing electrode system using a coronary sinus delivery system for delivering pacing electrodes into myocardial septum of the ventricles through vessel walls of septal perforator blood vessels.
Figure 14B:
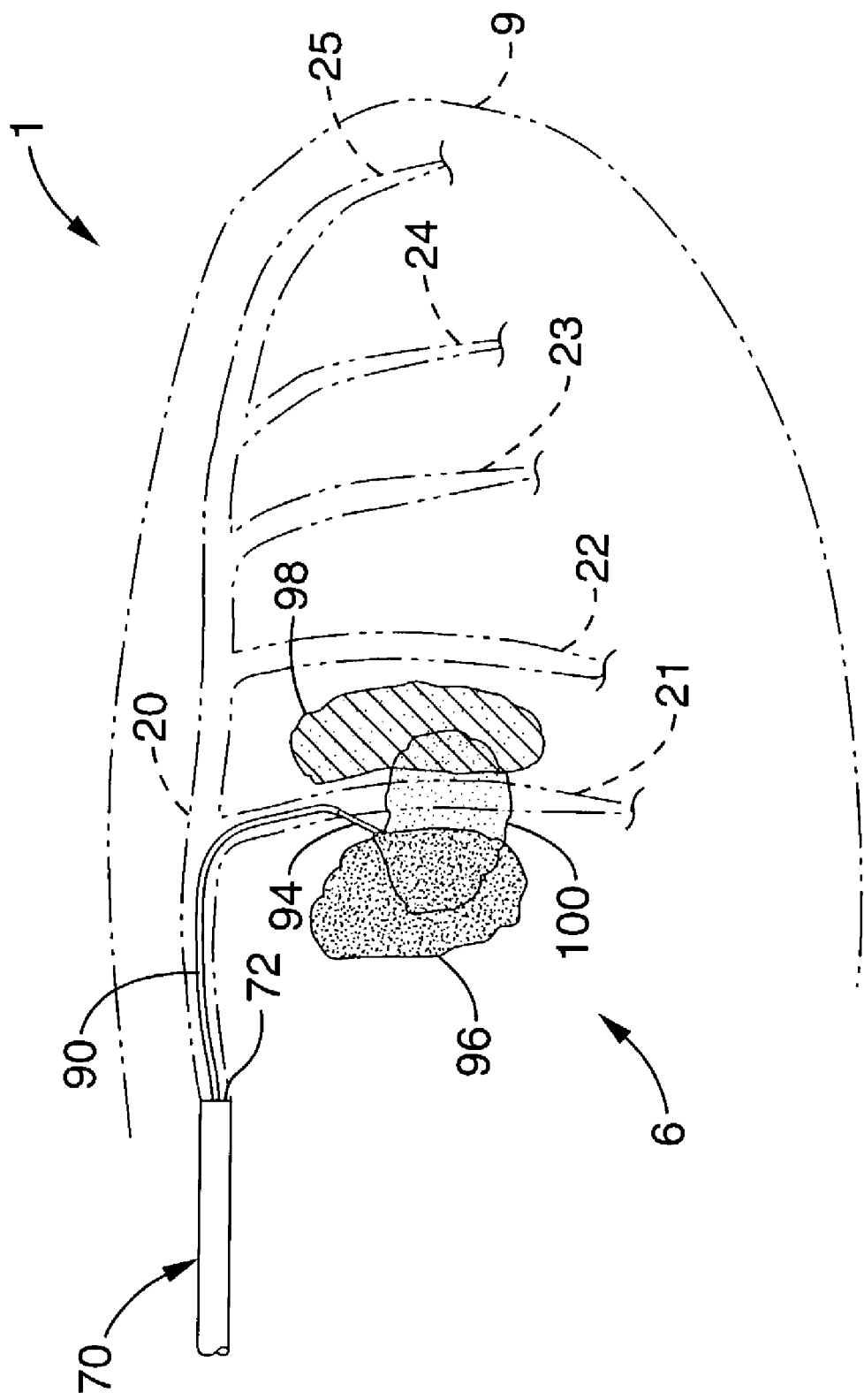
FIG. 14B shows a perspective view of an agent delivery system using the coronary sinus route to deliver agent that enhances cardiac conduction into myocardial tissue of the ventricular septal wall through the vessel wall of a septal perforator blood vessel.

Various combinations between the electrode assemblies and conductive agent delivery are also described above by reference to the illustrative embodiments, but further combinations and subcombinations, and modifications thereto, may be made. For example, screw electrodes may be adapted with a hollow lumen and used for the agent delivery. In another example, whereas FIGS. 14A-B show highly beneficial transvascular delivery of electrodes and conductive agent, respectively, into the ventricular septum, these may be combined. Alternatively, each may also be accomplished in combination with a transcardiac approach of the other. Still further, whereas some agent and/or electrodes may be delivered via a transcardiac delivery modality, other agent and/or electrodes may also be delivered via the transvascular septal perforator approach—each approach may provide for enhanced stimulation at different areas of the septum, whereas their combination may provide a complete and still more beneficial biventricular pacing result. To this end, the transcardiac approach is generally herein shown and described as the right heart system is often preferred for access. However, left ventricular transcardiac delivery of either or both of the agent or stimulus device(s) is also contemplated, instead of or in combination with the right ventricular approach (or transvascular approach). Any combination or sub-combination of these are contemplated, as should be apparent to one of ordinary skill based upon this disclosure.

Different volumes of agent, and different numbers, sizes, patterns, and/or lengths of stimulation leads may be used to suit a particular need. In one regard, a prior diagnostic analysis may be used to determine the extent of the condition, location of the condition, or various anatomical considerations of the patient which parameters set forth the volume of agent or electrode array to use. Or, a real time diagnostic approach may allow for stimulus effects to be monitored, such that the amount of agent, or distance, direction, or number of electrode deployment, is modified until the correct result is achieved. Therefore, for example, the electrodes of such embodiments may be retractable and advanceable through tissue so that different arrangements may be tried until synchronization is achieved.

It is further contemplated that the agent delivery and electrode embodiments, though highly beneficial in combination with each other, are independently beneficial and may be used to provide beneficial results without requiring the other.

Figure 15:
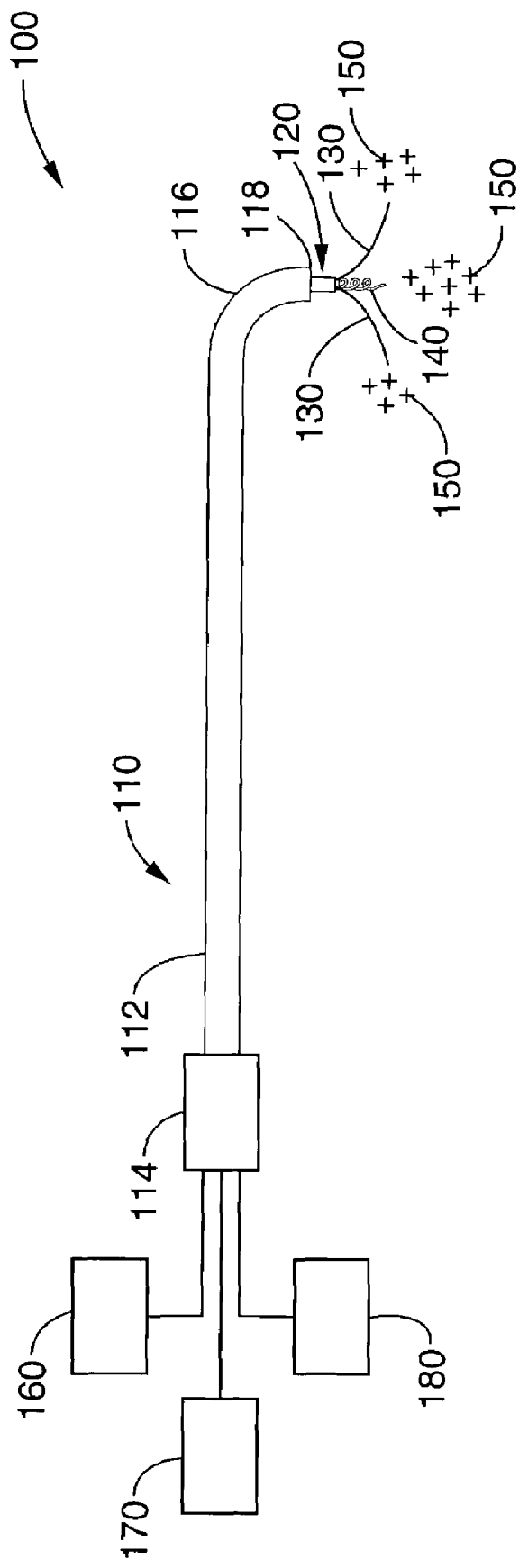
FIG. 15 shows a schematic view of a combined cardiac stimulation system according to an embodiment of the invention.

Notwithstanding the foregoing, a particular beneficial overall assembly is shown in FIG. 15. More specifically, cardiac stimulation system 100 is shown to include a delivery catheter 110 that cooperates to provide for both delivery of a bioelectrode 150 as well as stimulation electrodes 130 and an anchor 140 as follows. Delivery catheter 110 has a proximal end portion 112 with a proximal coupler 114, distal end portion 116, and distal tip 118, and is an intracardiac delivery catheter adapted to deliver its contents toward the inter-ventricular septum from the right ventricle. Extendable from delivery catheter 110 is an inner catheter 120 with an extendable screw anchor 140, and multiple spaced extendable electroded members 130 spaced about screw anchor 140. All or only some of central anchor 140, extendable electroded members 130, and the tip of member 120 may be provided as stimulation electrodes to be coupled to energy source 160, such as via shaft 120. Moreover, all or only some of central screw 140, extendable electroded members 130, or tip of member 220, may be further adapted to deliver a volume of bioelectrode agent into the region also coupled by the stimulation electrode sections, as shown at regions 150, such as via ports coupled to passageways (not shown) that are further coupled to a source of such agent 170 (shown schematically).

This combination device is considered highly beneficial for stimulating substantial portions of the inter-ventricular septum, such as for biventricular pacing and in particular treating LBBB. As further shown in FIG. 15 and illustrative of other embodiments providing extendable elements to be driven into tissue such as in the septal wall, a further device 180 may be coupled to such assembly that is an actuator that either allows for automated or manual extension of the respective extendable elements. Further elements that may be provided in an overall system such as that shown in FIG. 15 at 100, or other embodiments herein, include monitoring sensors and related hardware and/or software, such as incorporated into or otherwise cooperating with an energy source such as a pacemaker/defibrillator, including for example: to map electrical heart signals for diagnostic use in determining the stimulation mode; and/or feedback control related to the stimulation signal itself, such as set points, etc.

Connexin-Enhancing Conductive Agents

The present invention, to the extent using connexin-expressing cellular agents for injection as bioelectrodes, is related to co-pending U.S. patent application Ser. No. 10/291,202, filed Nov. 7, 2002, by the same inventor hereof, the disclosure of which is herein incorporated in its entirety by reference herein. Such aspect of the invention is based upon the experimental observation, based upon on man-made materials and methods, that contacting a myocardial cell with a recombinant cell, such as an adult skeletal muscle cell, which is modified to express a recombinant connexin 43 (e.g., in the presence or absence of endogenous connexin 43 expression) allows for electrical coupling of the modified skeletal muscle cell to the myocardial cell. The present invention according to the present embodiments thus provides methods for using a recombinant cell genetically modified to produce a connexin protein to produce persistent functional gap junctions between the recombinant cell and cardiomyocyte to obtain electrical communication between these cells. The use of recombinant cells that express recombinant Cx43 (or other connexin protein) increases and maintains the communication between the recombinant cells and myocardial cells, thus providing improved and coordinated electrical coupling with increased efficacy of myocardial contractility. The present invention provides methods of treatment of cardiac disease by transplanting or grafting recombinant cells modified to express a connexin into cardiac tissue to effect the ability to artificially stimulate regions of myocardial dysfunction, in particular in the setting of intra-ventricular septal stimulation, such as with pacemakers or defibrillators, such as for example for bi-ventricular pacing as a curative measure for heart block.

Definitions Related to Connexin Embodiments

The following definitions are intended to apply to embodiments of the present invention using biological or cellular material as bioelectrode agents, and in particular with respect to embodiments related to connexin-43 and/or such agents related to the production or expression thereof. To the extent such terms are elsewhere herein used with respect to other embodiments provided herein, such terms shall be given their ordinary, customary meaning according to one of ordinary skill in the art related to such embodiment, unless such terms are otherwise specifically defined with respect to such respective embodiment.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a connexin 43 polypeptide-encoding polynucleotide), "polynucleotide" is meant to encompass polynucleotides that encode a polypeptide that is functionally equivalent to the recited polypeptide, e.g., polynucleotides that are degenerate variants (i.e., polynucleotides that encode the same amino acid sequence but differ in polynucleotide sequence due to the degeneracy of the genetic code), or polynucleotides that encode biologically active variants or fragments of the recited polypeptide, including polynucleotides having substantial sequence similarity or sequence identity relative to the sequences provided herein. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

As used herein, "polypeptide" refers to an amino acid sequence of a recombinant or non-recombinant polypeptide having an amino acid sequence of i) a native polypeptide, ii) a biologically active fragment of an polypeptide, iii) biologically active polypeptide analogs of an polypeptide, or iv) a biologically active variant of an polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, "Human connexin 43 polypeptide" refers to the amino acid sequences of isolated human Cx43 polypeptide obtained from a human, and is meant to include all naturally-occurring allelic variants, and is not meant to limit the amino acid sequence to the complete, native amino acid sequence associated with the recited protein molecule.

A "variant" of a polypeptide is defined as an amino acid sequence that is altered by one or more amino acids (e.g., by deletion, addition, insertion and/or substitution). Generally, "addition" refers to nucleotide or amino acid residues added to an end of the molecule, while "insertion" refers to nucleotide or amino acid residues between residues of a naturally-occurring molecule. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, added, inserted or deleted without abolishing biological or immunological activity can be found using computer programs well known in the art, for example, DNAStar software.

By "nucleic acid of interest" is meant any nucleic acid (e.g., DNA) which encodes a protein or other molecule which is desirable for inducing or maintaining electrical coupling between cells. In general, the nucleic acid is operatively linked to other sequences which are needed for its regulation and expression, such as a promoter and regulatory elements.

The term "biologically active" where herein used in particular respect to connexin, or biological or cellular material effecting production thereof, refers to, for example, a compound having structural, regulatory, or biochemical functions of a naturally occurring connexin polypeptide, particularly with respect to facilitating the establishment of an electrochemical connection between a cell modified to express a connexin polypeptide and a myocardial cell, and includes in particular such human connexin polypeptides. Likewise, "immunologically active" defines the capability of the natural, recombinant or synthetic human connexin polypeptide, or any oligopeptide thereof, to induce a specific immune response in appropriate animals or cells and to bind with a connexin specific antibody.

The term "derivative" as used herein refers to the chemical modification of a nucleic acid encoding a polypeptide or the encoded polypeptide. Illustrative of such modifications would be replacement of hydrogen by an alkyl, acyl, or amino group. A nucleic acid derivative would encode a polypeptide which retains essential biological characteristics of a natural polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

By "transformation", "transduction" or "transfection" is meant a permanent or transient genetic change, preferably a permanent genetic change, induced in a cell following incorporation of new nucleic acid (e.g., DNA or RNA exogenous to the cell). Genetic change can be accomplished either by incorporation of the new nucleic acid into the genome of the host cell, or by transient or stable maintenance of the new DNA as an episomal element.

By "transformed cell", "transfected cell" or "transduced cell" is meant a cell into which (or into an ancestor of which) has been introduced, by means of recombinant DNA techniques, a DNA molecule encoding a protein of interest.

By "construct" is meant a recombinant nucleic acid, generally recombinant DNA, that has been generated for the purpose of the expression of a specific nucleotide sequence(s), or is to be used in the construction of other recombinant nucleotide sequences. Constructs useful in the invention are those which comprise connexin-encoding gene sequence operably linked to a promoter which will allow for the expression of the connexin protein in a transformed cell. Exemplary constructs useful for the expression of human and rat Cx43 in accordance with the invention are described in Shinoura, N, et al., J. Neurosurg. 1996 May; 84(5):839-45 and Suzuki et al, Ann. Thorac. Surg., 2001, 71:1724-33, respectively.

By "promoter" is meant a minimal sequence sufficient to direct transcription in a recombinant cell. "Promoter" is also meant to encompass those elements sufficient for promoter-dependent gene expression controllable for cell-type specific, tissue-specific or inducible by external signals or agents; such elements may be located in the 5' or 3' regions of the native gene (e.g., enhancer elements).

By "operably linked" or "operatively linked" is meant that a DNA sequence and a regulatory sequence(s) are connected in such a way as to permit expression when the appropriate molecules (e.g., transcriptional activator proteins) are bound to the regulatory sequence(s).

By "connexin gene" is meant the open reading frame encoding a connexin polypeptide, or introns, or biologically active fragment thereof. "Connexin gene" includes adjacent 5' and 3' non-coding nucleotide sequences involved in the regulation of expression, up to about 10 kb beyond the coding region, but possibly further in either direction. The DNA sequences encoding a connexin may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

By "cardiomyocyte" is meant a cardiac contractile cell, which is a cardiac muscle cell. The cardiomyocyte cell may be isolated and cultured in vitro or be part of the myocardium of a host.

By "skeletal muscle cell" is meant a cell found in skeletal muscle which includes but not limited to myoblasts, myotubes and mature skeletal muscle cells.

By "recombinant cell" is meant a cell comprising nucleic acid not normally associated with the cell (e.g. a cell transformed, transduced or transfected with a construct encoding a specific protein, e.g., a connexin protein).

By "transplanted cell" is meant a cell which has been introduced into a host so as to be in contact with a cell within a host. For example, a recombinant cell or cells maybe grafted and/or implanted into the cardiac tissue of a host.

By "therapeutically effective amount" in the context of the present embodiments for treatment of cardiac conduction disturbances is meant an amount effective to decrease a symptom of cardiac conduction disturbance and/or to improve cardiac conductance (a measure of conduction).

By "overexpressing" or "overexpression" of a gene product (such as a Cx43 protein) is meant an increased level of protein expression over a normal level of protein expression for a particular cell or cell type at, for example, a particular developmental stage or stage of differentiation. In certain instances, overexpressing can be a cumulative effect of protein expression from endogenous and recombinant genes or essentially protein expression from a recombinant gene. Overexpression of a connexin (e.g., Cx43) is meant to refer to the expression of connexin protein within a particular cell which is above the connexin expression level normally associated with a normal or wild-type cell at a particular stage of differentiation. For cells which normally do not express significant or detectable amounts of the connexin (e.g. as with Cx43 in adult skeletal muscle cells or myotubes), overexpression of connexin protein would mean any detectable expression of connexin, and particularly a level of expression sufficient to promote establishment of an electrochemical connection between the recombinant cell in which connexin expression is elevated and a cardiomyocyte. In certain embodiments overexpression of connexin is meant an increase in expression by a factor of at least about 2 fold, in other embodiments at least about 5 fold and yet in still other embodiments at least about 10 fold.

The terms "subject", "patient", "host" and "individual" are used interchangeably herein to refer to any mammalian subject for whom diagnosis or therapy is desired, particularly humans. Other subjects may include cattle, dogs, cats, guinea pigs, rabbits, rats, mice, horses, and so on. Of particular interest are subjects having a myocardial associated disorder that is amenable to treatment (e.g., to mitigate symptoms associated with the disorder) by the transplantation of cells which express a recombinant connexin (e.g., Cx43) into the subject (e.g., by introduction of a recombinant connexin expressing cell into the subject in vivo, or by grafting cells expressing a connexin (e.g., adult skeletal myoblasts, stem cells (e.g., mesenchymal, hematopoietic), fibroblasts, cardiac cells, etc.) into the subject. In many embodiments the hosts will be humans.

The terms "electrical coupling" with respect to intercellular junctions are intended to mean the interaction between cells which allows for intracellular communication between cells so as to provide for electrical conduction between the cells. Electrical coupling in vivo provides the basis for, and is generally accompanied by, electromechanical coupling, in which electrical excitation of cells through gap junctions in the muscle leads to muscle contraction.

By "cardiac conduction disturbance" is meant a disturbance in the normal generation and transmission of the electrical activity that initiates myocardial contraction. Cardiac arrhythmias resulting from electrical conduction disturbances can lead to life threatening ventricular tachyarrhythmias, hemodynamically compromising bradycardias, and heart block.

By "condition related to a cardiac conduction disturbance" is meant a condition, symptom or disorder associated with cardiac conduction disturbance. Examples of conditions related to cardiac conduction disturbance are irregular heart beat, fatigue, shortness of breath, and lack of synchronized heart muscle contraction.

By "treatment", "treating", or "treat" is meant that at least an amelioraton of the symptoms associated with the condition afflicting the host is achieved, where amelioration is used in a broad sense to refer to at least a reduction in the magnitude of a parameter, e.g. symptom (such as irregular heart beat, fatigue, shortness of breath, syncope can be symptoms associated with conduction disturbances as heart block, ventricular tachycardias or associated with congestive heart failure (i.e. lack of synchronized contraction)) associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition. In another regard, such terms include enhancing the ability to stimulate at least a region of the heart.

Methods of Establishing Electrical Connection Between A Connexin-Overexpressing Cell and a Myocardial Cell The present embodiments of the invention provide methods for establishing an electrical connection between a recombinant cell expressing a connexin, and a myocardial cell, and including in additional modes a further coupling with an artificial cardiac stimulation energy source. The methods generally involve contacting a connexin recombinant cell (e.g., a skeletal muscle cell, stem cell (e.g., mesenchymal, hematopoetic), fibroblast, cardiac cell, etc.) with a myocardial cell in a manner that provides for production of an electrical connection between the myocardial cell and the recombinant cell. The cell is recombinant, e.g., it is genetically modified to produce a biologically active connexin protein, e.g., connexin 43 (Cx43) protein. Production of connexin in the recombinant cell provides for an electrical connection, and thus an electromechanical connection, between the recombinant cell and the myocardial cell.

Connexin-Encoding Nucleic Acids

As summarized above, the methods of the present embodiments of the invention utilize nucleic acid compositions, including genomic and cDNA nucleic acid compositions, that encode biologically active connexin 43 proteins, or biologically active fragments, homologs, or analogues thereof suitable for expression in a recombinant cell which cell can subsequently form a electrochemical connection with a cardiac cell.

By "connexin protein" is meant a protein from the family of homologous proteins found in connexins of gap junctions as homo- or heterohexameric arrays. Connexin proteins are the major gap junction protein involved in the electrical coupling of cells. Gap junctions regulate intercellular passage of molecules, including inorganic ions and second messengers, thus achieving electrical coupling of cells. Over 15 connexin subunit isoforms are known, varying in size between about 25 kDa and 60 kDa and generally having four putative transmembrane □-helical spanners. Different connexins are specific for various parts of the heart. Connexin family proteins found in the cardiovascular system includes Cx37, Cx40, Cx43, and Cx45 (van Veen, A A; van Rijen, H V; Opthof, T., Cardiovascular Research 2001 Aug. 1, 51(2): 217-29.; Severs, N J; Rothery, S; Dupont, E; Coppen, S R; Yeh, H I; Ko, Y S; Matsushita, T; Kaba, R; Halliday, D., Microscopy Research and Technique 2001 Feb 1, 52(3):301-22; Kwong, K F; Schuessler, R B; Green, K G; Laing, J G; Beyer, E C; Boineau, J P; Saffitz, J E., Circulation Research 1998 Mar 23, 82(5):604-12).

As used interchangeably herein, "Connexin 43" and "Cx43" refer to the amino acid sequences of an isolated Cx43 polypeptide, having structural, regulatory, or biochemical functions associated with gap junctions and electromechanical coupling, obtained from any species, particularly mammalian, including human, rodenti (e.g., murine or rat), bovine, ovine, porcine, murine, or equine, preferably human, and may be natural, synthetic, semi-synthetic or recombinant, and is meant to include all naturally-occurring allelic variants, and is not meant to limit the amino acid sequence to the complete, native amino acid sequence associated with the recited protein molecule. Cx43 encompasses biologically active Cx43 fragments. Examples of Cx43 include human Cx43 (Genbank Accession Nos. XP_027460, XP_027459, XP_004121, P17302, AAD37802, A35853, NP_000156, AF151980, M65188, and AAA52131), mouse Cx43 (Genbank Accession Nos. P23242, P18246, A39802, A36623, NP_034418, NM_012567, NM_010288, CM44640) and rat Cx43 are found at Genbank Accession Nos. P08050, S00532, NP_036699, AAA75194 and 1404339A.

A connexin genomic sequence of interest comprises the nucleic acid present between the initiation codon and the stop codon, with a connexin 43 gene being of particular interest, including all of the introns that are normally present in a native chromosome. It may further include the 3' and 5' untranslated regions found in the mature mRNA. It may further include specific transcriptional and translational regulatory sequences, such as promoters, enhancers, etc., including about 10 kb, but possibly more, of flanking genomic DNA at either the 5' or 3' end of the transcribed region. The genomic DNA may be isolated as a large fragment of 100 kbp or more, or as a smaller fragment substantially free of flanking chromosomal sequence. In another embodiment, the connexin DNA is a cDNA, which lacks intronic sequences that may be found in the genomic DNA. The cDNA may be operably linked to a promoter that is normally associated with the connexin sequence (e.g., a promoter endogenous to the connexin gene) or that is heterologous to the connexin sequence (i.e., a promoter from a source other than the connexin sequence).

The sequence of this 5' region, and further 5' upstream sequences and 3' downstream sequences, may be utilized for promoter elements, including enhancer binding sites, that provide for expression in tissues where the connexin polypeptide is normally expressed. The connexin sequence used can be based on the nucleotide sequences of any species (e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human) and can be isolated or produced from any source whether natural, synthetic, semi-synthetic or recombinant. Where the recombinant cell is a human cell, or where the cardiac tissue into which the cell is to be implanted is human, the connexin is preferably a human connexin or derived from a human connexin.

The nucleic acid compositions used in the present embodiments of the invention may encode all or a part, usually at least substantially all, of the connexin polypeptide as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about 100 contiguous nucleotides, usually at least about 200 nt, more usually at least about 250 nt to about 500 nt.

The connexin genes are isolated and obtained in substantial purity, generally as other than an intact mammalian chromosome. Usually, the DNA will be obtained substantially free of other nucleic acid sequences that do not include a sequence encoding a Cx43 or fragment thereof, generally being at least about 50%, usually at least about 90% pure and are typically "recombinant", i.e. flanked by one or more nucleotides with which it is not normally associated on a naturally occurring chromosome.

The sequence of the connexin protein, including flanking promoter regions and coding regions, may be mutated in various ways known in the art to generate targeted changes in promoter strength, sequence of the encoded protein, etc. The DNA sequence or product of such a mutation will be substantially similar to one or more of the sequences provided herein, i.e. will differ by at least one nucleotide or amino acid, respectively, and may differ by at least two, or by at least about ten or more nucleotides or amino acids. In general, the sequence changes may be additions, substitutions, insertions or deletions. Deletions may further include larger changes, such as deletions of a domain or exon. Such modified connexins sequences can be used, for example, to generate constructs for introduction into cells for the purpose of promoting production of electrochemical connections.

It should be noted that preferably the connexin gene is selected according to the genus and species of the host (e.g., where a human is to receive Cx43-modifed cells, then the Cx43 gene sequence is a human Cx43).

The encoded connexin is biologically active, e.g., when produced in a skeletal muscle cell, a biologically active Cx43 polypeptide facilitates establishment of a connection between the skeletal muscle cell and a myocardial cell. Without being held to theory, the connexin protein (e.g., Cx43) is expressed at the cell surface and is inserted into the plasma membrane as part of gap junctions. To establish electrical coupling between cells, connexin must be functional gap junctions to form gap junctional intercellular communication (GJIC). The identification of an electrical connection between two cells (e.g. such as an adult skeletal muscle cell and a myocardial cell) can be readily determined by those skilled in the art. Gap junctions can be evaluated by microinjecting cells with a gap junction permeable dye, e.g., Lucifer yellow (Molecular Probes, Or.), which is transferred from one cell to another when functional gap junctions are present. A micro injection protocol for detecting functional gap junctions (i.e. functional expression of Cx43) is given in the Examples section below.

The recombinant cells can optionally be genetically modified to express other proteins, such as N-cadherin protein. However, the cells are preferably are not so modified so as to avoid additional genetic manipulation of the cell to be transplanted. Furthermore, the recombinant cell need not be modified to express or overexpress N-cadherin, as the inventors here have shown that expression of an exogenous (e.g., introduced or recombinant) connexin (either in the presence or absence of expression of any endogenous connexin) is sufficient.

Constructs For Connexin Nucleic Acids

Constructs comprising connexin nucleic acids are well known in the art. For example, constructs containing the connexin 43 gene are described by E I Oakley, et al, Ann. Thorac. Surg., 2001, 71:1724-33. Constructs comprising connexin-encoding nucleic acids are utilized to transform, transfect or transduce specific cells of interest to allow for the expression of an introduced connexin-encoding nucleic acid molecule in the modified cell.

Where the nucleic acid to be expressed is DNA, any construct having a promoter (e.g., a promoter that is functional in a eukaryotic cell) operably linked to a DNA of interest can be used in the invention. The constructs containing the DNA sequence (or the corresponding RNA sequence) which may be used in accordance with the invention may be any expression construct suitable for use in a mammalian cell, and containing the DNA or the RNA sequence of interest. Such constructs can include nucleic acid of a plasmid or viral construct (e.g. adeno associated virus, adenovirus, and the liked) and can be circular or linear. Preferably the construct is capable of replication in eukaryotic and/or prokaryotic hosts. Suitable constructs are known in the art and are commercially available. The constructs can be prepared using techniques well known in the art. Likewise, techniques for obtaining expression of exogenous DNA or RNA sequences in a genetically altered host cell are known in the art.

In one embodiment, the DNA construct contains a promoter to facilitate expression of the DNA of interest within a mammalian cell. The promoter may be a strong promoter that functions in mammalian cells, such as a promoter from cytomegalovirus (CMV), mouse mammary tumor virus (MMTV), Rous sarcoma virus (RSV), lenti-virus or adenovirus. More specifically, exemplary promoters include the promoter from the immediate early gene of human CMV (Boshart et al., Cell 41:521-530, 1985) and the promoter from the long terminal repeat (LTR) of RSV (Gorman et al., Proc. Natl. Acad. Sci. USA 79:6777-6781, 1982). Alternatively, the promoter used may be a strong general eukaryotic promoter such as the actin gene promoter. In one embodiment, the promoter used may be a tissue-specific promoter. For example, the promoter used in the construct may be a cardiac cell specific promoter, a myoblast specific promoter or an adult skeletal muscle cell specific promoter (Luo, et. al., Development 2001 February, 128(4):459-69; Lee, et. al., J. Thor. Card. Sur. 1999 July, 118(1):26-4, discussion 34-5). Primary cardiac myocytes from neonatal rats have been transfected with a reporter construct driven by the C promoter of rat acyl-coenzyme synthetase gene (Kanda, et al. Heart Vessels 2000, 15(4): 191-6) as well as alpha- and beta-cardiac myosin heavy chain gene promoters (James, et. al., Circulation 2000 Apr. 11, 101(14):1715-21).

The constructs of the present embodiments of the invention may also include sequences in addition to promoters which enhance and regulate connexin expression in modified cells. For example the serum response factor (SRF) gene has been shown to regulate transcription of numerous muscle and growth factor-inducible genes. Because SRF is not muscle specific, it has been postulated to activate muscle genes by recruiting myogenic accessory factors. Myocardin is a member of a class of muscle transcription factors, provides a mechanism whereby SRF can convey myogenic activity to muscle genes. (Wang, et. al., Cell. 2001 Jun. 29;105(7):851-62).

In another embodiment, the promoter is a regulated promoter (e.g., inducible promoter), such as a tetracycline-regulated promoter, expression from which can be regulated by exposure to an exogenous substance (e.g., tetracycline). Another example of regulated promoter system useful in the present invention is the lac operator-repressor gene regulatory system to regulate mammalian promoters (Cronin, et. al., Genes Dev. 2001 Jun. 15, 15(12):1506-17).

For eukaryotic expression, the construct should contain at a minimum a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used (e.g., the human-globin intron, which is inserted in the construct at a position 5' to the DNA of interest).

In an alternative embodiment, the nucleic acid delivered to the cell is an RNA encoding a connexin protein. In this embodiment, the RNA is adapted for expression (i.e., translation of the RNA) in a target cell. Methods for production of RNA (e.g., mRNA) encoding a protein of interest are well known in the art, and can be readily applied to the product of RNA encoding connexin useful in the present invention.

Production Of Recombinant Connexin Cells

Cells to be modified to express a recombinant connexin include any cell capable of coupling with a cardiomyocyte via connexin-mediated gap junctions, including skeletal muscle cells, stem cells (e.g., mesenchymal, hematopoietic), fibroblasts, cardiac cells, and the like, following genetic modification to provide for expression of a recombinant connexin (e.g., Cx43) in the cell. In one embodiment of particular interest, the cells are skeletal muscle cells.

Cells may be obtained from the host (e.g., endogenous cells) or from appropriate cultured cell lines. Cells may be autologous, allogeneic, or xenogeneic (e.g., primate, pig, etc.) with respect to the host. In certain embodiments, the cells are collected from the subject or patient via biopsy (e.g., muscle biopsy). This latter embodiment allows for autologous transplantation of recombinant connexin-expressing cells into host myocardium.

Cells suitable for use to produce recombinant connexin-expressing cells include skeletal muscle cells, particularly adult skeletal muscle cells, stem cells (e.g., mesenchymal, hematopoietic), fibroblasts, cardiac cells, and the like. An expression construct that provides for production of connexin (e.g., Cx43) is then introduced into the cells which may be propagated and cultured in vitro before and/or after transformation to increase the number of recombinant connexin-expressing cells available for transplantation into myocardial tissue.

In one more specific embodiment, the cell is a skeletal cell muscle cell or cell line, propagated and transformed with an appropriate vector for the expression of a connexin (e.g., Cx43). These recombinant connexin expressing cells are cultured in vitro and utilized for transplantation into myocardium. In another embodiment, the cells are cells of a fresh primary culture or a frozen culture.

Methods for introducing connexin constructs into a mammalian cell include standard protocols known to those skilled in the art.

The regulation of connexin expression can be accomplished using regulatory elements operably inserted into the construct comprising the connexin gene used to transduce the modified cells. Other methods of regulating connexin expression may include genomic regulatory elements endogenous to the recombinant cells or by the addition of compounds that modulate connexin expression (e.g., either at the time of or following implanting the recombinant cells.)

Connexin expression in the modified cells can be detected by such techniques as western blotting, utilizing antibodies specific for the recombinant connexin. Other methods for confirming the expression of a recombinant connexin in transformed cells may involve RT-PCR utilizing primers specific for connexin mRNA or immunofluorescence techniques on transformed cells in culture. The ability of a connexin polypeptide, to facilitate production of an electrical connection between a recombinant cell and a cardiomyocyte can be tested in an in vivo model.

Production of Functional Gap Junctions Between Recombinant Connexin Cells and Cardiomyocytes The recombinant connexin-expressing cells can be cultured to expand the number of cells in vitro. After a desired number of recombinant cells are obtained, the cells are introduced into myocardial tissue. Alternatively or in addition, recombinant connexin cells and myocardial cells are co-cultured in vitro and then transplanted.

Production of a connexin allows the modified cells to induce an electrical connection with myocardial cells via gap junctions. Due to the difference in the cellular and electrophysiological properties of myocardial cells and non-myocardial cells, tight coupling of myocardial and non-myocardial cells is required for synchronized electrical communication. The present invention demonstrates a unique and novel interaction between two different cell types which allows for the treatment and therapy of myocardial diseases and disorders.

Methods of Treating Cardiac Conditions

The present embodiments of the invention provide methods for correction of cardiac conduction disturbances and methods for treating cardiac conditions related to a cardiac conduction disturbance. These aspects of the present invention incorporates an advancement over standard cellular transplantation by increasing cell to cell communication, thus allowing for more synchronized contraction. The methods generally involve contacting a cardiac tissue of a host with a recombinant cell that expresses a connexin protein (e.g., Cx43), such that the connexin protein facilitates production of an electrical connection between the recombinant cell and the cardiomyocyte. The connection facilitates correction of a cardiac conduction disturbance by improving conduction in the heart. In embodiments of particular interest, the recombinant cell is a skeletal muscle cell.

The various therapeutic uses of connexin and related biologically active compounds or cells include uses in the treatment of a variety of different conditions in which an increase coordinated conduction of cardiomyocytes is desired. Exemplary diseases amenable to treatment by such methods include, but are not limited to, complete heart block, reentrant arrhythmias (e.g., ventricular tachycardia) congestive heart failure, and the like. Any cardiac disease or disorder that would benefit from improved synchronized contraction is amenable to treatment with these methods of local enhancement or delivery of connexins, or biological equivalents thereof, to affect cellular gap junctions.

Implantation Of Recombinant Connexin Cells

The following is a description of exemplary implantation techniques for connexin expressing cells, which description is not intended to be limiting, in particular in the context of other delivery methods provided according to other embodiments herein, and such other delivery techniques are to be considered in combination with the description of the present embodiments, as well as independently viable, as would be apparent to one of ordinary skill.

The transplantation of recombinant connexin cells into the myocardium of a subject can use well known surgical techniques for grafting tissue and/or isolated cells into a heart. In general, there are two methods for introducing the recombinant cells into the subject's heart tissue:1) surgical, direct injection; or 2) percutaneous techniques as describe in U.S. Pat. No. 6,059,726 (Lee and Lesh, "Method for locating the AV junction of the heart and injecting active substances therein").

The recombinant connexin cells can be implanted into any area of the heart where conduction disturbances have occurred. The amount of recombinant cells to be transplanted is determined by the type of heart disease being treated, the overall damage of myocardial tissue and the level of connexin expression in the cells to be transplanted. Of particular interest with respect to cardiac stimulation aspects of the invention, the cells are delivered into a region of heart tissue to be stimulated, or to enhance propagation of such stimulation, including in particular in the inter-ventricular septum such as for use in septal pacing. Accordingly, where "damaged" heart tissue is referenced, such description is herein intended to further apply to such regions of tissue to be stiimulated, though those particular regions may not themselves be damaged (but the stimulation thereof will be effective in treating conditions related to other damage).

In certain embodiments, the recombinant connexin-expressing cells are transplanted by percutaneous methods. If the site of the damaged heart tissue can be accurately determined in a subject by non-invasive diagnostic techniques, the recombinant connexin cells can be injected directly into the damaged myocardial tissue using general methods for percutaneous injections into cardiac muscle well known in the art, and further with respect to the novel, beneficial delivery embodiments provided herein. The amount of recombinant cells necessary to be therapeutically effective will vary with the type of disorder being treated as well as the extent of heart damage that has occurred.

Immunosuppressants may be used in conjunction of transplantation of Cx43-overexpressing cells not derived from the host to minimize the possibility of graft rejection, e.g., allogeneic or xenogeneic cells.

Combination with Other Therapies

The methods of the subject invention may also be utilized in combination with other cardiac therapies when appropriate. In certain embodiments, drugs used to treat certain types of conduction defects can be administered in combination with implanting recombinant connexin cells into the damaged myocardium (e.g., prior to, during and/or after implantation). Cardiac drugs that are suitable for use in combination therapy with connexin or other gap junction enhancement methods include, but are not limited to, growth factors, polynucleotides encoding growth factors, angiogenic agents, calcium channel blockers, antihypertensive agents, antimitotic agents, inotropic agents, antiatherogenic agents, anti-coagulants, beta-blockers, anti-arrhythmic agents, antiinflammatory agents, vasodilators, thrombolytic agents, cardiac glycosides, antibiotics, antiviral agents, antifungal agents, agents that inhibit protozoans, antiarrhythmic agents (used for treatment of ventricular tachycardia), nitrates, angiotensin converting enzyme (ACE) inhibitors; brain natriuretic peptide (BNP); antineoplastic agents, steroids, and the like.

Connexin or other gap-junction enhancement may also be a supplemental procedure to coronary artery bypass grafting (CABG). Replacement of a non-functioning myocardial scar with functioning muscle together with revascularization improves myocardial performance more than revascularization (bypass surgery) alone. Transplantation of recombinant connexin cells in conjunction with CABG provides for additive treatment during surgery by preventing the continued myocardial remodeling by reducing wall stress and ischemic burden. Additional surgical procedures to deliver the recombinant cells into the myocardium can be avoided by implanting the recombinant cells at the time of CABG surgery.

Assessment of Therapy

The effects of therapy according to the connexin or other gap junction enhancement methods can be monitored in a variety of ways. Generally for heart block disorders, such as related to various of the embodiments of the present invention, an electrocardiogram (ECG) or holter monitor is utilized to determine the efficacy of treatment. The contraction of the heart occurs due to electrical impulses that are generated within the heart; an ECG is a measure of the heart rhythms and electrical impulses. Thus ECG is a very effective and non-invasive way to determine if therapy has improved or maintained, prevented, or slowed degradation of the electrical conduction in a subject's heart. The use of a holter monitor, a portable ECG that can be worn for long periods of time to monitor heart abnormalities, arrhythmia disorders, and the like, is also a reliable method to assess the effectiveness of therapy.

Electrophysiology tests which involve percutaneous placement of catheters within the heart to assess the conduction properties of the heart, can also be used to assess therapy.

Where the condition to be treated with connexin or related bioactive agent delivery is congestive heart failure, an echocardiogram or nuclear study can be used to determine improvement in ventricular function. Comparison of echocardiograms prior to and after the grafting of recombinant connexin cells into myocardial tissue allows for reliable assessment of treatment.

The above methods for assessing the efficacy of therapy are only exemplary and are not meant to be limiting. Many appropriate assays for detecting synchronized coupling, (e.g., by monitoring cardiac function) are well known in the art and can be adapted for use.

EXAMPLES

The following examples are put forth so as to provide those of ordinary skill in the art with a complete disclosure and description of how to make and use the present embodiments of the invention, and are not intended to limit the scope of what is regarded as the invention nor are they intended to represent that the experiments below are all or the only experiments performed, or that they are the only methods or treatments that are capable of being performed based upon this disclosure and without undue experimentation according to one of ordinary skill in the art. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Characterization of Skeletal Myoblasts/Myotubes Ability to Electrically Excite Cardiac Tissue Tissue engineering techniques are attractive alternatives to conventional therapies for the treatment of end stage heart disease and conduction abnormalities. Cell transplantation offers the promise of restoring function to patients.

Biopsied skeletal muscle have satellite cells, skeletal myoblasts, which are able to divide and multiply. Skeletal myoblasts initially express Cx43. However, as the cells mature and differentiate into myotubes (the basic unit which leads to the contractile muscle fiber), Cx43 expression is the least in the skeletal myotubes.

Skeletal myoblasts and myotubes have different cellular electrophysiological characteristics. Characterization of the action potential parameters during different periods of myoblasts differentiation to myotubes were determined. Skeletal myoblasts were isolated by enzymatic dispersion from the hind limb muscle of 2-5 day old neonatal rats. Myoblasts were differentiated into multinucleated myotubes in culture by replacing the growth medium with differential medium (DM). (98% DMEM, 2% horse serum (HyClone), penicillin G 100 U/ml and streptomycin 100 µg/ml). Myoblasts and myotubes incubated in DM 2-14 days were studied. Whole cell configuration of patch clamp technique was used to record action potentials. The following measurements were obtained: resting membrane potential (RMP), action potential amplitude (APA), action potential duration at 50% ($APD_{50}$) repolarization (Table 1).

Myoblasts began to differentiate into multinucleated myotubes in 4 days and form a network of spontaneously contractile fibers by 10-14 days.

TABLE 1

Change of action potential parameters during different days in DM

| Group | RMP (mV) | APA (mV) | Vmax (V/s) | Threshold (nA) | $APD_{50}$ (ms) |
|---|---|---|---|---|---|
| DM 2 (n = 10) | −27.4 ± 2.9 | 60.1 ± 5.8 | 27.4 ± 4.2 | 31.1 ± 6.5 | 15.1 ± 1.7 |
| DM 4 (n = 4) | −38.3 ± 3.6 | 94.4 ± 6.5 | 72.2 ± 6.7 | 23.8 ± 2.39 | 8.1 ± 0.1 |
| DM 6 (n = 8) | −50.6 ± 3.0 | 113.9 ± 3.4 | 102.9 ± 9.0 | 18.1 ± 0.9 | 7.4 ± 0.5 |
| DM 8 (n = 11) | −52.8 ± 1.8 | 123.7 ± 4.3 | 123.5 ± 6.4 | 17.2 ± 1.9 | 7.4 ± 0.4 |
| DM 10 (n = 7) | −53.1 ± 2.5 | 133.1 ± 2.7 | 153.4 ± 8.9 | 29.2 ± 5.3 | 7.4 ± 0.5 |
| DM 11 (n = 10) | −53 ± 1.7 | 133.5 ± 3.1 | 146.4 ± 2.9 | 33 ± 2.8 | 5.1 ± 0.5 |
| DM 12 (n = 9) | −52.4 ± 3.2 | 127.4 ± 2.9 | 142.7 ± 6.4 | 30.7 ± 6.8 | 5.4 ± 0.7 |
| DM 13 (n = 9) | −48.8 ± 3.1 | 120.6 ± 3.0 | 129.3 ± 6.8 | 30 ± 4.9 | 7.5 ± 0.6 |
| DM 14 (n = 9) | −46.8 ± 0.9 | 120.2 ± 5.4 | 114.6 ± 3.9 | 43.3 ± 4.3 | 6.4 ± 0.6 |

Freshly isolated skeletal myoblasts did not have measurable action potentials and were unable to be electrically stimulated.

RMP: There was no significant difference between days 8 and days 10-14.

APA: With the RMP of myotube becoming more negative during development, the amplitude of action potential also increased and reached to a peak value at 10-11 days. Then, APA decreased in parallel until 13-14 days. No significant difference was found between day 10 and day 8, day 11-14.

Vmax: similar changes were noticed as that of APA.

$APD_{50}$: The minium value of $APD_{50}$ occurred at 11-12 days and then increased. There was no significant among each group except day 2.

Thus, action potential parameters change during different periods of myoblasts differentiation to myotubes.

The patch clamping data highlights the relative electrical inexcitability of myoblasts in DM less than 7 days. According to these results, transplanted skeletal myoblasts/myotubes generally will not propagate sufficient electrical impulses to enhance inter-cellular conduction unless there is enhanced cellular coupling via gap junctions.

Computer modeling was used to assess cell to cell electrical excitation between skeletal myoblasts and myofibers with cardiac myocardial cells (Lee R et al., Annals of Biomedical Engineering 28-1:S54, 2000). The modeling was performed by incorporating measured cellular parameters of each cell's type. The computer modeling results determined that the action potential duration (APD) of skeletal cells is short (1.6 ms and 2.8 ms for myoblast and myofiber, respectively), as compared to the cardiac cell, and is the major limitation of skeletal-to-skeletal and skeletal-to-cardiac excitation. A high degree of intercellular coupling was required for skeletal cells to excite their downstream neighbors quickly enough, within 2.5 ms, prior to their own repolarization. The cardiac APD is long (178 ms) and there was a long length of time for cardiac cells to charge their downstream neighbor, before the charging cell repolarizes. Decreasing intercellular coupling increased the time necessary to charge adjoining cells. The ratio of intercellular coupling reduction to still allow cell-to-cell excitation in homogeneous strands was 45:5:1 for the ventricular, skeletal myoblast, and skeletal myofiber cell types, respectively. In mixed strands, the limiting factor in excitation was any instance that the skeletal cell was the source cell.

These results demonstrate that: 1) the short skeletal action potential limits skeletal to cardiac conduction by limiting the capacity to provide a sufficient excitation charge to cardiac cells; 2) skeletal myoblast differentiation into myofibers further limits excitation capacity; 3) very high levels of gap-junction coupling are needed for successful skeletal to cardiac conduction.

Thus, conditions which decrease intercellular coupling will markedly decrease electrical transmission between transplanted skeletal cells and the adjoining myocardium. Electrical conduction slowing or block can lead to potential life threatening arrhythmias.

Example 2

Electrophysiologic Consequences of Skeletal Muscle Transplantation

To assess the electrophysiologic consequences of skeletal muscle transplantation into the myocardium, an in vivo model to assess cardiac conduction was used. The feasibility of gene transfer to specific areas of the cardiac conduction system has been previously demonstrated (Lee et al. 1198 PACE 21-II: 606; Gallinghouse et al. November 1996 Am Heart Assoc.; U.S. Pat. No. 6,059,726). For example, the highly efficient and specifically localized expression of recombinant beta galactosidase in the AV node of rats and pigs has been described. The accuracy and reproducibility of AV nodal injections has been validated by the production of AV block in rats (Lee et al. 1998 J Appl Physiol. 85(2): 758-763). As an electrically insulated conduit for electrical transmission between the atrium and the ventricle, the AV conduction axis is in a strategic position for the study of cardiac electrophysiology.

To determine whether skeletal muscle transplantation alters conduction on AV nodal electrophysiologic properties, a rat model for AV node injections was utilized (Lee et al. 1998 J Appl Physiol. 85(2): 758-763). Animals were chemically denervated (using atropine and propranolol to inhibit the influence of autonomic nervous system) and studied with right atrial overdrive pacing and atrial programmed extrastimulation, both pre-injection and at the time of sacrifice. Surface ECG PR intervals were measured, together with AV nodal block cycle length (AVBCL) (the rate at which AV conduction becomes sequentially longer, then fails to conduct) and effective refractory period (ERP) (the coupling interval at which an atrial extrastimulus fails to conduct through the AV node). A single injection of skeletal myoblasts ($1 \times 10^5$, 15 ul) or vehicle was injected into the AVN of rats (n=8).

Electrophysiologic properties of the AV junction were significantly altered in animals with transplantation of skeletal myoblasts. Significant alterations in the Wenkebach cycle length (70.0±4.4 vs 57.0±5.0 msec; p<0.01) and AV nodal refractory period (113.8±5.6 vs 87.0±6.2 msec; p<0.005) were recorded in the skeletal myoblast injected rats as compared to control animals. Histological examination of the AVN revealed that approximately 10% of the AVN was involved with minimal to no inflammation. Histologically the AV conduction axis appeared normal in control vehicle injections. Interestingly, the PR interval did not significantly change, reflecting the insensitivity of surface EKG markers for cardiac conduction properties.

These results add further evidence that transplanted skeletal myoblasts (even when involving a small portion of the AVN) alters cardiac conduction and may lead to areas of slow conduction or conduction block. Therefore, as the skeletal myoblasts differentiate into myotubes and lose their ability to form gap junctions, the ability to propagate electrical impulses decrease.

Examples 3-7

Methods and Materials

The following materials and methods were utilized for Examples 3-7.

Skeletal Myoblast Isolation and Culture

This protocol was approved by the Committee on Animal Research, University of California at San Francisco and conducted in accordance with federal guidelines. Neonatal skeletal myoblasts were isolated as previously described by enzymatic dispersion from 2-5 days old C3H neonatal mice and cultured as previously described (Rando, T., and Blau, H. M. (1994), J. Cell Biol. 125, 1275-1287). After isolation, cells were cultured with growth medium (GM) (80% F-10 medium (GIBCO BRL), 20% FBS (HyClone Laboratories, Inc.), penicillin G 100 U/ml and streptomycin 100 ug/ml, bFGF 2.5 ng/ml (human, Promega Corp)). Skeletal myoblasts were maintained in GM medium in humidified 95% air and 5% $CO_2$. Once the cultures achieved 75% confluency (day 0), the myoblasts were cultured in either GM medium or changed to differential medium (DM) (98% DMEM, 2% horse serum (HyClone), penicillin G 100 U/ml and streptomycin 100 ug/ml). Myoblasts cultured in DM were incubated in humidified 95% air and 10% $CO_2$. Myoblasts were collected on day 0, day 2, day 4, day 7, respectively for extraction of RNA and protein.

Production of Connexin 43

The rat connexin 43 (Cx43) cDNA was cloned into the MFG retroviral vector; and transduced into murine myoblasts as previously described (Springer M L, Chen A S, Kraft P E, Bednarski M, Blau H M., Molecular Cell. 1998, 2:549-558). This vector has been shown to be stably expressed in muscle (Dhawan J, Pan L C, Pavlath G K, Travis M A, Lanctot A M, Blau H M, Science 1991:254, 1509-1512). Primary myoblasts already expressing the *E. coli* β-galactosidase (β-gal) gene (TR/Z) was used as control myoblasts (Springer, M. L., and Blau, H. M., Som. Cell Mol. Genet. 1997:23, 203-209).

Determination of mRNA Levels Using RT-PCR

RNA from the cultured cells was prepared using the Qiagen Kit, Qiagen, Inc. CA, and quantified by spectrophotometry (A260 and A280 measurements). RNA (1 ug) of each sample was reverse-transcribed for 1 hour at 37° C. using Olig-dT and the same amount of cDNA was amplified for connexin 43, myogenin, myoD, desmin and GAPDH, respectively. The different primers used in this study were described in Table 2. After denaturing at 94° C. for 5 minutes, amplification was performed for certain cycles (94° C. for 30", 55° C. for 30" and 72° C. for 30"), followed by 72 cycles for another 5 minutes. The optimal cycles to semi-quantify the product for GAPDH and connexin 43 were 25; and for myogenin, myoD and desmin were 22. The PCR products were resolved by electrophoresis on 2% agrose gel and analyzed by densitometry with NIH software. The levels of connexin 43, myogenin, myoD, and desmin expression were normalized to the level of GAPDH; and the level of day 0 was set as 1.

TABLE 2

Summary of Primers utilized in Experimental studies:

| Genes | Primer(Forward) | Primer(Reverse) |
|---|---|---|
| Connexin 43 | 5'-TACCACGCCACCACCGGCCCA-3' | 5'-GGCATTTTGGCTGTCGTCAGGGAA-3' |
| Myogenin | 5'-CCTTAAAGCAGAGAGCATCC-3' | 5'-GGAATTCGAGGCATAATATGA-3' |
| MyoD | 5'-TTCTTCACCACACCTCTGACA-3' | 5'-GCCGTGAGAGTCGTCTTAACTT-3' |
| Desmin | 5'-CCGGAGGCTTGGGGTCGCT-3' | 5'-CTGTTCCTGAAGCTGGGCCGTGG-3' |
| GAPDH | 5'-AAAGTGGAGATTGTTGCCAT-3' | 5'-TTGACTGTGCCGTTGAATT-3' |

Detection of Protein Expression with Western Blotting

The total soluble protein was extracted from the cultured cells and was quantified by Bradford method. The soluble proteins (40 µg) were separated via SDS-PAGE using a 10-20% resolving gel for connexin 43, MHC, P21 detection. Proteins were electroblotted to HYBOND™-ECL nitrocellulose membrane and immunoreactions were carried out as described using the ECL detection kit. Connexin 43 was detected using as anti-connexin 43 rabbit polyclonal antibody (Zymed Laboratories, Inc. Ca.) (1:1000). Myosin heavy chain protein was detected with Mf-20 antibody (Developmental studies hybridoma bank, University of Iowa) (1:2000 dilution). P21 protein was detected with P21 antibody (Chemicon international, Inc. Cz.) (1:500 dilution).

Immunofluoresence Analysis

Immunofluorescence method for connexin 43, MHC, Desmin were performed as described by Tomakidi P, Cheng H, Kohl A, Komposch G, Alonso A, Cell Tissue Res, 2000;301(2):323-327. Briefly, myoblasts were plated on chamber slides with GM medium. At 70-80% confluence, the medium was either maintained in GM or switched to DM. Cells were collected on day 0, day 2, day 4 and day 7. After fixation with 4% paraformaldehyde in PBS and post fixative permeabilization with 0.2% triton X-100/PBS, cells were blocked with 3% BSA for 1 hour and incubated with primary antibody at room temperature for 1 hour. After washing with PBS three times, FITC-conjugated secondary antibody were used for incubation 1 hour. The dilution for Desmin antibody (Sigma, St. Louis, Mo.), connexin 43 (Zymed Laboratories, Inc. Ca.) and MF-20 (Developmental studies hybridoma bank, University of Iowa) were 1:100, 1:100 and 1:50, respectively.

Microinjection Technique

Gap junctions were evaluated by microinjecting cells with the gap junction permeable dye, Lucifer yellow (Molecular Probes, Or.). Microinjection was performed in: 1) control (TR/Z) and CX43 myoblasts at 70-80% confluency, 2) TR/Z and CX43 myotubes and 3) co-cultured adult rat cardiomyocytes (ARC) and adult skeletal myoblasts or myotubes. The dye solution was composed of 2% Lucifer yellow (gap junction permeable) and 1% tetramethylrhodamine-dextran (gap junction impermeable; Molecular Probes) in sterile distilled water. Microinjection was performed with Micromanipulator 5171, FemtoJet, Eppendorf by a pulse pressure of 80 hpa of 0.3 second of duration through a 0.5±0.2 μm tip micropipette (Femtotips, Eppendorf). Cultured cells were washed and the medium was replaced with phosphate-buffered saline (PBS) containing 10% FBS. Injections were done with Nikon TE300 Microscope with phase and fluorescence optics.

Example 3

Expression of Gap Junction Proteins

Connexin 43-encoding nucleic acid was introduced into skeletal muscle cells as described above. The formation of functional gap junctions between recombinant Cx43-expressing myoblasts or recombinant Cx43-expressing myoblasts which have differentiated into myotubes with other types of myoblasts or myotubes was evaluated. A control (TR/Z) myoblast cell, which expresses Cx43 initially and then down regulates Cx43 expression during differentiation into myotubes was utilized as a control for functional gap junctions and dye transfer in control myoblast but not in control myotubes.

The Cx43 mRNA (FIGS. 2A and B) and protein changes (FIGS. 2C and D) in control cells and Cx43 cells were observed. An electrophoresis agarose gel of RT-PCR experiments indicated the mRNA Cx43 levels of control cells (TR/Z) and recombinant Cx43-expressing cells at day 0, 2, 4 and 7. The average level of Cx43 mRNA was determined by RT-PCR for three control samples and three recombinant Cx43-expressing cell samples at day 0, 2, 4 and 7. The connexin 43 mRNA levels were significantly down-regulated by day 7 in TR/Z control (untransformed) skeletal myotubes while in contrast, the Cx43-modified cells exhibited no significant difference in Cx43 mRNA expression between day 0 and day 7, indicating that retroviral transduction with the connexin 43 gene was accomplished and Cx43 was expressed in mature myotubes unlike control myotubes (Day 7).

The Cx43 protein levels associated with the same cells analyzed for Cx43 mRNA were also observed. A western blot for Cx43 protein indicated the relative amounts of Cx43 protein present in control cells and recombinant Cx43-expressing cells at day 0, 2, 4 and 7. Cx43 western blotting experiments were used to determine the relative amount of Cx43 protein in three control cell samples and three Cx43 expressing cell samples at day 0, 2, 4 and 7. Protein expression results were consistent with the RT-PCR results confirming that expression of recombinant Cx43 can rescue connexin 43 loss in control cells at day 7. The RT-PCR results demonstrate Cx43 mRNA levels as expected, in control cells were gradually down and almost absent at day 7 while the level of Cx43 mRNA for recombinant CX43 expressing cells was unchanged through day 0 to day 7. GAPDH was utilized as an internal control in these RT-PCR studies. Western blotting with antibodies for Cx43, in control cells showed that CX43 expression was downregulated at day 2 and almost absent after day 4 (during myotube formation) while recombinant Cx43-expressing cells did not show any downregulation, and even upregulation could be detected at day 7. No differences in N-cadherin mRNA and protein expression levels were found in skeletal myoblasts before or after differentiation.

Microinjection studies to investigate the formation of functional gap junctions were completed on control cells (myoblast and myotubes) and recombinant Cx43-expressing cells (myoblasts and myotubes). Injected cells were labeled with rhodamine dextron and Lucifer Yellow, Lucifer yellow being capable of transfer from one cell to another through functional gap junctions. Phase contrast panels indicated the injected cell in each set of experiments. A microinjection study between skeletal myoblasts or myotubes indicated the relative transfer of Rhodamine or Lucifer yellow dyes. The cells of interest were observed under phase contrast microscopy and appropriate fluorescence illumination for either Rhodamine or Lucifer yellow fluorescent dyes. Observations were made regarding control myoblasts which express Cx43, contacting other control myoblasts; Cx43 myoblasts coupled to Cx43 myoblasts; and control myotube (no Cx43 expression) to control myotube; and Cx43 myotube to Cx43 myotubes.

These microinjection studies revealed that in skeletal myoblasts, dye transfer (Lucifer yellow) could be observed in both control (TR/Z) and Cx43 myoblasts. After 7 days in culture with DM media, no dye transfer could be observed in myotubes formed from control myoblasts. Dye transfer persisted in Cx 43 transduced skeletal cells placed in differentiation media for 7 days. In summary, these microinjection experiments showed that dye transfer occurred in Cx43 transduced skeletal myoblasts placed in differentiation media and not in control myotubes.

Example 4

Gap Junction Function and Co-culture Experiments

To evaluate gap junction formation between myoblasts and cultured adult rat cardiomyocytes (ARC), single adult rat cardiac ventricular myocytes were enzymatically isolated from female Sprague-Dawley rats weighing 200-250 g by standard methods. Briefly, following intraperitoneal anesthesia (pentobarbtal 100 mg/kg), the rat heart was rapidly excised and perfused retrogradedly via the aorta using the Langendorff technique. The perfusion was performed at 37° C. using solution A (norminal $Ca^{2+}$ free solution, NaCl 134 mM, KCl 5.4 mM, Hepes 10 mM, glucose 10 mM, $MgCl_2$ 1 mM, $NaH2PO4$ 0.33 mM, titrated to pH 7.4 with NaOH.) for 5 min, solution A, 0.1 mM $CaCl_2$ with 1 mg/ml collagenase (Type B, Boehringer Mannheim, Germany) for about 15 min consequently, then washout with solution A and $CaCl_2$ 0.2 mM for 5 min. Afterwards the left ventricle was removed and chopped into small pieces, which were incubated with 20 ml solution A and 0.1 mM $CaCl_2$ with shaking at 37° C. for 10 min in a glass conical flask. The cell suspension was filtered (200 micron mesh) and the filtrate was sedimented for 5 min. The $Ca^{2+}$ concentration of the supernatant was gradually increased with 1 mM $Ca^{2+}$-containing solution till 0.5 mM final concentration. ARC were grown in HAM-F-12/M199 (1:1) supplemented with 10% FBS, penicillin G 100 U/ml and streptomycin 100 μg/ml in laminin-coated dishes at densities of $10^4$ rod-shaped cells $cm^{-2}$.

In serum-containing medium, ARC undergo a morphological change described as dedifferentiation/redifferentiation, hallmarked by the loss of the rod shape and myofibrillar disintegration and subsequent spreading, and reorganization of the contractile apparatus. On day 3, cytosine arabinouranoside (5 μM) was added to prevent fibroblasts overgrowth. Most of the ARC were redifferentiated by day 7 and contractile activity was observed. After completion of differentiation/redifferentiation, skeletal myoblasts ($10^4$/cm2) were added to the ARC cultures. They were kept in the HAM-F-12/M199 medium for overnight and microinjection was performed next day to evaluate dye transfer between myoblast and ARC. To induce myotubes formation, the medium was changed to DM and microinjection was performed after myotubes formation (7 days).

Microinjection studies to investigate the formation of functional gap junctions between cardiomyocte cells and control cells (skeletal myoblast and myotubes) or with recombinant Cx43-expressing cells (skeletal myoblasts and myotubes) were completed. Injected cells were labeled with rhodamine dextron and Lucifer Yellow, Lucifer yellow being capable of transfer from one cell to another through functional gap junctions. The injected cell in each set of experiments were observed. In co-culture experiments, dye transfer could be observed between adult rat cardiomyocytes (ARC) and control myoblast which express Cx43 or with Cx43 myoblasts. Even after 7 days in differentiation culture, Cx43 cells were capable of dye transfer with ARC, indicating functional gap junctions. In contrast, there was no dye transfer between control skeletal myotubes and ARC. In summary, these experiments indicate the unique and novel features of the present invention by demonstrating that it is possible to form functional gap junctions between two different cell types by expressing a recombinant connexin in one of the cells. In particular, that functional gap junctions can be formed between adult skeletal muscle cells modified to over express Cx43 and cardiomyocytes.

Example 5

Effects of Connexin 43 Expression on Skeletal Myoblasts Differentiation

To determine the effect of Cx43 expression on the differentiation of skeletal myoblasts, expression levels of other proteins were analyzed. An Immunofluorescence study was performed analyzing the expression levels of MHC and Desmin, two strong markers for myoblast differentiation into myotubes, in control and Cx43 cells. Control skeletal myoblasts differentiated into multinucleated myotubes after incubation with DM for 7 days. In the Connexin 43 group, myotubes did not form even after 14 days in DM. Clearly, expression of recombinant Cx43 prevented myoblasts from forming myotubes. Immunofluorescence studies demonstrated that MF-20 (MHC) and Desmin, two strong markers for myoblast differentiation into myotubes, were present at day 7 in control samples and absent in the CX 43 expressing samples. MF-20 expression from western blotting study was consistent with the immunofluorescent study. P21 expression, marker of cell mitosis arrest, had consistent changes among these groups and was up-regulated gradually from day 0 to day 7, which reflects that both TR/Z and Cx43 cells withdraw from dividing when medium was switched to DM.

To determine whether the expression of recombinant connexin 43 is harmful to myotubes or is only deleterious during differentiation from myoblasts to myotubes, skeletal myoblasts and myotubes were transfected with a replication-deficient adenovirus with the Cx43 gene (Ad Cx43). Myoblasts transfected with Ad Cx43 and transferred to differentiation media had impaired myotube formation. In contrast, fully differentiated myotubes transfected with Ad Cx43 remained normal appearing and aligned themselves in an orderly array analogous to control myotubes. Transfection with control adenovirus without Cx43 developed normally.

Example 6

Cx 43 Expression in Skeletal Muscle Improves Electrical Conduction in the AV Node To determine whether the forced expression of connexins improve cardiac conduction, skeletal muscle cells were transduced with Cx 43 (same cells as used in in vitro experiments) and injected into the AV node of immunodeficient rats (Lee et al. 1998 J Appl Physiol. 85(2): 758-763). Animals injected with Cx 43 transduced skeletal myoblasts ($2.5 \times 10^6$ cells/25 μl; n=8) were compared to animals injected with control skeletal myoblasts ($2.5 \times 10^6$ cells/25 μl; n=5). Surface ECG PR intervals were measured, together with AV nodal block cycle length (AVBCL) (the rate at which AV conduction becomes sequentially longer, then fails to conduct) and AVN effective refractory period (AVN ERP) (the coupling interval at which an atrial extrastimulus fails to conduct through the AV node).

Significant shortening of the PR interval was observed in the animals injected with Cx43 transduced skeletal myoblasts as compared to the control skeletal muscle cell injected animals (40.6±1.9 ms vs 47.6±2.5 ms; p<0.0001, paired T-test). The AVBCL (96.7±10 ms vs 112.0±11.0 ms; p<0.03, paired T-test) and AVN ERP (80.0±9.2 ms vs 100.0±16.0 ms; p<0.001, paired T-test) were significantly improved in animals injected with Cx43 transduced skeletal myoblasts as compared to animals injected with control skeletal myoblast These results demonstrate that the electrical conduction through the AV junction was significantly improved in animals injected with Cx43 transduced skeletal myoblasts as compared to control skeletal myoblasts. Thus connexin production in the recombinant cells provided for electrical connection between the recombinant cells and adjoining myocardial cells, which in turn would provide for better electromechanical synchrony between the atria and the ventricle.

Example 7

Autologous Transplantation of Cx43-Expressing Cells in Patients with a Previous Myocardial Infarction The treatment of cardiomyopathy in humans is carried out as follows. A muscle biopsy is obtained from patients who have experienced anterior, lateral or inferior wall myocardial infarction and may or may not be a patient that requires coronary artery bypass graft (CABG) surgery. The skeletal muscle cells gathered from the biopsy are cultured ex vivo and genetically modified to express a human connexin (such as Cx43) by the methods described above. The modified skeletal muscles are analyzed for recombinant connexin expression by immunofluorescence assay for connexin protein. In certain instances, the cells are analyzed for the ability to form functional gap junctions with cardiomyocyte cells by the in vitro Lucifer dye assays described above.

After analysis of the modified muscle cells, a therapeutically effective amount of the modified muscle cells are implanted into the patients heart tissue. In certain instances when the patients own skeletal muscle cells cannot be used for cardiac treatment, a recombinant muscle cell line which expresses recombinant human Cx43 is utilized in conjunction with the appropriate use of immunosuprression drugs known to those skilled in the art. The Cx43 expressing muscle cells are then implanted endovascularly with a injection catheter, which catheters can be obtained from a variety of sources (e.g., injectable catheters such as Johnson & Johnson's NOGA system, BioHeart's Myocath, Biocardia, Boston Scientific's stilleto, Transvascular catheter, and the like) or with a hypodermic syringe for a CABG procedure. The patient is monitored after surgery to evaluate the efficacy of treatment.

Patients

The patients are males and females generally between 18 and 75 years of age with the diagnosis of previous myocardial infarction or non-ischemic cardiomyopathy.

Biopsy

The skeletal muscle biopsy is obtained within a few weeks (e.g., 3-4 weeks) of anticipated coronary artery bypass for patient where the procedure is warranted. Autologous skeletal muscle cells (myoblasts and myotubes) are isolated from the skeletal muscle biopsy. Under sterile surgical conditions, an open biopsy technique is utilized to excise skeletal muscle from the muscle belly. The biopsy is obtained from the thigh (Quadriceps-vastus lateralis) or the mid-calf (Gastrocnemius) of the patient. An attempt is made to exclude contaminating fascia from the biopsy.

Quadriceps-vastus lateralis—An incision is made longitudinally along the anterolateral aspect of the thigh in the lower third of the thigh. Dissection is carried through the soft tissue and fascia and the quadriceps vastus lateralis will be identified and exposed. A segment of muscle is resected longitudinally along the long axis of the muscle fiber and placed into a container of transport medium.

Gastrocnemius—An incision is longitudinally in the posterolateral gastrocnemius area in the mid calf. Dissection is made through to the deep fascia to expose the gastrocnemius muscle. A segment of muscle is resected longitudinally along the long axis of the muscle fiber and placed into a container of transport medium.

Ex Vivo Propagation and Genetic Modification of Autologous Cells

The methods and protocols used for the isolation, expansion and transduction of the autologous skeletal muscle cells with a human connexin construct ex vivo are as described above. For example, human connexin (e.g., Cx43) cDNA is cloned into the MFG retroviral construct and transduced into the autologous skeletal mucslce cells in a similar manner as described by Springer ML et. al., Molecular Cell. 1998, 2:549-558. This construct is generally stably expressed in the autologous muscle cells.

The genetically modified cells are cultured so as to provide for a concentration of about $10^6$-$10^9$ cells/ml. The modified cells may be stored under refrigeration (usually around 0° C.) prior to transplantation into the patient. Cell viability via Trypan Blue Dye Exclusion can be used as a cell viability assay. Potency is confirmed via the detection of Cx43 expression by immunofluorescence and/or by the functional gap junction assays described above.

Implantation of Recombinant Connexin Expressing Cells via a Percutaneous Approach Implanting the recombinant connexin expressing cells into the myocardium involves administering the recombinant cells by using a catheter delivery system. The recombinant cells are injected into the akinetic myocardial scar at the site of a previous infarct. Depending on the size of the targeted infarct zone, between 400 million and 1 billion cells are injected as a suspension. Multiple injections can be used to deliver the recombinant cells.

The injections are carried out by advancing the needle through the end hole of the catheter to a predetermined depth. The proximal end of the needle lumen is attached to a calibrated syringe that contains the recombinant cell suspension. After adequate positioning against the endocardial surface by fluoroscopic, intracardiac echocardiography or magnetic resonance imaging guidance, the needle is advanced into the myocardium and the cell suspension is injected. Upon completion of the injection, the needle is withdrawn into the catheter. This method is repeated in the target region until transfer of the cells is complete. An attempt is made to cover the entire area of the scar, including its periphery. If the cellular therapy is delivered during a CABG, then a needle and syringe are used to epicardially deliver the cells to the akinetic region as described above.

Monitoring and Evaluation of Treatment

Clinical status, adverse events, 12-lead electrocardiogram, 24 hour ambulatory electrocardiogram, and routine clinical laboratory tests are carried out by methods and techniques known to those skilled in the art for the evaluation of regional left ventricular wall function. Follow-up can be performed and compared to baseline (i.e., prior to treatment) at selected periods post-implantation (e.g,. 1, 2, 3, 4, 6, and 12 months). In certain instances, evaluation of treatment may include Dobutamine stress echocardiographic evaluation of regional wall motion and wall thickness in region of implantation (infracted region), contrast ventriculography or magnetic resonance imaging. The monitoring and evaluation post treatment can be used to determine the level of regeneration of functional muscle and synchronized electromechanical conduction within the infarct.

Example 8

Autologous Transplantation of Recombinant Cx43-Expressing Cells in Patients with Cardiac Conduction Disease Patients The patients are males and females between 1 and 90 years of age with the diagnosis of cardiac conduction disease (i.e., heart block). The heart block can be congenital, acquired, iatrogenic (e.g., as a complication of valve surgery or catheter ablation) or part of the normal aging process. Utilizing the methods described in Example 7, 1-100 million modified cells can be injected in the AV node region in a volume of 0.2-0.5 ml. The recombinant connexin cells can be delivered surgically via a 25 gauge syringe, via the AV nodal artery or via a percutaneous delivery system (see, e.g., U.S. Pat. No. 6,059,726.

Monitoring and Evaluation of Treatment

The detection of heart block (and its treatment) can be readily detected by surface ECG. Exercise stress testing, holter monitoring or an electrophysiology study are alternative supplemental tests to assess therapy.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A cardiac stimulation system, comprising:
   a cardiac stimulator assembly with an electrical energy source, and an electrical energy emitter that is adapted to be coupled to the electrical energy source and to be positioned within a region of a heart of a patient to be stimulated;
   means for enhancing electrical stimulation of the region with the electrical energy from the electrical energy emitter; and
   means for stimulating the septum of the heart, with the cardiac stimulator assembly and means for enhancing stimulation.

2. The system of claim 1, wherein the cardiac stimulation assembly comprises:
   a delivery member with a proximal end portion and a distal end portion that is adapted to be positioned at a location within a heart of a patient; and
   an array of extendable electrode assemblies cooperating with the delivery member and that each includes a stimulation electrode that is adjustable to extend from the delivery member at the location and into a unique location relative to the other extendable electrode assemblies within the region of tissue.

3. The system of claim 2, wherein each of the array of extendable electrode assemblies comprises an extendable needle that is adjustable to extend from the distal end portion of the delivery assembly and into cardiac tissue so as to position the respective stimulation electrode at the unique location.

4. The system of claim 3, wherein the stimulation electrode of each extendable electrode assembly is integrated with the needle.

5. The system of claim 3, wherein the stimulation electrode of each extendable electrode assembly is adjustable to extend from the respective needle to the unique respective location.

6. The system of claim 3, wherein the needle has a curved shape.

7. The system of claim 3, wherein the needle comprises a superelastic metal alloy.

8. The system of claim 3, wherein the needle comprises a shape memory metal alloy.

9. The system of claim 3, wherein the needle comprises a nickel-titanium alloy.

10. The system of claim 2, wherein:
    each of the array of extendable electrode assemblies comprises a relatively pliable tubular body with an inner lumen;
    each stimulation electrode is located along the tubular body of the respective extendable electrode assembly; and
    wherein each relatively pliable tubular body is adapted to be deflected and steered through the region of tissue so as to place the respective stimulation electrode at the respective unique location.

11. The system of claim 10, further comprising:
    a moveable stylet that is adapted to be moveably engaged within the inner lumen of at least one of the tubular bodies so as to adjust the tubular body to extend from the delivery member and advance through the region of tissue such that the respective stimulation electrode is positioned at the respective unique location.

12. The system of claim 11, wherein:
    the moveable stylet has a proximal end portion and a shaped distal end portion that is torquable within the inner lumen by torquing the proximal end portion proximally and externally of the tubular body so as to deflect and steer the tubular body in order to place the electrode.

13. The system of claim 2, further comprising:
    an anchor that is extendable from the delivery member and adapted to anchor the distal end portion at the location such that the array of extendable electrode assemblies is adapted to be positioned at the respective unique locations along the region of tissue.

14. The system of claim 13, wherein the anchor comprises a stimulation electrode.

15. The system of claim 14, wherein:
    the distal end portion of the delivery member comprises a distal tip; and
    a stimulation electrode is located at the distal tip.

16. The system of claim 1, wherein the cardiac stimulation assembly comprises:
    a cardiac pacemaker.

17. The system of claim 16, wherein the cardiac pacemaker comprises:
    a bi-ventricular cardiac pacemaker.

18. The system of claim 1, wherein the cardiac stimulation assembly comprises:
    a cardiac defibrillator.

19. The system of claim 1, wherein the conductive agent comprises isolated living cells.

20. The system of claim 19, wherein the living cells comprise at least one of myoblasts, fibroblasts, or stem cells.

21. The system of claim 19, wherein the living cells are adapted to express a connexin at gap junctions with cardiac cells in the region of tissue.

22. The system of claim 21, wherein the living cells are adapted to express connexin 43 at the gap junctions.

23. The system of claim 22, wherein the living cells are genetically modified to over-express production of connexin 43.

24. The system of claim 1, wherein the conductive agent comprises an injectable preparation of a conductive non-living material that is adapted to enhance electrical conduction in the region.

25. The system of claim 24, wherein the conductive non-living material comprises an injectable preparation of a conductive metal.

26. The system of claim 1, wherein:
the cardiac stimulation assembly comprises at least one electrical lead that is adapted to be positioned so as to emit electrical current into the region; and
the system further comprises a delivery assembly that is adapted to deliver the at least one electrical lead and also the volume of conductive agent to the region of tissue.

27. The system of claim 26, wherein the delivery member comprises:
a septal perforator delivery assembly that is adapted to couple the cardiac stimulation assembly to the region of tissue via at least one septal perforator vessel, and also to deliver the volume of conductive agent to the region via the at least one septal perforator vessel.

28. The system of claim 26, wherein the delivery assembly comprises:
a transcardiac delivery member.

29. The system of claim 1, wherein the means for enhancing electrical stimulation of the region comprises:
means for delivering a conductive agent to the region.

30. The system of claim 29, wherein the means for delivering a conductive agent to the region comprises:
means for producing a connexin, or analog, derivative, or biological equivalent thereof, in the region.

31. The system of claim 30, wherein the means for producing a connexin in the region comprises:
means for producing connexin 43, or analog, derivative, or biological equivalent thereof, in the region.

32. The system of claim 31, wherein the means for producing connexin 43 comprises:
means for genetically modifying cells that over-express connexin 43, or analog, derivative, or biological equivalent thereof, and
means for producing the connexin 43 in the region with the genetically modified cells.

33. The system of claim 1, wherein the means for stimulating the septum comprises:
means for pacing the heart from the septum.

34. The system of claim 33, wherein the means for pacing the heart from the septum comprises:
means for providing bi-ventricular pacing from the septum.

35. The system of claim 1, wherein the means for stimulating the septum comprises:
means for defibrillating the heart via the septum.

36. The system of claim 1, wherein the means for stimulating the septum comprises:
means for stimulating the septum via at least one septal perforator vessel.

37. A cardiac stimulation assembly, comprising:
an elongate body having a proximal end portion, a distal end portion that is adapted to be positioned at least in part at a location within a heart of a patient, and a delivery lumen extending at least in part along the distal end portion;
means for delivering electrical energy into a region of tissue within the heart of the patient;
means for enhancing stimulation of the region of tissue from electrical energy delivered from the means for delivering electrical energy; and
means for stimulating the septum of the heart with the cardiac stimulation assembly and means for enhancing stimulation;
wherein the means for delivering electrical energy and means for enhancing stimulation are adapted to cooperate with the elongate body.

38. The assembly of claim 37, wherein the means for delivering electrical energy into the region comprises:
means for delivering a stimulation electrode into the region.

39. The assembly of claim 38, wherein the means for delivering the stimulation electrode into the region comprises:
means for extending the stimulation electrode from a delivery catheter at a location within a cardiac chamber adjacent to the region and into the region.

40. The assembly of claim 39, wherein the means for extending the stimulation electrode comprises:
means for positioning the stimulation electrode at a location that is off-axis from the longitudinal axis from the distal end portion of the catheter adjacent the region.

41. The assembly of claim 37, wherein the means for delivering a stimulation electrode to the region comprises:
means for delivering an array of stimulation electrodes to the region.

42. The assembly of claim 41, wherein the means for delivering an array of stimulation electrodes to the region comprises:
means for positioning each of the stimulation electrodes at a unique respective position relative to the other stimulation electrodes within the region.

43. The assembly of claim 41, wherein the means for positioning each of the stimulation electrodes comprises:
means for extending a plurality of electroded members from a delivery member.

44. The assembly of claim 37, wherein the means for delivering a stimulation electrode to the region comprises:
means for delivering the stimulation electrode into a septal perforator vessel.

45. The assembly of claim 37, wherein the means for delivering electrical energy to the region comprises:
means for pacing the heart from the region.

46. The assembly of claim 45, wherein the means for pacing the heart from the region comprises:
means for providing bi-ventricular pacing of the heart from the septum.

47. The assembly of claim 37, wherein the means for enhancing stimulation of the region comprises:
means for delivering a conductive agent to the region.

48. The system of claim 47, wherein the means for delivering a conductive agent to the region comprises:
means for producing a connexin, or analog, derivative, or biological equivalent thereof, in the region.

49. The assembly of claim 48, wherein the means for producing a connexin in the region comprises:

means for producing connexin 43, or analog, derivative, or biological equivalent thereof, in the region.

50. The assembly of claim 49, wherein the means for producing connexin 43 comprises:

means for genetically modifying cells that over-express connexin 43, or analog, derivative, or biological equivalent thereof; and means for producing connexin 43 in the region with the genetically modified cells.

51. The cardiac stimulation assembly of claim 37, further comprising:

an electrical energy delivery assembly with an electrical energy emitter that is coupled to the elongate body and is adjustable to extend from the distal end portion and into a region of tissue within the heart when the distal end portion is at the location, and also with an electrical energy lead that is adapted to couple to the electrical energy emitter and also to a source of electrical energy along the proximal end portion when the electrical energy emitter is in the second position; and a volume of conductive agent coupled to the lumen and that is adapted to be delivered through the lumen into the region of tissue when the distal end portion is at the location and the electrical energy emitter is in the second position.

52. The assembly of claim 51, wherein the electrical energy emitter comprises a stimulation electrode.

53. The assembly of claim 51, wherein the electrical energy delivery assembly comprises:

an array of extendable electrode assemblies coupled to the elongate body and that each includes a stimulation electrode that is adjustable to extend from the elongate body at the location and into a unique location relative to the other extendable electrode assemblies within the region of tissue.

54. The assembly of claim 53, wherein each of the array of extendable electrode assemblies comprises an extendable needle that is adjustable to extend from the distal end portion of the elongate body and into cardiac tissue so as to position the respective stimulation electrode at the unique location.

55. The assembly of claim 54, wherein the stimulation electrode of each extendable electrode assembly is integrated with the needle.

56. The assembly of claim 54, wherein the stimulation electrode of each extendable electrode assembly is adjustable to extend from the respective needle to the unique respective location.

57. The assembly of claim 54, wherein the needle of at least one of the extendable electrode assemblies has a curved shape.

58. The assembly of claim 54, wherein the needle of at least one of the electrode assemblies comprises a superelastic metal alloy.

59. The assembly of claim 54, wherein the needle of at least one of the electrode assemblies comprises a shape memory metal alloy.

60. The assembly of claim 54, wherein the needle of at least one of the electrode assemblies comprises a nickel-titanium alloy.

61. The assembly of claim 53, wherein:

each of the array of extendable electrode assemblies comprises a relatively pliable tubular body with an inner lumen;

each stimulation electrode is located along the tubular body of the respective extendable electrode assembly; and wherein each relatively pliable tubular body is adapted to be deflected and steered through the region of tissue so as to place the respective stimulation electrode at the respective unique location.

62. The assembly of claim 61, further comprising:

a moveable stylet that is adapted to be moveably engaged within the inner lumen of at least one of the tubular bodies so as to adjust the tubular body to extend from the distal end portion of the elongate body and advance through the region of tissue such that the respective stimulation electrode is positioned at the respective unique location.

63. The assembly of claim 62, wherein:

the moveable stylet has a proximal end portion and a shaped distal end portion that is torquable within the inner lumen by torquing the proximal end portion proximally and externally of the tubular body so as to deflect and steer the tubular body in order to place the electrode.

64. The assembly of claim 53, further comprising:

an anchor that is extendable from the elongate body and adapted to anchor the distal end portion at the location such that the array of extendable electrode assemblies is adapted to be positioned at the respective unique locations along the region of tissue.

65. The assembly of claim 64, wherein the anchor comprises a stimulation electrode.

66. The assembly of claim 65, wherein:

the distal end portion of the elongate body comprises a distal tip; and a stimulation electrode is located at the distal tip.

67. The assembly of claim 51, wherein the cardiac stimulation assembly comprises:

a cardiac pacemaker.

68. The assembly of claim 67, wherein the cardiac pacemaker comprises:

a bi-ventricular cardiac pacemaker.

69. The assembly of claim 51, wherein the cardiac stimulation assembly comprises:

a cardiac defibrillator.

70. The assembly of claim 51, wherein the conductive agent comprises isolated living cells.

71. The assembly of claim 70, wherein the living cells comprise at least one of myoblasts, fibroblasts, or stem cells.

72. The assembly of claim 70, wherein the living cells are adapted to express a connexin at gap junctions with cardiac cells in the region of tissue.

73. The assembly of claim 72, wherein the living cells are adapted to express connexin 43 at the gap junctions.

74. The assembly of claim 73, wherein the living cells are genetically modified to over-express production of connexin 43.

75. The assembly of claim 51, wherein the conductive agent comprises an injectable preparation of a conductive non-living material that is adapted to enhance electrical conduction in the region.

76. The assembly of claim 75, wherein the conductive non-living material comprises an injectable preparation of a conductive metal.

* * * * *

UNITED STATES PATENT AND TRADEMARK OFFICE
CERTIFICATE OF CORRECTION

| | | |
|---|---|---|
| PATENT NO. | : 7,317,950 B2 | Page 1 of 1 |
| APPLICATION NO. | : 10/374899 | |
| DATED | : January 8, 2008 | |
| INVENTOR(S) | : Randall J. Lee | |

It is certified that error appears in the above-identified patent and that said Letters Patent is hereby corrected as shown below:

- Claim 43 line 43: Delete "41" and replace it with "42".

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,317,950 B2 | Page 1 of 1 |
| APPLICATION NO. | : 10/374899 | |
| DATED | : January 8, 2008 | |
| INVENTOR(S) | : Randall J. Lee | |

It is certified that error appears in the above-identified patent and that said Letters Patent is hereby corrected as shown below:

- Column 46, Claim 43 line 43: Delete "41" and replace it with "42".

This certificate supersedes the Certificate of Correction issued December 22, 2009.

Signed and Sealed this

Twelfth Day of January, 2010

David J. Kappos
*Director of the United States Patent and Trademark Office*